(12) United States Patent
Grimmond et al.

(10) Patent No.: US 9,155,804 B2
(45) Date of Patent: *Oct. 13, 2015

(54) CONTRAST ENHANCEMENT AGENTS AND METHOD OF USE THEREOF

(71) Applicant: General Electric Company, Schenectady, NY (US)

(72) Inventors: Brian James Grimmond, Clifton Park, NY (US); Michael James Rishel, Saratoga Springs, NY (US); Jeannette Christine Roberts, Burnt Hills, NY (US)

(73) Assignee: General Electric Company, Niskayuna, NY (US)

( * ) Notice: Subject to any disclaimer, the term of this patent is extended or adjusted under 35 U.S.C. 154(b) by 82 days.

This patent is subject to a terminal disclaimer.

(21) Appl. No.: 13/626,942

(22) Filed: Sep. 26, 2012

(65) Prior Publication Data

US 2014/0086846 A1    Mar. 27, 2014

(51) Int. Cl.
  *A61K 51/00* (2006.01)
  *A61M 36/14* (2006.01)
  *A61K 49/12* (2006.01)

(52) U.S. Cl.
  CPC .................................. *A61K 49/126* (2013.01)

(58) Field of Classification Search
  CPC ..................................................... A61K 49/51
  USPC ...................................................... 424/1.11
  See application file for complete search history.

(56) References Cited

U.S. PATENT DOCUMENTS

| | | | |
|---|---|---|---|
| 6,146,615 A | 11/2000 | Davies et al. | |
| 7,914,787 B2 | 3/2011 | Goldenberg et al. | |
| 8,105,567 B2 | 1/2012 | Ramalingam et al. | |
| 8,362,281 B2 * | 1/2013 | Grimmond et al. | 549/214 |
| 2008/0207913 A1 * | 8/2008 | Breitenkamp et al. | 548/237 |
| 2010/0092384 A1 | 4/2010 | Bumb et al. | |
| 2010/0233093 A1 | 9/2010 | Oh et al. | |
| 2011/0077396 A1 * | 3/2011 | Grimmond et al. | 544/64 |
| 2011/0117023 A1 | 5/2011 | Yamauchi et al. | |
| 2012/0121509 A1 | 5/2012 | Josephson et al. | |

FOREIGN PATENT DOCUMENTS

WO    WO 2008063721 A2 *   5/2008

OTHER PUBLICATIONS

Ladd et al. Bioconjugate Chem. 1999, 10, 361-370.*
Taliaferro Dissertation-Texas A&M, 1984.*
Yuanfang et al., "Radiolabeling of Monoclonal Antibodies with Metal Chelates", Pure and Applied Chemistry, vol. 63, Issue 3, pp; 1991; 37 Pages.
Erdogan et al., "Enhanced Tumor Visualization by Gamma-scintigraphy with 111In-labeled Polychelating-polymer Containing Immunoliposomes", Molecular Pharmaceutics, vol. 3, Issue 5,; Sep.-Oct. 2006; 1 page.
Ujula, "Studies on 68Ga-Based Agents for PET Imaging of Cancer and Inflammation", University of Turku, 2010; 86 Pages.

* cited by examiner

*Primary Examiner* — Michael G Hartley
*Assistant Examiner* — Sean R Donohue
(74) *Attorney, Agent, or Firm* — Eileen B. Gallagher

(57) ABSTRACT

A contrast agent composition and a method of diagnostic imaging are provided. The composition comprises a pharmaceutically acceptable carrier and a metal-complex comprising a ligand having structure (XXX):

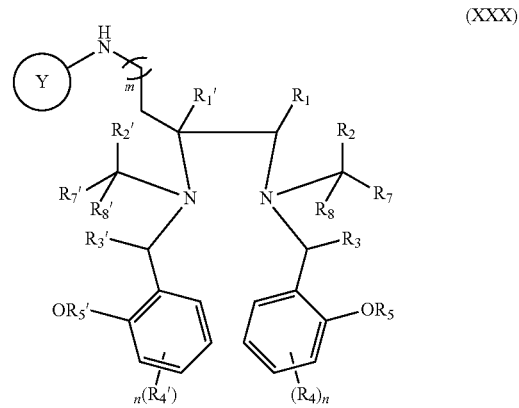

wherein $R_1$, $R_2$, $R_3$, $R_7$, $R_8$, $R'_1$, $R'_2$, $R'_3$, $R'_7$ and $R'_8$ are selected form hydrogen, a protected $C_1$-$C_3$ hydroxyalkyl group, or a $C_1$-$C_3$ alkyl group; $R_4$, $R'_4$ are selected from a hydrogen, a hydroxyl, a protected hydroxyl group, a protected $C_1$-$C_3$ hydroxyalkyl group, a $C_1$-$C_3$ alkyl group; n is an integer between 0 and 4; $R_5$, $R'_5$ are selected from a hydrogen, a protecting group comprising $C_1$-$C_{30}$ aliphatic radicals, $C_3$-$C_{30}$ cycloaliphatic radicals, $C_2$-$C_{30}$ aromatic radicals, m is an integer between 1 and 10; at least one of $R_7$ and $R'_7$ is acidic groups or protected acidic groups; Y comprises a protein or peptide moiety, a particle, a micelle, a liposome, an organic molecule, oligomer, polymer or a hydrophilic moiety.

21 Claims, 9 Drawing Sheets

CONTRAST ENHANCEMENT AGENTS AND METHOD OF USE THEREOF

CROSS REFERENCE

This application is related to U.S. patent application Ser. No. 13/626,918, entitled "Bifunctional Chelating Agents" filed concurrently on Sep. 26, 2012, the entire disclosure is incorporated herein by reference in its entirety.

CROSS REFERENCE TO RELATED APPLICATIONS

This application is a continuation-in-part of U.S. patent application Ser. No. 12/785,110, entitled "Intermediates for Hydroxylated Contrast Enhancement Agents", filed on May 21, 2010.

FIELD

This invention relates to contrast enhancement agents for use in magnetic resonance imaging, more particularly to metal chelating ligands and metal-chelate compounds useful in the preparation of such contrast enhancement agents.

BACKGROUND

Non-invasive magnetic resonance imaging (MRI) provides anatomical details for diagnosis and offers a highly resolved contrast between the specific tissues or organs of interest. The MR contrast enhancement agents improves both the quality of images obtained in an MR imaging procedure and the efficiency with which such images can be gathered. The use of MR contrast enhancement agents in MR imaging protocols has proven to be a valuable addition to the MRI technique.

Various metal chelates may serve as MR contrast enhancement agents, however the toxicity of free metal ions, stability of metal-chelate complex, and rapid rate of clearance of the chelates from the body during the imaging procedure are a few of the disadvantages associated with metal chelates. For example, while gadolinium (Gd) chelates are non-toxic, the Gd metal in free ionic form is toxic. For manganese (Mn)-chelate, dissociation of the chelating ligand from the metal center happens, which is also not desirable. As such, considerable efforts have been made to increase the efficiency and reduce the latent toxicity of the existing contrast enhancement agents. In comparing metal chelates, the contrast enhancement agents comprising iron (Fe) is an attractive alternative as compared to contrast agents with other metals, and one of the reasons is biocompatibility of Fe. This has led to increased interest in the use of iron-based materials as contrast agents for MRI.

The image quality of an agent may be increased by incorporating a moiety within the agent, wherein the moiety increases the agent size or targets a disease related biomarker. Either of these approaches improves selective localization of the agent at a diseased tissue lesion. This incorporation may be accomplished by the use of a bifunctional chelate, which binds to the metal as well as to a second moiety. The examples of iron-based bifunctional chelates are EDTA and deferoxamine, however, these chelates either pose a safety concern as they are redox active or have an insufficient MR signal. Furthermore, the known chelates employ isocyanate and isothiocyanate conjugation chemistries to attach a second moiety, which are hydrolytically sensitive functionalities that provide unstable conjugates in-vivo.

The alternative forms of bifunctional chelates and alternative methods of attaching a second moiety to an agent to enable bifunctionality is a long felt need. Therefore, a contrast enhancement agent comprising a bifunctional chelate having high in vitro and/or in vivo stability, prompt clearance from the body, ability to generate improved image quality at lower patient dosages, greater patient tolerance and safety for higher doses is highly desirable.

BRIEF DESCRIPTION

One embodiment of a contrast agent composition, comprises a pharmaceutically acceptable carrier or excipient; and a metal-complex comprising a metal and a ligand having structure (XXX):

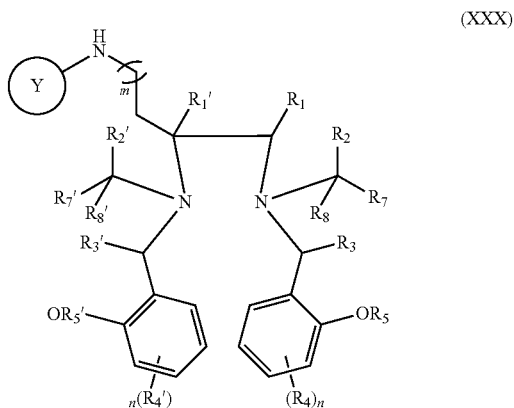

(XXX)

wherein $R_1$, $R_2$, $R_3$, $R_7$, $R_8$, $R'_1$, $R'_2$, $R'_3$, $R_7'$ and $R_8'$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxyl group, a protected $C_1$-$C_3$ hydroxyalkyl group, a $C_1$-$C_3$ alkyl group; and n is an integer between 0 and 4; $R_5$ and $R'_5$ are independently at each occurrence a hydrogen or a protecting group selected from the group consisting of $C_1$-$C_{30}$ aliphatic radicals, $C_3$-$C_{30}$ cycloaliphatic radicals, $C_2$-$C_{30}$ aromatic radicals and m is an integer between 0 and 10; with the proviso that at least one of $R_7$ and $R'_7$ is an acidic group or protected acidic groups; and Y comprises an antibody, a natural peptide, a synthetic peptide, an amino acid, a polypeptide, a protein, a nanoparticle, a micelle, a liposome, a peptidomimetic, an organic molecule, a sugar, an oligosaccharide a nucleic acid oligomer, polymer, or a hydrophilic moiety.

In one embodiment of a contrast agent composition suitable for injection into a mammalian subject, comprises a pharmaceutically acceptable carrier or excipient; and a metal-complex having a structure (XXXXII):

(XXXXII)

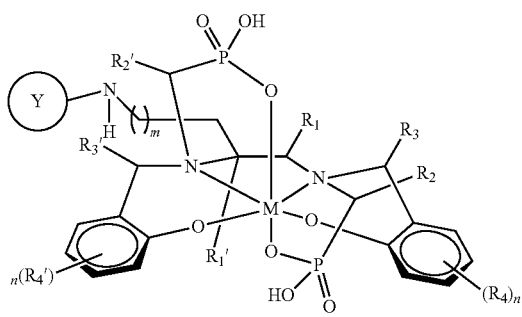

wherein $R_1$, $R_2$, $R_3$, $R'_1$, $R'_2$, and $R'_3$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxyl group, a protected $C_1$-$C_3$ hydroxyalkyl group, a $C_1$-$C_3$ alkyl group or hydrogen; and n is an integer between 0 and 4; m is an integer between 0 and 10; and Y comprises an antibody, a natural or synthetic peptide or amino acid, a protein, a nanoparticle, a micelle, a liposome, a poly(peptide), a peptidomimetic, an organic molecule, a sugar, an oligosaccharide a nucleic acid oligomer or polymer, or a polyethylene ether moiety.

One example of a method of diagnostic imaging using a contrast agent, comprises subjecting an individual to the diagnostic imaging, wherein the individual is administered with a contrast agent comprising a metal-complex and a pharmaceutically acceptable carrier or excipient, and wherein the metal-complex has a structure of (XXXIIX):

(XXXXII)

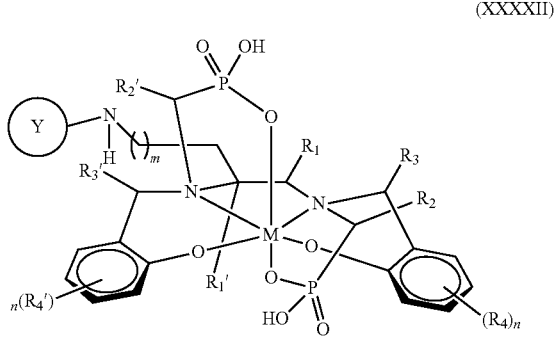

wherein $R_1$, $R_2$, $R_3$, $R'_1$, $R'_2$, and $R'_3$ are independently at each occurrence hydrogen, a protected $C_1$-$C_3$ hydroxyalkyl group, or a $C_1$-$C_3$ alkyl group; $R_4$ and $R'_4$ are independently at each occurrence a protected hydroxyl group, a protected $C_1$-$C_3$ hydroxyalkyl group, a $C_1$-$C_3$ alkyl group or hydrogen; and n is an integer between 0 and 4; m is an integer between 0 and 10; M is a metal comprising Fe, Mn, Ga, In, Gd, W, Ta, or B; and Y comprises an antibody, a natural or synthetic peptide or amino acid, a protein, a nanoparticle, a micelle, a liposome, a poly(peptide), a peptidomimetic, an organic molecule, a sugar, an oligosaccharide a nucleic acid oligomer or polymer, or a hydrophilic moiety.

DRAWINGS

These and other features, aspects, and advantages of the present invention will become better understood when the following detailed description is read with reference to the accompanying drawings in which like characters represent like parts throughout the drawings, wherein.

Figure 5:
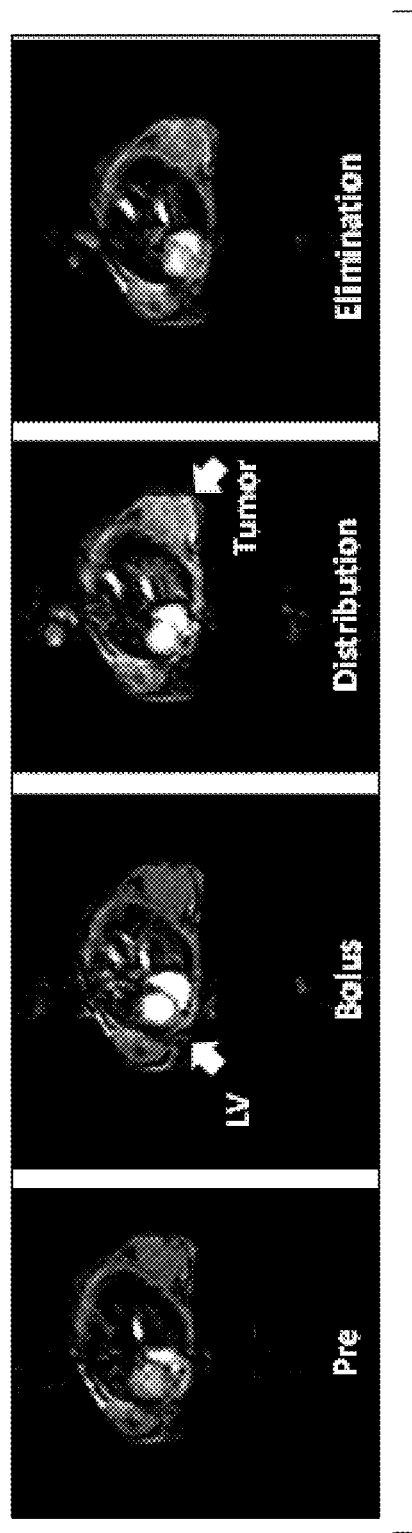

FIG. 5 provides an image showing MR signals in the heart and tumor tissue before administration, during administration, on distribution and elimination of a bifunctional metal-chelate.

Figure 6:
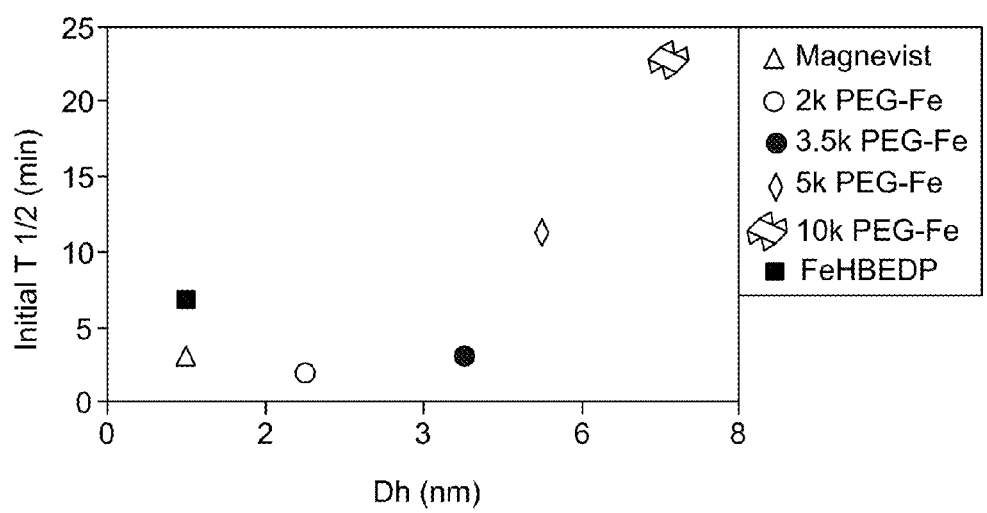

FIG. 6 is a graph showing distribution half-lives of the pegylated iron-chelates from the blood.

Figure 7A:
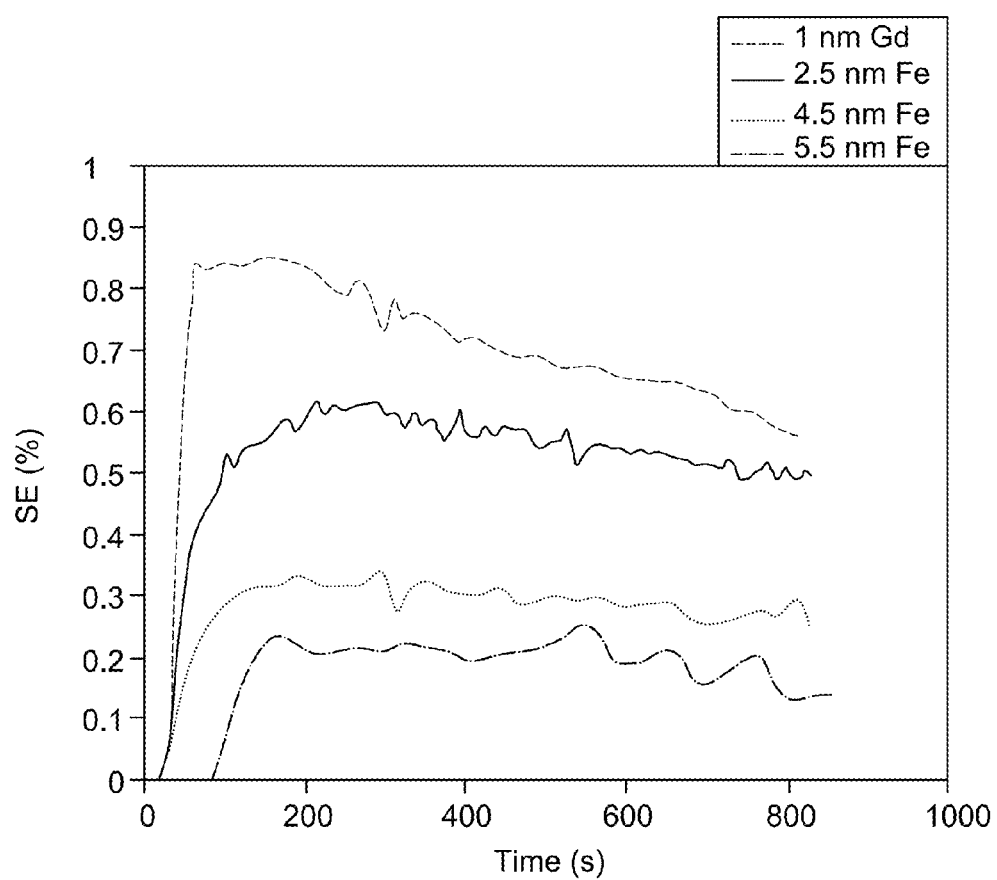

FIG. 7A is whole tumor contrast enhanced MR profiles of a preclinical models, treated with pegylated iron chelates and Magnevist as a control.

Figure 7B:
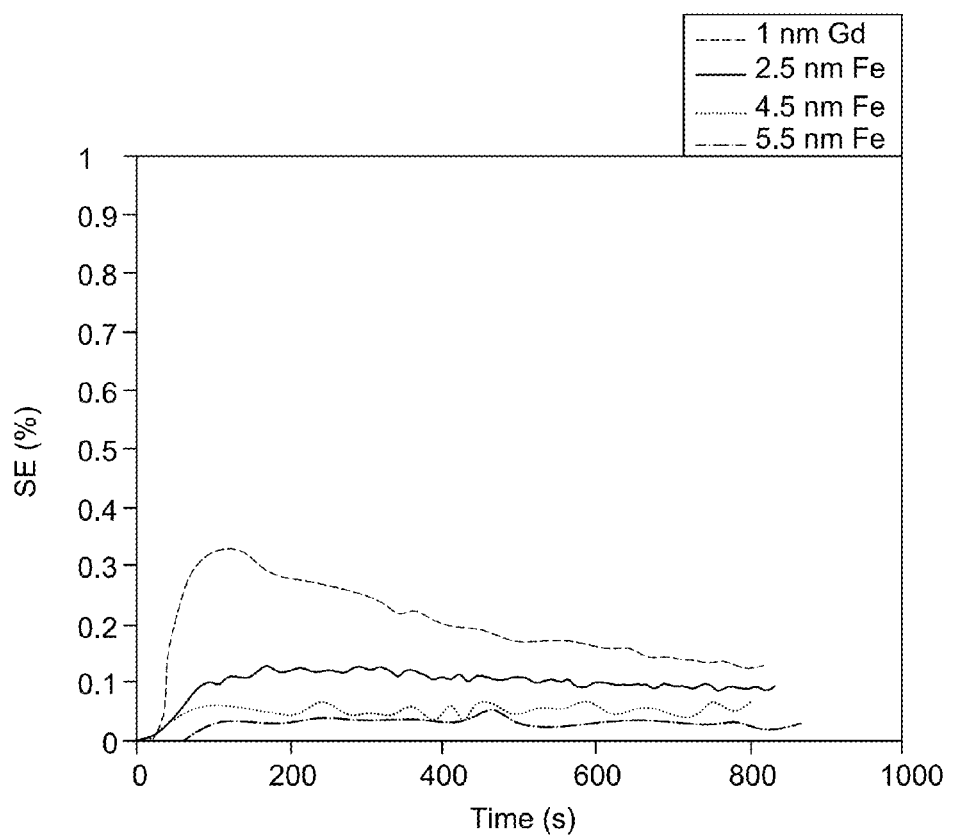

FIG. 7B is muscle contrast enhanced MR profiles of preclinical models treated with pegylated iron chelates and Magnevist as a control.

Figure 8A:
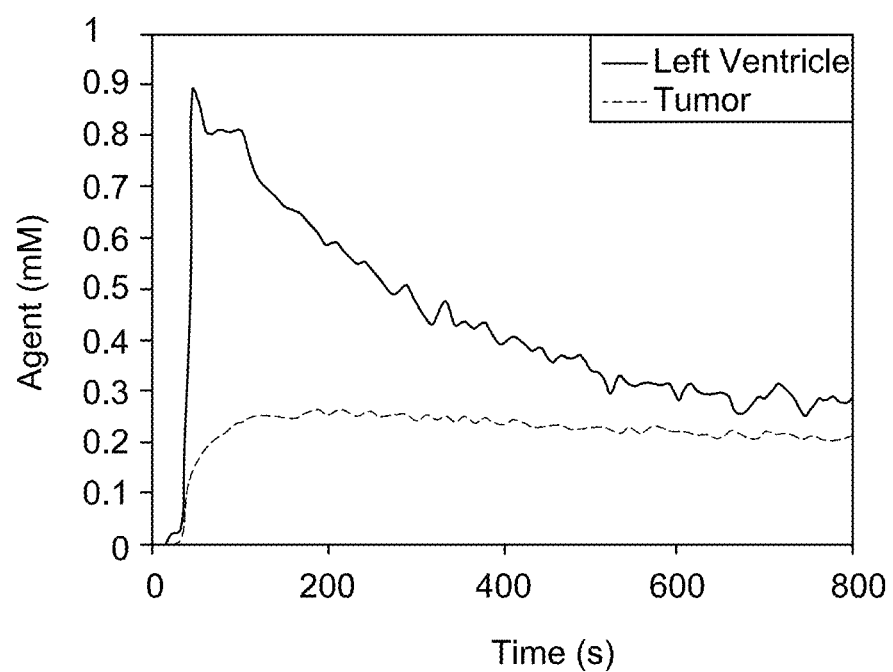

FIG. 8A is a concentration vs. time curve of the left ventricle and whole tumor generated from the MR signal following contrast agent administration.

Figure 8B:
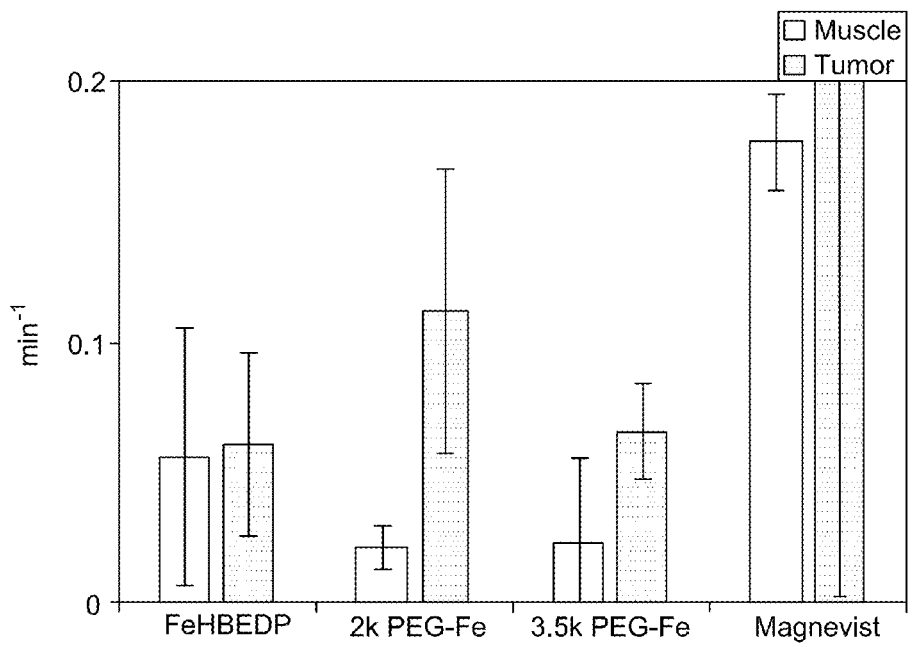

FIG. 8B is a graph showing the pharmacokinetic characterization of whole tumor and muscle tissues by vascular permeability ($K^{trans}$) quantitation.

Figure 8C:
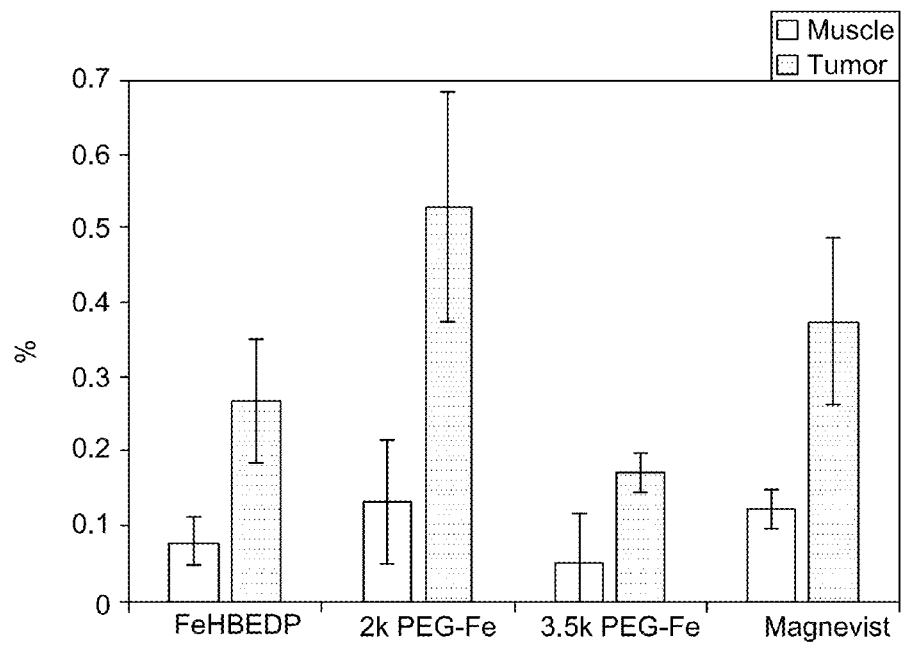

FIG. 8C is a graph showing the pharmacokinetic characterization of whole tumor and muscle tissues by extravascular extracellular volume ($V_e$).

DETAILED DESCRIPTION

In the following specification and the claims, which follow, reference will be made to a number of terms, which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC($CF_3$)$_2$PhO—), 4-chloromethylphen-1-yl, 3-trifluorovinyl-2-thienyl, 3-trichloromethylphen-1-yl (i.e., 3-$CCl_3$Ph-), 4-(3-bromoprop-1-yl)phen-1-yl (i.e., 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphen-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}$C($CF_3$)$_2$$C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., CH$_3$CHBrCH$_2$$C_6H_{10}$O—), and the like. Further examples of cycloaliphatic radicals include 4-allyloxycyclohex-1-yl, 4-aminocyclohex-1-yl (i.e., H$_2$$C_6H_{10}$—), 4-aminocarbonylcyclopent-1-yl (i.e., NH$_2$COC$_5H_8$—), 4-acetyloxycyclohex-1-yl, 2,2-dicyanoisopropylidenebis(cyclohex-4-yloxy) (i.e., —OC$_6H_{10}$C(CN)$_2$$C_6H_{10}$O—), 3-methylcyclohex-1-yl, methylenebis(cyclohex-4-yloxy) (i.e., —OC$_6H_{10}$CH$_2$$C_6H_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC$_6H_{10}$(CH$_2$)$_6$$C_6H_{10}$O—), 4-hydroxymethylcyclohex-1-yl (i.e., 4-HOCH$_2$$C_6H_{10}$—), 4-mercaptomethylcyclohex-1-yl (i.e., 4-HSCH$_2$$C_6H_{10}$—), 4-methylthiocyclohex-1-yl (i.e., 4-CH$_3$SC$_6H_{10}$—), 4-methoxycyclohex-1-yl, 2-methoxycarbonylcyclohex-1-yloxy (2-CH$_3$OCOC$_6H_{10}$O—), 4-nitromethylcyclohex-1-yl (i.e., NO$_2$CH$_2$$C_6H_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)$_3$SiCH$_2$CH$_2$$C_6H_{10}$—), 4-vinylcyclohexen-1-yl, vinylidenebis(cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7$O—) represents a $C_4$ cycloaliphatic radical. The cyclohexylmethyl radical ($C_6H_{11}CH_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hexamethylene, hydroxymethyl (i.e., —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e., $CH_3$—) is an example of a $C_1$ aliphatic radical. A decyl group (i.e., $CH_3(CH_2)_9$—) is an example of a $C_{10}$ aliphatic radical.

Many of the compounds described herein may contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

One or more embodiments of the present invention provides a contrast agent composition comprising a metal-complex, wherein the metal complex comprises an amine-based bifunctional chelating agent and demonstrate the utility in modifying the in vivo distribution of the corresponding imaging agents. The chelate class is based on the hydroxy bis ethylene diamine dicarboxylate (HBED) or hydroxy bis ethylene diamine diphosphonate (HBEDP) framework which is suitable for binding oxyphilic metals such as Fe, Ga, In or Ti. In one or more embodiments, the contrast agents comprising metal-complexes or metal-chelates are used for in vivo imaging, wherein the in vivo performance is defined by the chemical structure and functionality of the chelates. The term "chelate" is interchangeably used herein as a "ligand" or "bifunctional ligand" hereinafter.

One embodiment of the present invention provides a contrast agent composition comprising a pharmaceutically acceptable carrier or excipient and a metal-chelate complex comprising a ligand, wherein the ligand has an idealized structure (XXX),

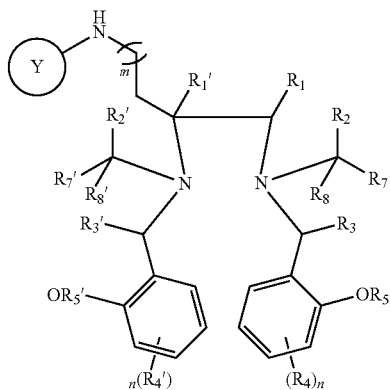

(XXX)

wherein $R_1$, $R_1'$, $R_2$, $R_2'$, $R_3$, $R_3'$, $R_8$, and $R_8'$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxy group, a protected $C_1$-$C_3$ hydroxyalkyl group, or a $C_1$-$C_3$ alkyl group; and n is an integer between 0 and 4; $R_5$ and $R'_5$ are independently at each occurrence a hydrogen or a protecting group selected from the group consisting of $C_1$-$C_{30}$ aliphatic radicals, $C_3$-$C_{30}$ cycloaliphatic radicals, and $C_2$-$C_{30}$ aromatic radicals; and m is an integer between 0 and 10; with the proviso that at least one of $R_7$ or $R'_7$ are acidic group or protected acidic groups and Y comprises an antibody, a natural peptide, a synthetic peptide, an amino acid, a polypeptide, a protein, a nanoparticle, a micelle, a liposome, a peptidomimetic, an organic molecule, a sugar, an oligosaccharide a nucleic acid oligomer, polymer, or a hydrophilic moiety. In another embodiment, a contrast agent composition comprises a metal chelating ligand having a stereoisomer of the idealized structure XXX.

In some embodiments, $R_1$, $R_2$, $R_3$, $R_4$, $R_5$, $R_7$ and $R_8$ are the same as $R_1'$, $R_2'$, $R_3'$, $R_4'$, $R_5'$, $R_7'$, and $R'_8$ respectively. As noted, $R_1$, $R_1'$, $R_2$, $R_2'$, $R_3$, $R_3'$, $R_8$, and $R_8'$ are independently at each occurrence hydrogen, a protected $C_1$-$C_3$ hydroxyalkyl group, or a $C_1$-$C_3$ alkyl group. Accordingly, in one example, if the $R_1$ is an alkyl group, such as an ethyl group, then $R_1$ is also an ethyl group and vice versa. In some other examples, if the $R_1$ is a hydroxyalkyl group, such as hydroxypropyl group, then $R_1'$ is also a hydroxypropyl group and vice versa. In one specific embodiment, $R_1$ and $R'_1$ are both hydrogen.

As noted, $R_4$ and $R'_4$ are independently at each occurrence a hydrogen, a hydroxyl, a protected hydroxy group, a protected $C_1$-$C_3$ hydroxyalkyl group, or a $C_1$-$C_3$ alkyl group; and n is an integer between 0 and 4. Accordingly, in some embodiments, $R_4$ is a hydroxyl group, wherein $R'_4$ is a protected $C_1$-$C_3$ hydroxyalkyl group, for example a hydroxymethyl group and vice versa. In some other embodiments, $R_4$ is a protected $C_1$-$C_3$ hydroxyalkyl group, wherein $R'_4$ is a $C_1$-$C_3$ alkyl group and vice versa. For example, $R_4$ is one of the hydroxymethyl, hydroxyethyl or hydroxypropyl groups, wherein $R'_4$ is one of the methyl, ethyl or propyl groups. In another embodiment, $R_4$ is a hydroxyl group, wherein $R'_4$ is a $C_1$-$C_3$ alkyl group, for example, $R'_4$ is one of the methyl, ethyl or propyl groups and vice versa. Alternatively, in some other embodiments, $R_4$ and $R'_4$ are identical groups and may be selected from a protected hydroxy group, a protected $C_1$-$C_3$ hydroxyalkyl group, or a $C_1$-$C_3$ alkyl group. For example, both of the $R_4$ and $R'_4$ are hydroxyl group. In another example, both of the $R_4$ and $R'_4$ are either of the hydroxymethyl, hydroxyethyl or hydroxypropyl groups. In another example, both of the $R_4$ and $R'_4$ are either methyl, or ethyl or propyl groups. In another example, both of the $R_4$ and $R'_4$ are hydrogen.

As noted, n is an integer between 0 and 4, accordingly, the occurrence of $R_4$ and $R'_4$ may vary between 0 and 4. In some embodiments, the occurrence of $R_4$ and $R'_4$ is 0, in that case, the benzene ring of compound (XXX) does not have any substitution of $R_4$ and/or $R'_4$. In some other embodiments, n is 1 for either $R_4$ or $R'_4$ or both, wherein the substitution of $R_4$ or/and $R'_4$ may be in a ortho, meta or para position of the benzene ring. Similarly, in some other embodiments, if n is 2 for either $R_4$ or $R'_4$ or both, then the substitutions may present either in ortho, meta; ortho, para; or meta, para positions. In some other embodiments, if n is 3 for either $R_4$ or $R'_4$ or both, then the substitutions may present either in ortho, meta, para; or in meta, para, meta positions. The embodiments, where n is 4 for either $R_4$ or $R'_4$ or both, then the substitutions are in ortho, meta, para, meta positions. The substitutions for both of the benzene rings of compound (XXX) may be the same or different. For example, the $R_4$ is at ortho position of one benzene ring whereas $R'_4$ is also in an ortho position of the other benzene ring. In some other examples, $R_4$ is at ortho position of one benzene ring whereas $R'_4$ is in meta position of the other benzene ring. In one example, either of the $R_4$ and $R'_4$ is hydrogen.

As noted, $R_5$ and $R'_5$ are independently at each occurrence a hydrogen or a protecting group selected from the groups consisting of $C_1$-$C_{30}$ aliphatic radicals, $C_3$-$C_{30}$ cycloaliphatic radicals, $C_2$-$C_{30}$ aromatic radicals and hydrogen. In one or more embodiments, at least one of the $R_5$ and $R'_5$ is independently at each occurrence a hydrogen, an ethyl group, a trichloroethyl group, a beta-cyanoethyl group, a trimethylsilyl ethyl group, a tertiary butyl group, tetrahydropyranyl (THP), methoxthyethoxymethyl group (MEM), butyldimethylsilyl group, trimethylsilyl, 2-(trimethylsilyl)ethoxymethyl (SEM), a triisopropylsilyl (TIPS), a tert-butyl (t-Bu), a tert-butyldiphenylsilyl (TBDPS), a Benzyloxymethyl (BOM), a methylthiomethyl (MTM) or a combination thereof. In some examples, $R_5$ is an ethyl group, whereas $R'_5$ is a trichloroethyl group and vice versa. In some other examples, $R_5$ is a beta-cyanoethyl group, whereas $R'_5$ is a trimethylsilyl ethyl group and vice versa. In one example, $R_5$ is a butyldimethylsilyl group, whereas $R'_5$ is a trimethylsilyl group and vice versa. Alternatively, in some other embodiments, $R_5$ and $R'_5$ are identical, such as both of the $R_5$ and $R'_5$ are ethyl groups, trichloroethyl groups, beta-cyanoethyl groups, trimethylsilyl ethyl groups, tertiary butyl groups, THP, methoxthyethoxymethyl groups, butyldimethylsilyl groups or trimethylsilyl groups. In one example, both of the $R_5$ and $R'_5$ are MEM groups.

As noted, m is an integer between 0 and 10, accordingly, the length of the aliphatic chain may vary between 0 and 10. The aliphatic chain connects to amine or substituted amine, and the length of the chain may vary. This aliphatic chain may be referred to herein as a "linker". In one example, when m is 0, amine or substituted amine is linked to the carbon that contains R1' via a methylene unit. In some embodiments, the methylene unit is repeated for 2 to 10 times, when m varies from 1 to 10. For example, when m is 1, the linker is an ethylene unit. For another example, when m is 2, the linker is a propylene unit.

As noted, at least one of the $R_7$ and $R'_7$ is either acidic or a protected acidic group. In one embodiment, either $R_7$ or $R'_7$ of the chelate is an acidic group, such as a carboxylate group. In some embodiments, at least one of the $R_7$ and $R'_7$ of the compound (XXX) is a phosphonate, a sulphonate, a carboxylate, a phenol, a substituted phenol, a tetrazole, a methyl thiazolidine dione, a methyl oxazolidine dione, a methyl imidazolidine dione, a pyridazineoxide, a benzene sulfonamide or a combination thereof. Non-limiting examples of acidic groups are included in Table 1. In one embodiment, at least one of the $R_7$ and $R'_7$ of the compound (XXX) is a phosphonate or a carboxylate group. In some embodiments, both of the $R_7$ and $R'_7$ are protected acidic groups, wherein the groups may be the same or different protected acidic groups. In one or more embodiments, the $R_7$ and $R'_7$ groups may be different protected acidic groups. For example, $R_7$ is an acidic group, such as phosphonate group, wherein $R'_7$ is also an acidic group, may be a sulphonate group or carboxylate group or vice versa. In some embodiments, the $R_7$ and $R'_7$ groups may be the same acidic groups. In some other embodiments, both of the $R_7$ and $R'_7$ are of same group, such as, for example both of the $R_7$ and $R'_7$ are phosphonate group.

TABLE 1

Examples of acidic groups.

| Entry | $R_7$ and/or $R'_7$ groups |
| --- | --- |
| Carboxylate | ![carboxylate structure] |
| Phosphonate | ![phosphonate structure] |
| Sulphonate | ![sulphonate structure] |
| substituted phenol | ![substituted phenol structure]<br>R = H, Alkyl, Acyl, electron withdrawing group |
| methyl thiazolidine dione | ![methyl thiazolidine dione structure] |
| methyl imidazolidine dione | ![methyl imidazolidine dione structure] |
| methyl oxazolidine dione, | ![methyl oxazolidine dione structure] |

TABLE 1-continued

Examples of acidic groups.

| Entry | R₇ and/or R'₇ groups |
|---|---|
| Tetrazole | (tetrazole structure) |
| Pyridazineoxide | (pyridazine N-oxide with OH structure) |
| benzene sulfonamide | (benzenesulfonamide structure) |

The contrast agent comprising a compound of structure XXX, wherein Y comprises an antibody, a natural peptide, a synthetic peptide, an amino acid, a polypeptide, a protein, a nanoparticle, a micelle, a liposome, a peptidomimetic, an organic molecule, a sugar, an oligosaccharide a nucleic acid oligomer, polymer, or a hydrophilic moiety. In one or more embodiments, the Y comprises a hydrophilic moiety. In one embodiment, the Y comprises a polyethylene ether moiety, such as polyethylene glycol (PEG).

As noted, the contrast agents comprising the ligand of structure (XXX), wherein the chelating agent is a bifunctional ligand. The acidic groups $R_7$ and $R'_7$, two nitrogen atoms, and two oxygen atoms from the $OR_5$ and $OR'_5$ form coordination complex with a metal ion in combination, residing the metal ion at the center. As noted, the ligand is functional through multiple atoms of the core of the ligand which forms a coordination complex with a metal atom or ion present at the center of the ligand. In one embodiment, in addition to the coordination with the metal ion, an aliphatic amine linker is present on the carbon atom comprising $R'_1$, as referred to structure (XXX). In addition to the coordination site which is the core of the ligand, the aliphatic amine linker is used as another site for binding any other structural moiety. For example, the aliphatic amine linker binds to an oligomer, such as polyethylene ether, such as PEG. This aliphatic amine linker is used herein as the second site of the same ligand wherein the first site is the core of the ligand, and justifies the ligand as a "bifunctional ligand" as referred to herein.

One or more hydrophilic moieties may be added to the chelating ligand to modify hydrophilic property of the chelates. In one or more embodiments, the metal-chelates are modified to form a hydrophilic metal-chelate complex, by adding one or more hydrophilic moieties to the chelating agent or ligand. In one embodiment, one or more hydrophilic moieties added to the chelating agent, wherein the hydrophilic moieties comprise polyethylene ether moieties.

The contrast agents presently disclosed are based on chelating agents comprising ethylene oxide with the poly(ethylene oxides/glycols) (PEG), having an average molecular weight greater than about 2,000 daltons and less than or equal to about 30,000 daltons. When reference is made herein to the molecular weight of PEG, the disclosed value represents an average molecular weight for the compound; a preparation of that compound may include species that vary in molecular weight from the average anywhere from 10-28%. For example, as indicated by the manufacturer, a preparation of PEG 3350 has an average molecular weight of 3350 daltons with molecular species in the preparation having molecular weights between 3000 and 3750 daltons. Spectral analysis of the PEG 5000 material used showed a size range from about 4,000 to 6,400 daltons with the average being around 5,000 daltons.

The modified hydrophilic metal-chelates may be used as therapeutic agents or as contrast agents in diagnostic imaging. In an imaging application, the modified metal-chelate complexes of the invention are administered to a subject for imaging, in some embodiments a mammalian subject. In a therapeutic application, a contrast agent with the modified iron-chelates is administered to a subject, for example, to address an iron deficiency. The modified hydrophilic metal-chelates may comprise one or more of chelating ligands derived from generic structure (XXX), as described hereinafter.

In some embodiments, a contrast agent composition is provided, wherein the composition comprises a ligand of structure (XXXI).

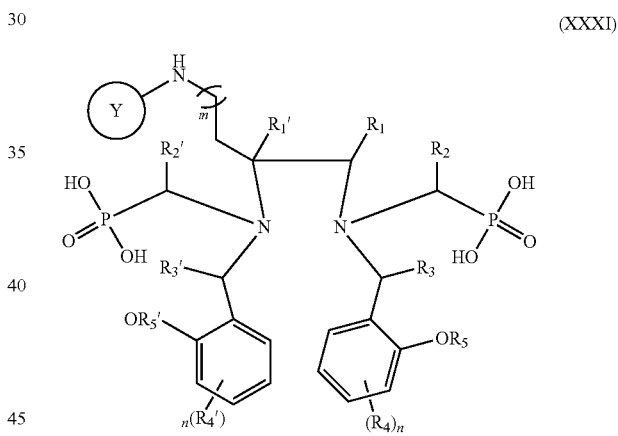

(XXXI)

wherein $R_1$, $R_2$, $R_3$ $R'_1$, $R'_2$, and $R'_3$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxyl group, a protected $C_1$-$C_3$ hydroxyalkyl group, or a $C_1$-$C_3$ alkyl group; and n is an integer between 0 and 4; $R_5$ and $R'_5$ are independently at each occurrence a hydrogen or a protecting group selected from the group consisting of $C_1$-$C_{30}$ aliphatic radicals, $C_3$-$C_{30}$ cycloaliphatic radicals, $C_2$-$C_{30}$ aromatic radicals; m is an integer between 0 and 10; and Y comprises an antibody, a natural or synthetic peptide or amino acid, a protein, a nanoparticle, a micelle, a liposome, a poly(peptide), a peptidomimetic, an organic molecule, a sugar, an oligosaccharide a nucleic acid oligomer or polymer, or a hydrophilic moiety.

In one embodiment of structure (XXX), both of the $R_8$ and $R'_8$ are hydrogen. In structure (XXXII), the protected acidic groups of $R_7$ and $R'_7$ are phosphonates. In this embodiment, a contrast agent composition comprising a ligand of structure (XXXII):

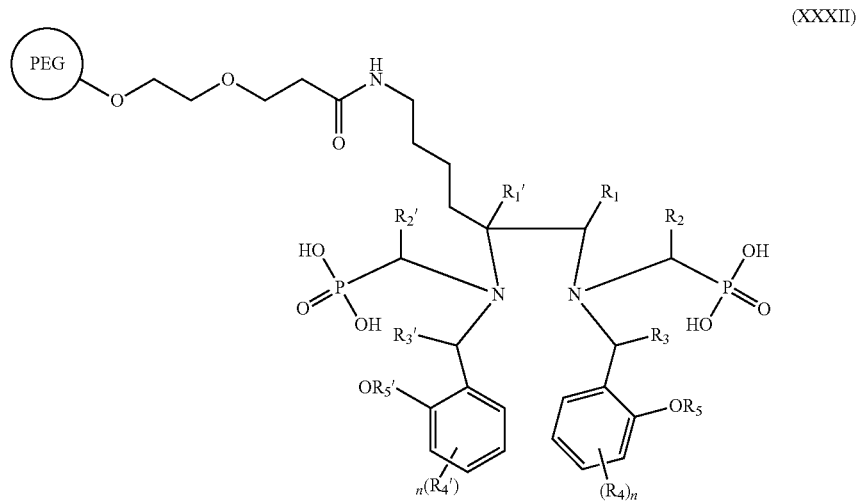

(XXXII)

wherein $R_1$, $R_2$, $R_3$ $R'_1$, $R'_2$, and $R'_3$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, protected hydroxyl group, a protected $C_1$-$C_3$ hydroxyalkyl group, or a $C_1$-$C_3$ alkyl group; and n is an integer between 0 and 4; $R_5$ and $R'_5$ are independently at each occurrence a protecting group selected from the group consisting of $C_1$-$C_{30}$ aliphatic radicals, $C_3$-$C_{30}$ cycloaliphatic radicals, and $C_2$-$C_{30}$ aromatic radicals; and PEG is a polyethylene ether moiety.

In one embodiment, a contrast agent composition comprises a ligand of structure (XXXIII)

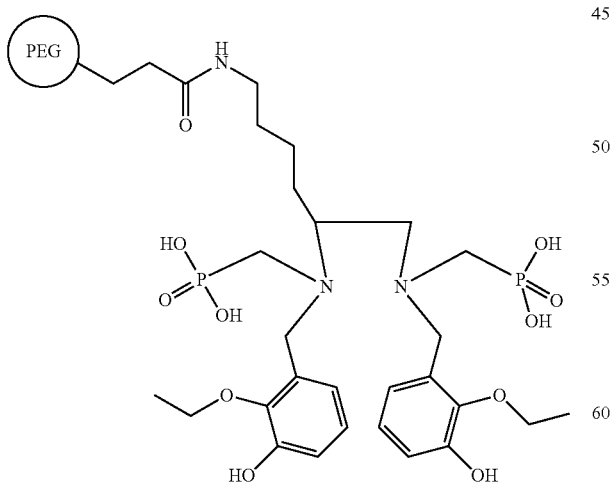

(XXXIII)

In some embodiments, a contrast agent composition comprises a ligand of structure (XXXIII-A).

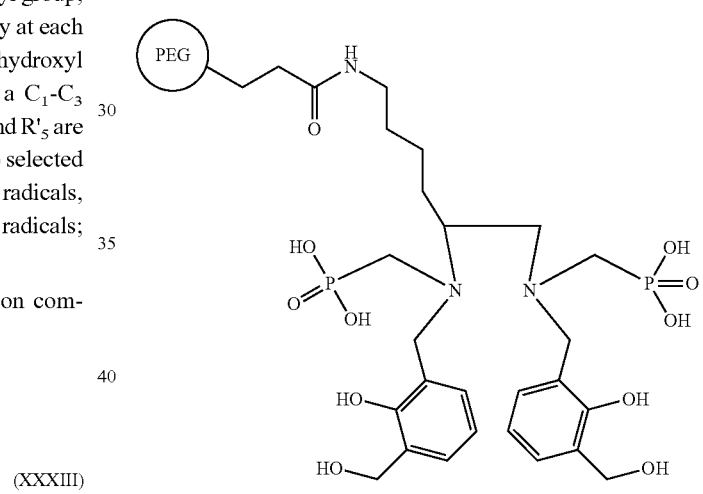

(XXXIII-A)

In some embodiments, a contrast agent composition comprises a ligand of structure (XXXIII-B).

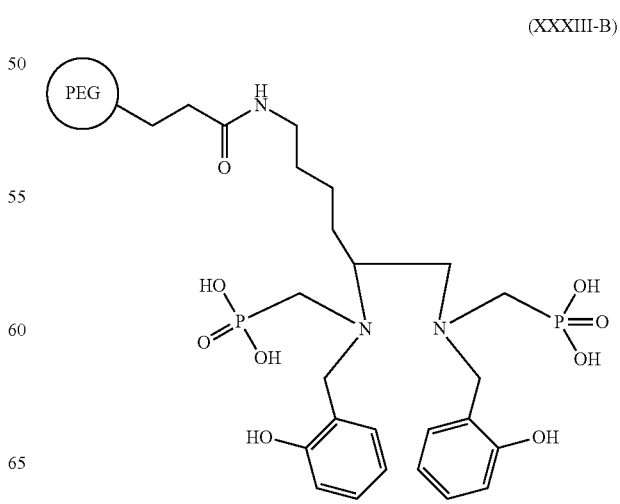

(XXXIII-B)

In one embodiment, a contrast agent composition comprises a ligand of structure (XXXIV):

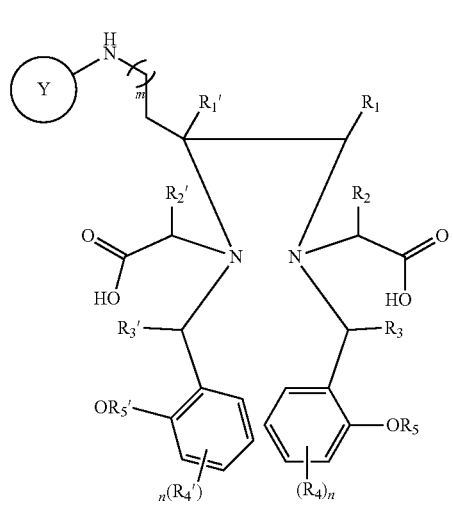

(XXXIV)

wherein $R_1$, $R_2$, $R_3$ $R'_1$, $R'_2$, and $R'_3$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxyl group, a protected $C_1$-$C_3$ hydroxyalkyl group, a $C_1$-$C_3$ alkyl group or hydrogen, and n is an integer between 0 and 4; $R_5$ and $R'_5$ are independently at each occurrence selected from the group consisting of $C_1$-$C_{30}$ aliphatic radicals, $C_3$-$C_{30}$ cycloaliphatic radicals, $C_2$-$C_{30}$ aromatic radicals and m is an integer between 0 and 10; and Y comprises an antibody, a natural or synthetic peptide or amino acid, a protein, a nanoparticle, a micelle, a liposome, a poly(peptide), a peptidomimetic, an organic molecule, a sugar, an oligosaccharide a nucleic acid oligomer or polymer, or a hydrophilic moiety.

In one embodiment of the contrast agent, the ligand has a structure XXXV:

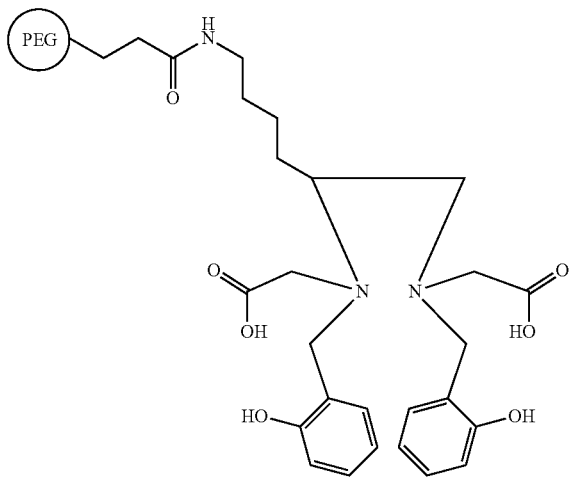

(XXXV)

In one embodiment of the contrast agent, the ligand has a structure (XXXVI):

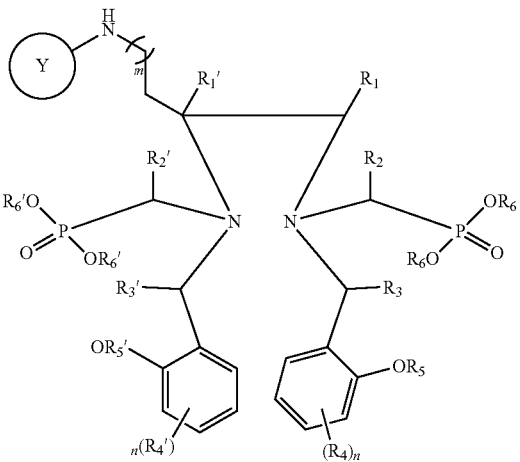

(XXXVI)

wherein $R_1$, $R_2$, $R_3$ $R'_1$, $R'_2$, and $R'_3$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxyl group, a protected $C_1$-$C_3$ hydroxyalkyl group, a $C_1$-$C_3$ alkyl group; and n is an integer between 0 and 4; $R_5$ and $R'_5$ are independently at each occurrence a hydrogen or a protected group selected from the group consisting of $C_1$-$C_{30}$ aliphatic radicals, $C_3$-$C_{30}$ cycloaliphatic radicals, $C_2$-$C_{30}$ aromatic radicals and m is an integer between 0 and 10; with the proviso that at least one of $R_6$ and $R_6'$ is independently at each occurrence a hydrogen, an ethyl group, a trichloroethyl group, a beta-cyanoethyl group, a trimethylsilyl ethyl group, or a tertiary butyl group, and Y comprises an antibody, a natural or synthetic peptide or amino acid, a protein, a nanoparticle, a micelle, a liposome, a poly(peptide), a peptidomimetic, an organic molecule, a sugar, an oligosaccharide a nucleic acid oligomer or polymer, or a hydrophilic moiety.

In one embodiment of the contrast agent, the ligand has a structure XXXVII:

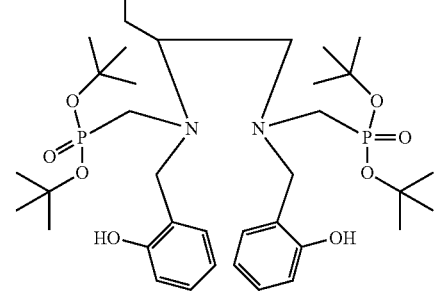

(XXXVII)

In one embodiment of the contrast agent, the ligand has a structure XXXVIII:

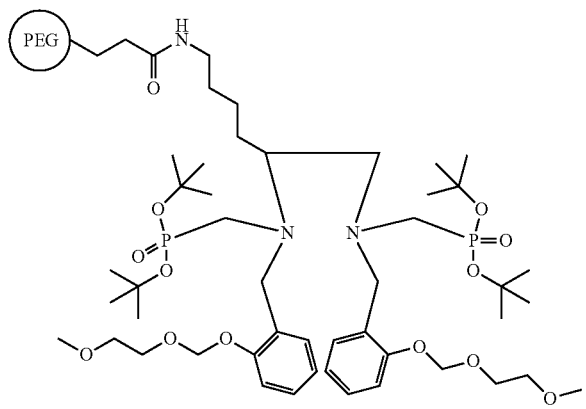
(XXXVIII)

In one embodiment of the contrast agent, the ligand has a structure XXXVIII-A

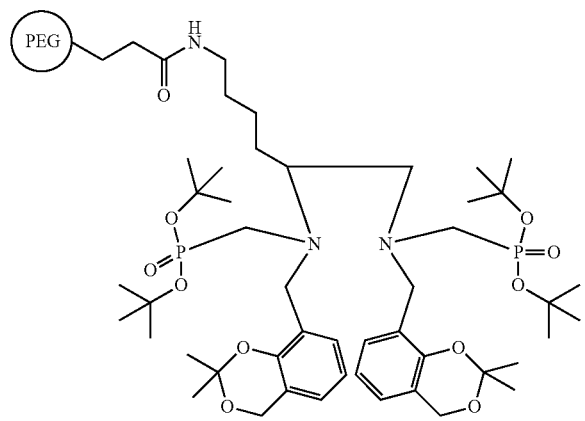
(XXXVIII-A)

No absolute or relative stereochemistry is intended to be shown for a structure, and the structures are intended to encompass all possible absolute and relative stereochemical configurations, unless specified otherwise. The chelating agent may comprise a compound of structure (XXXIX), which has a specific stereochemical arrangement which is shown as a non-limiting example. Thus, structure XXXIX depicts a chelating agent with a stereochemistry as shown below.

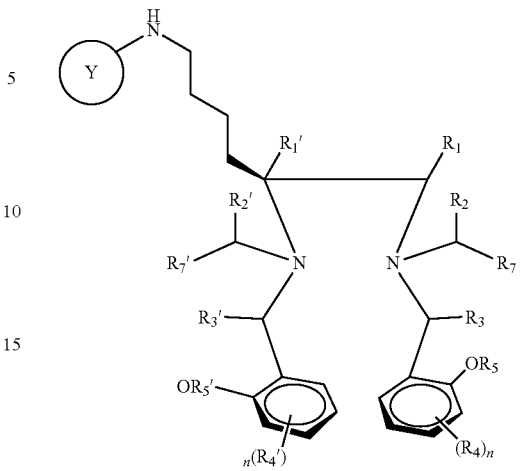
(XXXIX)

wherein $R_1$, $R_2$, $R_3$, $R_7$, $R'_1$, $R'_2$, $R'_3$ and $R'_7$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxyl group, a protected $C_1$-$C_3$ hydroxyalkyl group, a $C_1$-$C_3$ alkyl group or a hydrogen; and n is an integer between 0 and 4, $R_5$ and $R'_5$ are independently at each occurrence selected from the group consisting of $C_1$-$C_{30}$ aliphatic radicals, $C_3$-$C_{30}$ cycloaliphatic radicals, $C_2$-$C_{30}$ aromatic radicals and a hydrogen; with the proviso that at least one of $R_7$ and $R'_7$ is acidic groups; and Y comprises an antibody, a natural or synthetic peptide or amino acid, a protein, a nanoparticle, a micelle, a liposome, a poly(peptide), a peptidomimetic, an organic molecule, a sugar, an oligosaccharide a nucleic acid oligomer or polymer, a hydrophilic moiety. In one embodiment, Y is a polyethylene ether moiety.

In one embodiment of the contrast agent, the ligand has a structure XXXX:

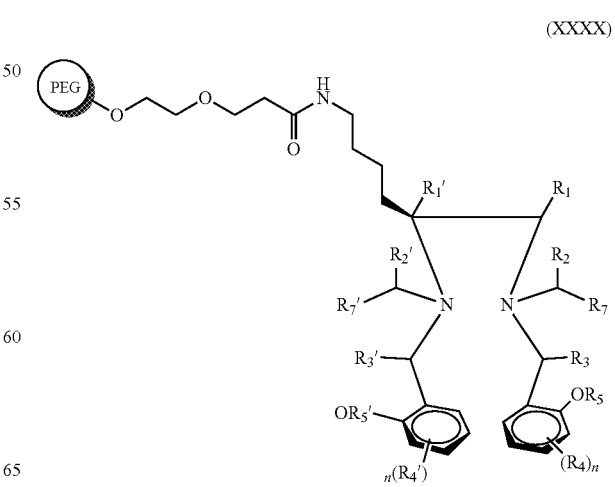
(XXXX)

wherein $R_1$, $R_2$, $R_3$, $R_7$, $R'_1$, $R'_2$, $R'_3$, and $R'_7$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxyl group, a protected $C_1$-$C_3$ hydroxyalkyl group, a $C_1$-$C_3$ alkyl group or a hydrogen; and n is an integer between 0 and 4; $R_5$ and $R'_5$ are independently at each occurrence selected from the group consisting of $C_1$-$C_{30}$ aliphatic radicals, $C_3$-$C_{30}$ cycloaliphatic radicals, $C_2$-$C_{30}$ aromatic radicals and a hydrogen; with the proviso that at least one of $R_7$ and $R'_7$ is acidic groups.

The chelating agents falling within the generic structure XXX are illustrated in Table 2 below:

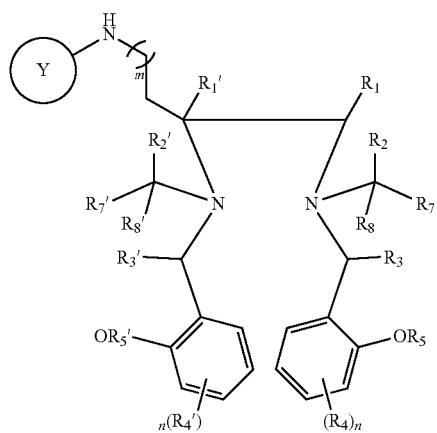

(XXX)

TABLE 2

Examples of chelating agents having generic structure XXX

| Entry | Structure |
|---|---|
| 1a | 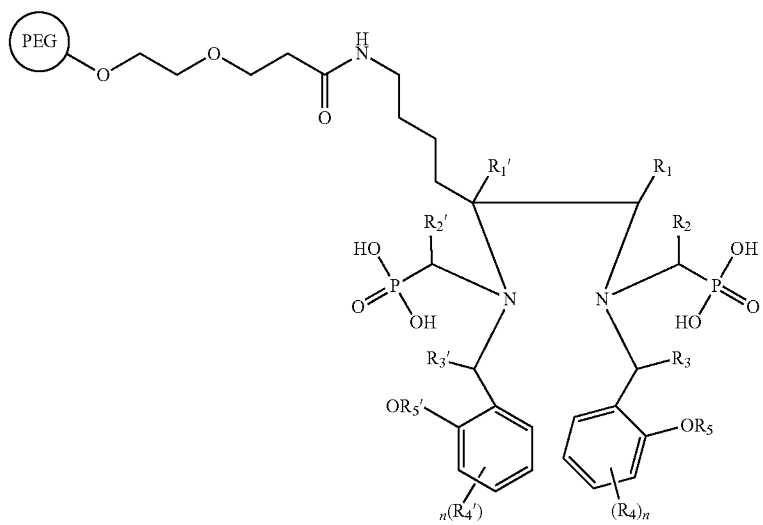 |
| 1b | 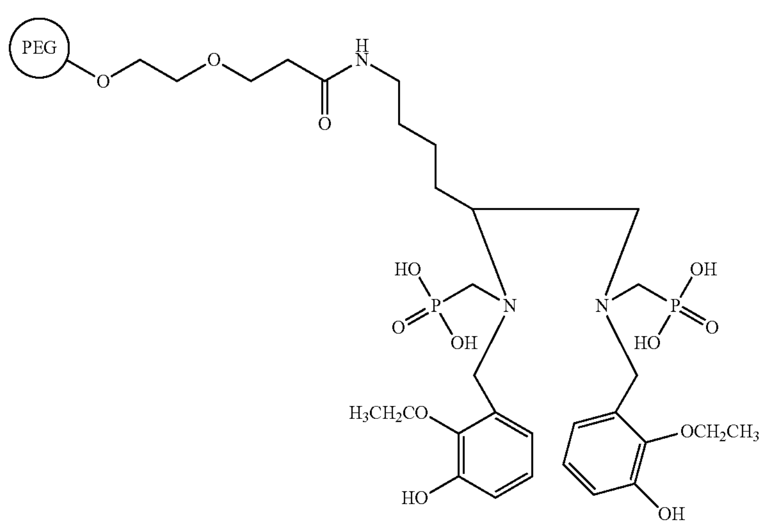 |

US 9,155,804 B2
TABLE 2-continued
Examples of chelating agents having generic structure XXX
| Entry | Structure |
|---|---|
| 1c | 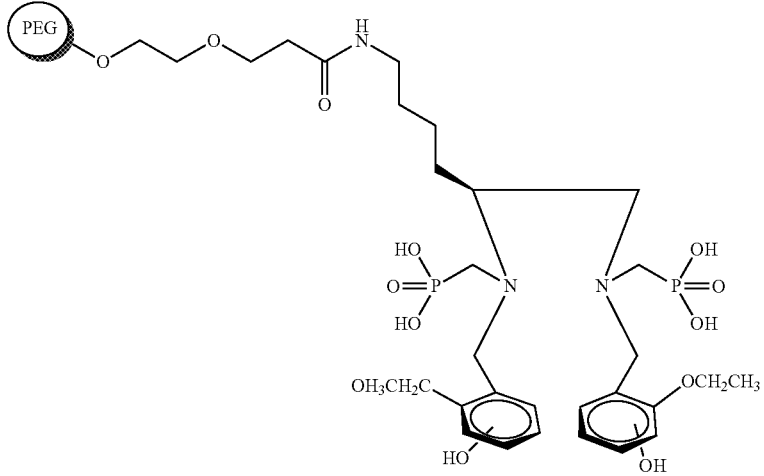 |
| 1d | 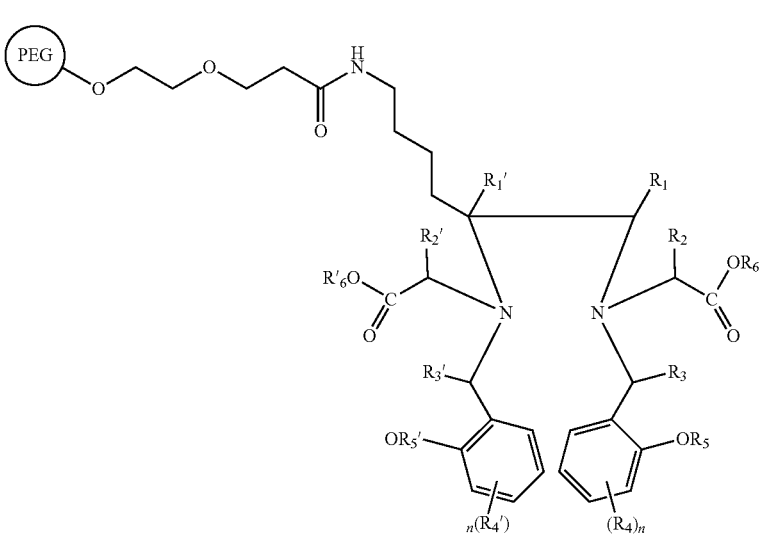 |
| 1e | 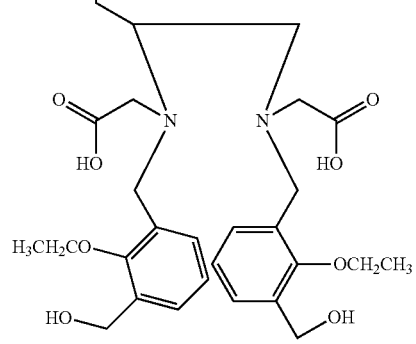 |

TABLE 2-continued

Examples of chelating agents having generic structure XXX

| Entry | Structure |
|---|---|
| 1f | 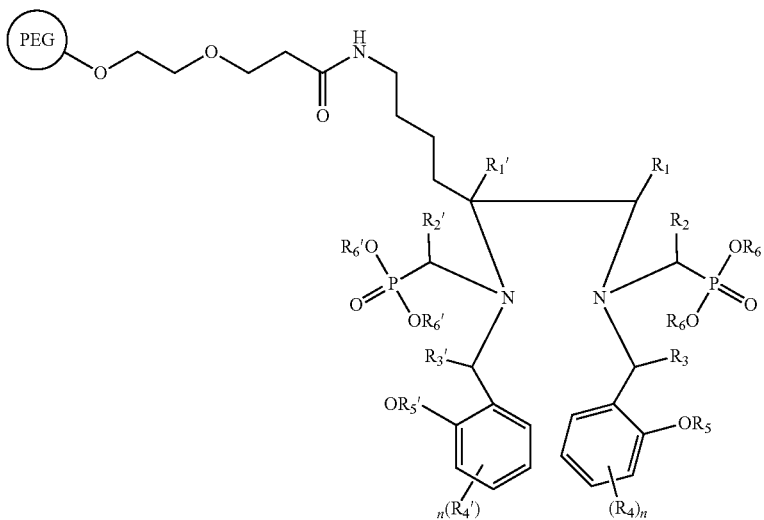 |
| 1g | 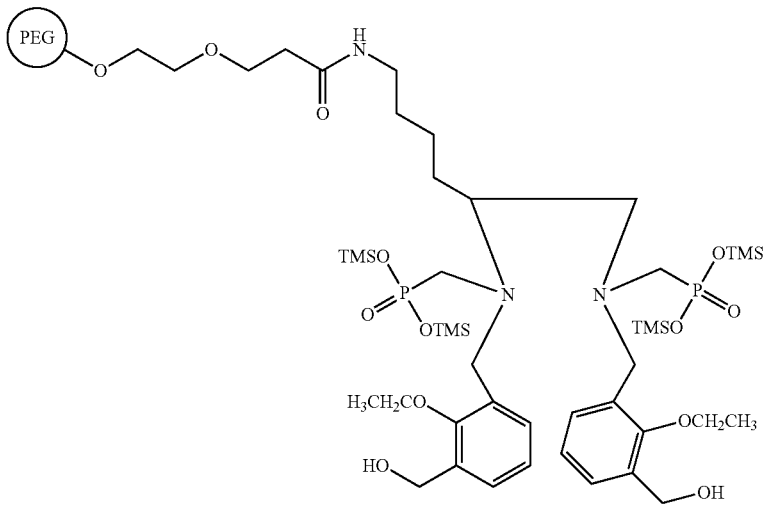 |

The term "idealized structure" is used herein to designate the structure indicated and additional structures which may include protonated and deprotonated forms of the metal chelating ligand having the idealized structure, in addition to any stereoisomeric forms. Those having ordinary skill in the art will appreciate that the individual metal chelating ligands provided by the present invention may comprise protonated and deprotonated forms of the metal chelating ligand, for example the idealized structure of metal chelating ligand of structure XXXI comprises one or more of the protonated and the deprotonated forms having structure XXXI(A)-XXXI(D)

XXXI(A)
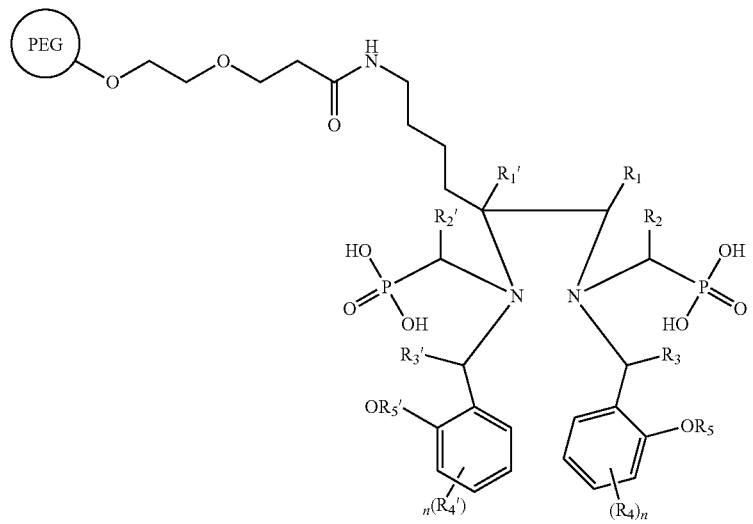
XXXI(B)
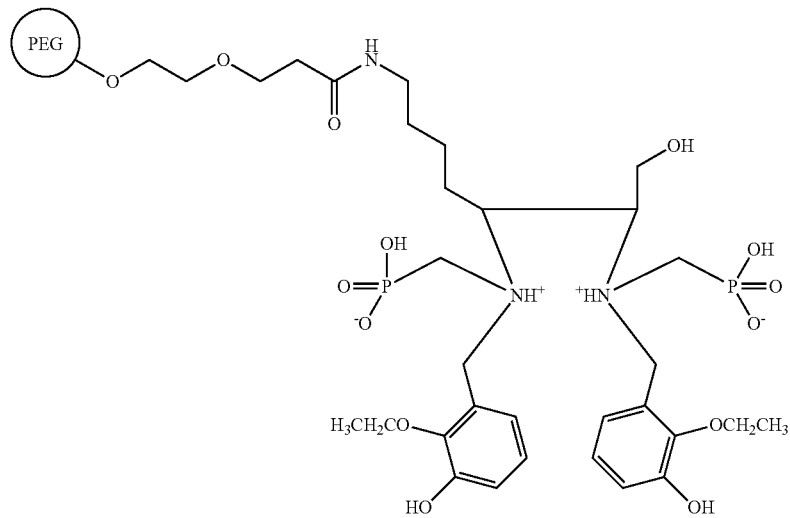
XXXI(C)
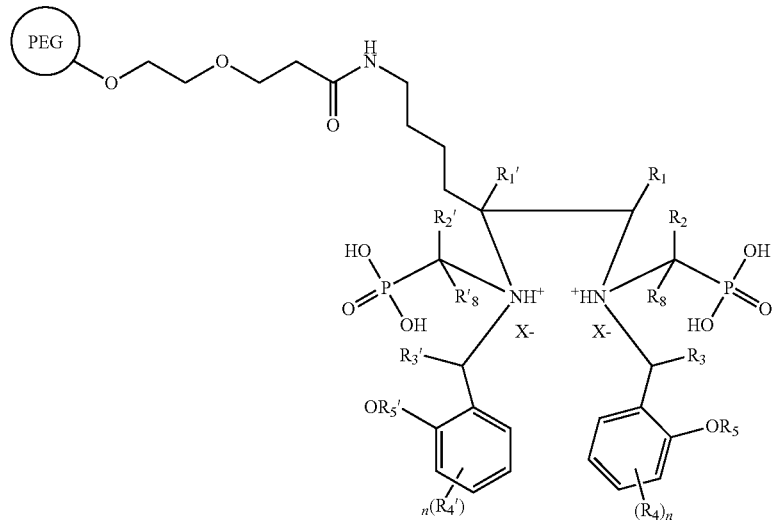

XXXI(D)

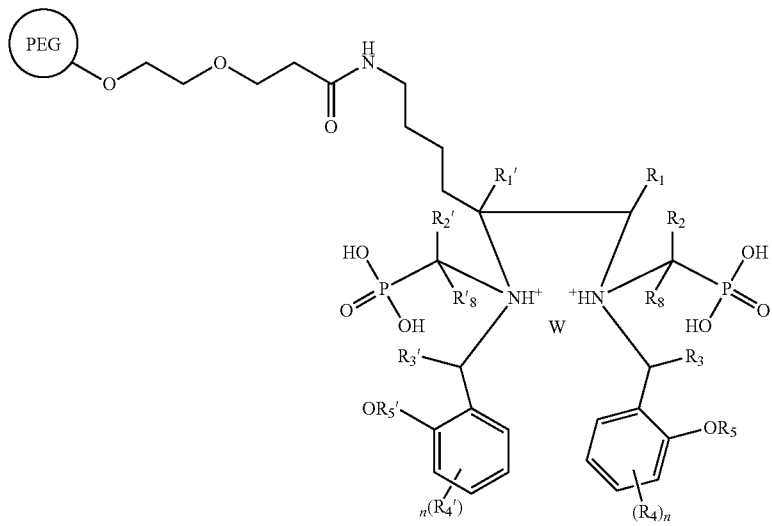

wherein W and X– are charge balancing counter ions. In one embodiment, the charge balancing counter ion X– may be an inorganic anion or an organic anion. Similarly, W may be an inorganic anion or an organic anion. Thus, in one embodiment, the charge balancing counter ion W is an inorganic anion. In another embodiment, the charge balancing counter ion W is an organic anion. Similarly, in one embodiment, the charge balancing counter ion X' is an inorganic anion. In another embodiment, the charge balancing counter ion X' is an organic anion. Those skilled in the art will appreciate that charge balancing counter ion X' includes monovalent anions such as chloride, bromide, iodide, bicarbonate, acetate, glycinate, ammonium succinate, and the like. Similarly, those skilled in the art will appreciate that charge balancing counter ions W include polyvalent anions such as carbonate, sulfate, succinate, malonate and the like.

Metal chelating ligands having structure XXXI(A) are further illustrated in Table 3 below in the idealized form.

TABLE 3

| Examples of metal chelating ligands having structure XXXI(A) | | | |
|---|---|---|---|
| Entry | Structure | W | X— |
| 3a | | — | — |

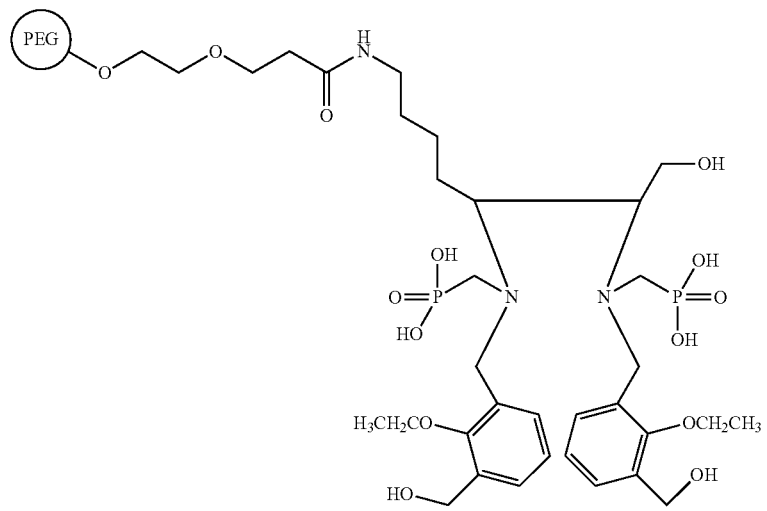

TABLE 3-continued

Examples of metal chelating ligands having structure XXXI(A)

| Entry | Structure | W | X— |
|---|---|---|---|
| 3b | 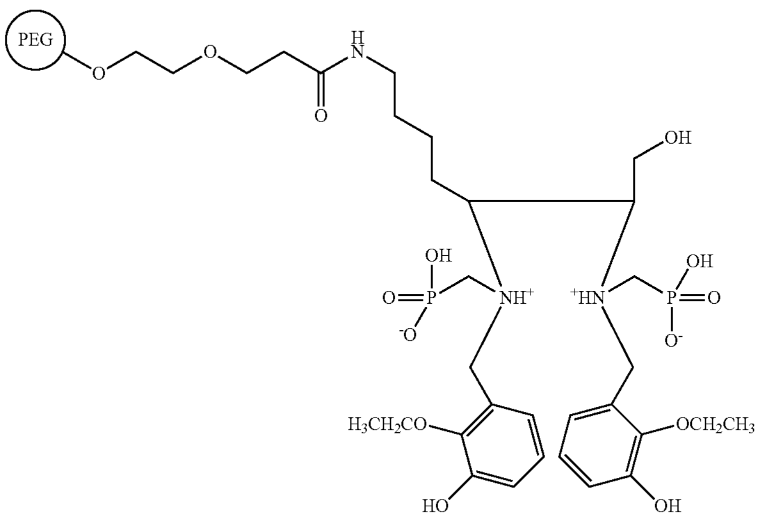 | — | — |
| 3c | 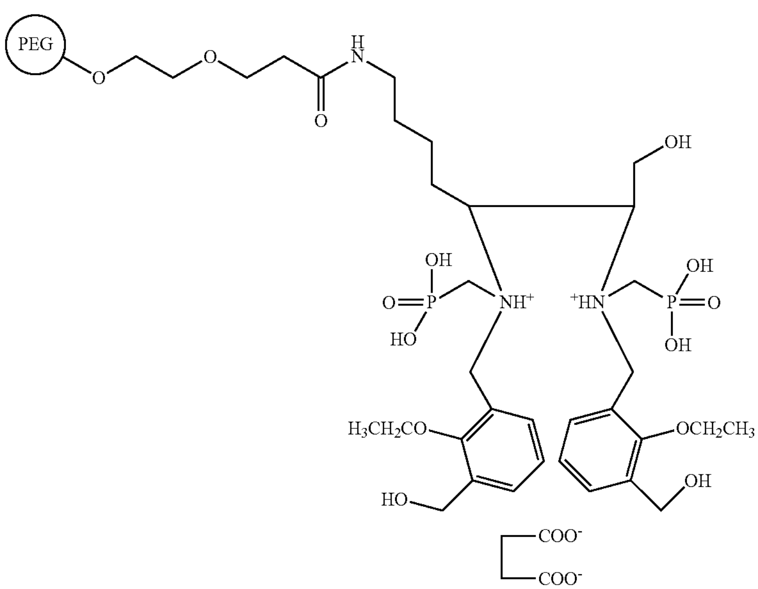 | $\begin{array}{c}\text{—CO}_2^\ominus\\ \text{—CO}_2^\ominus\end{array}$ (succinate) | — |

TABLE 3-continued

Examples of metal chelating ligands having structure XXXI(A)

| Entry | Structure | W | X— |
|---|---|---|---|
| 3d | 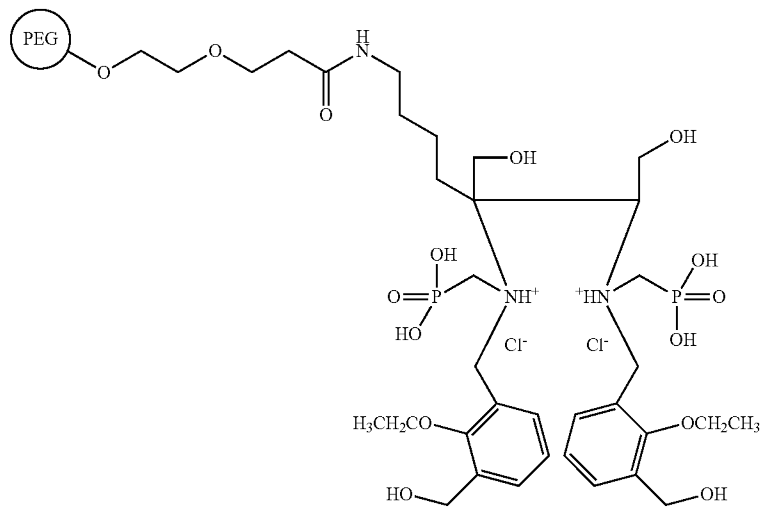 | — | Cl⁻ |

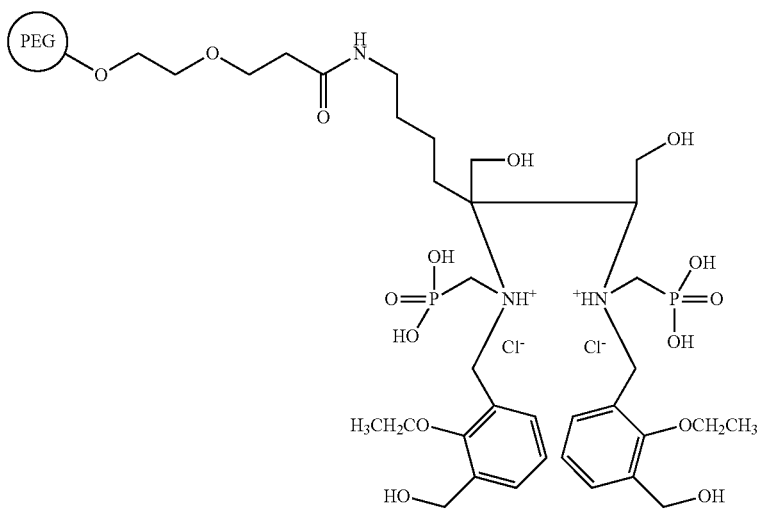

In an alternate embodiment, the present invention provides a metal chelating ligand having an idealized structure XXXXI (XXXXI)

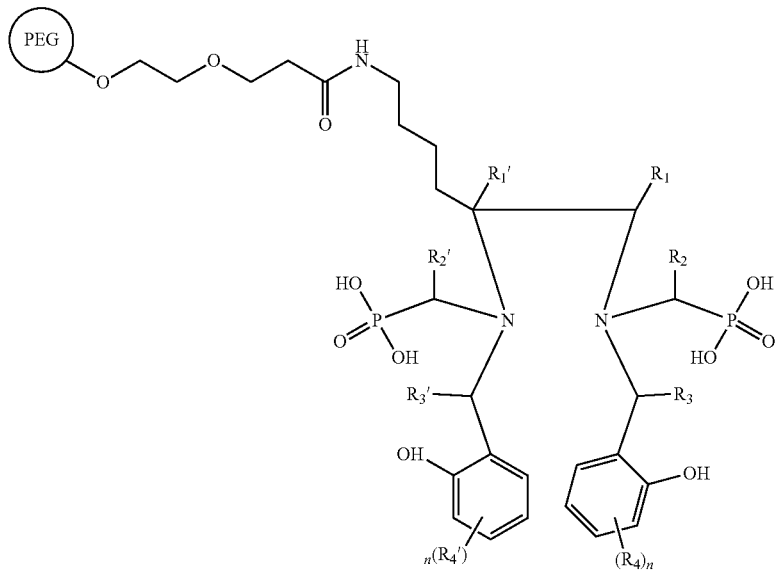

wherein $R_1$, $R_1'$, $R_2$, $R_2'$, $R_3$, and $R_3'$ are independently at each occurrence hydrogen, a protected $C_1$-$C_3$ hydroxyalkyl group, or a $C_1$-$C_3$ alkyl group; are hydrogen; $R_4$ and $R_4'$ are independently at each occurrence a protected hydroxy group, a protected $C_1$-$C_3$ hydroxyalkyl group, or a $C_1$-$C_3$ alkyl group; n is an integer between 0 and 4, and PEG is a polyethylene ether moiety.

Metal chelating ligands having structure XXXXI are further illustrated in Table 4 below in the idealized form.

TABLE 4

Examples of Metal Chelating Ligands Having Structure XXXXI

| Entry | Structure | W | X' |
|---|---|---|---|
| 4a | 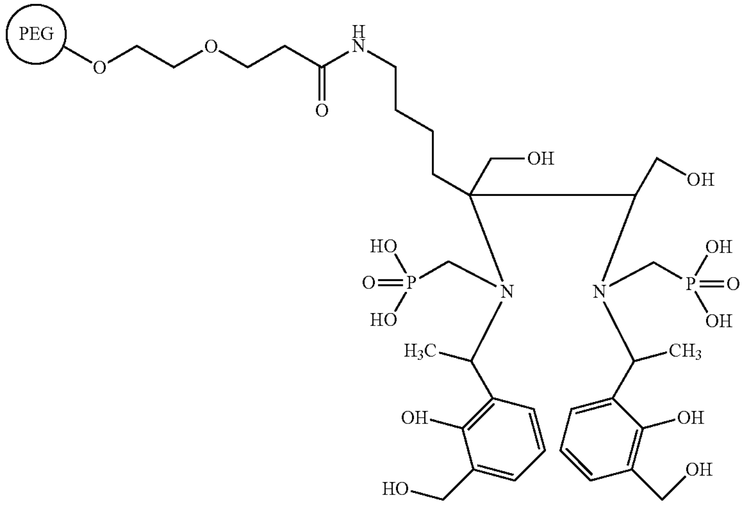 [SMILES: COCCOCCC(=O)NCCCCC(CO)(C(CO)N(CP(=O)(O)O)C(C)c1cccc(CO)c1O)N(CP(=O)(O)O)C(C)c1cccc(CO)c1O] | — | — |
| 4b | 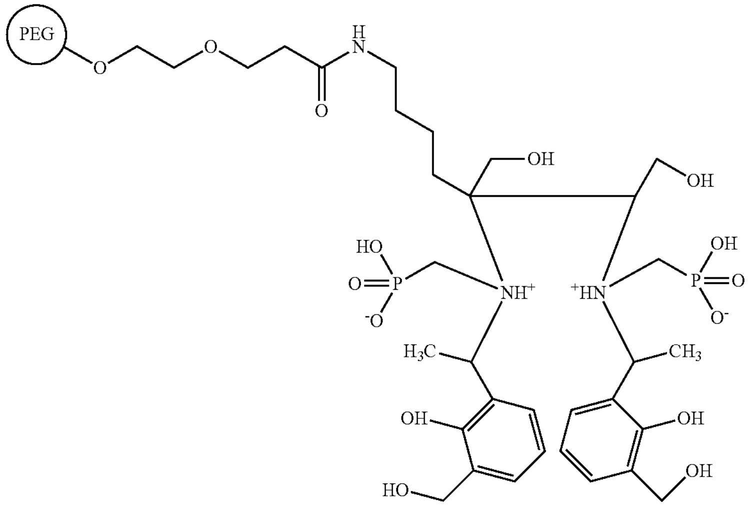 | — | — |
| 4c | 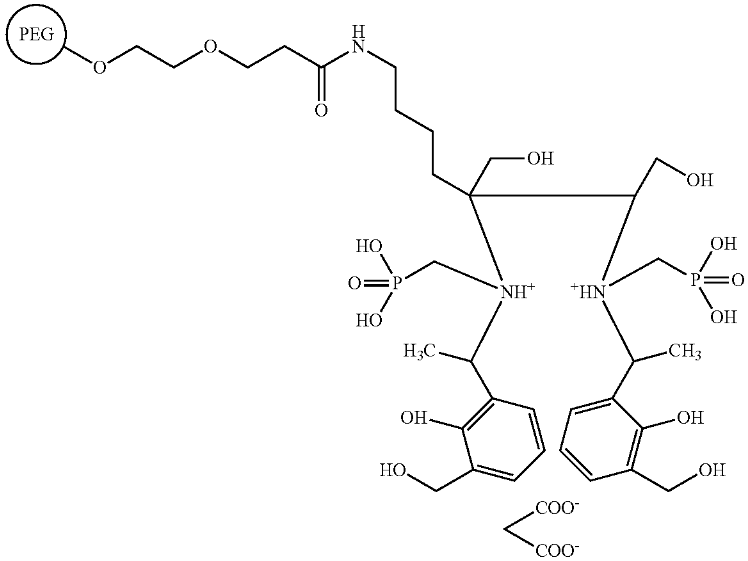 | (malonate) | |

TABLE 4-continued
Examples of Metal Chelating Ligands Having Structure XXXXI
| Entry | Structure | W | X' |
|---|---|---|---|
| 4d | 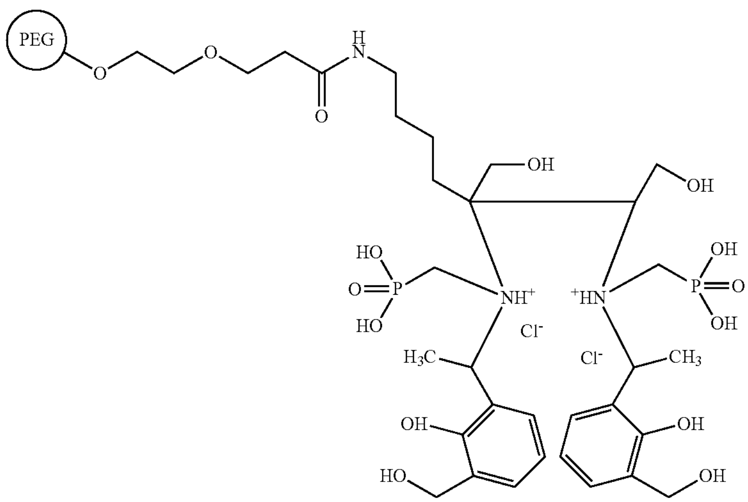 [SMILES: COCCOCCC(=O)NCCCCC(CO)(C(CO)[NH+](CP(=O)(O)O)C(C)c1cccc(CO)c1O)[NH+](CP(=O)(O)O)C(C)c1cccc(CO)c1O ; [Cl-] ; [Cl-]] | — | Cl⁻ |
The metal chelating ligands having stereoisomeric structure of XXXXI are illustrated in Table 5 below.
TABLE 5
Examples of Metal Chelating Ligands Having stereoisomeric structures of XXXXI
| Entry | Structure | W | X' |
|---|---|---|---|
| 5a | 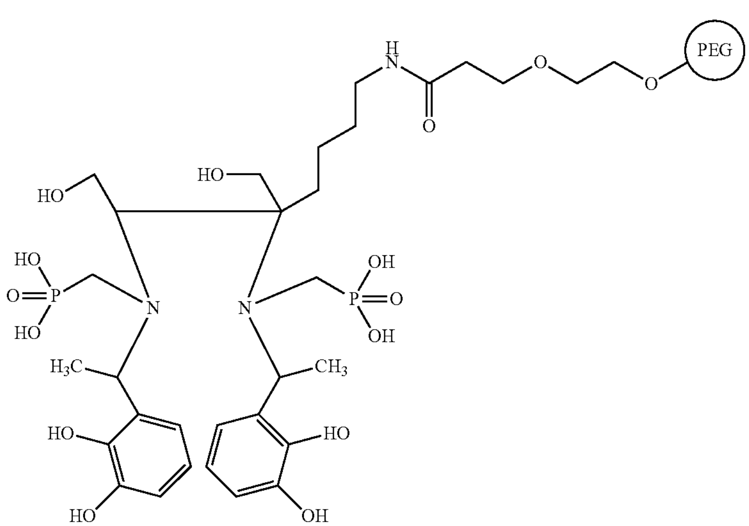 [SMILES: COCCOCCC(=O)NCCCCC(CO)(C(CO)N(CP(=O)(O)O)C(C)c1cccc(O)c1O)N(CP(=O)(O)O)C(C)c1cccc(O)c1O] | — | — |
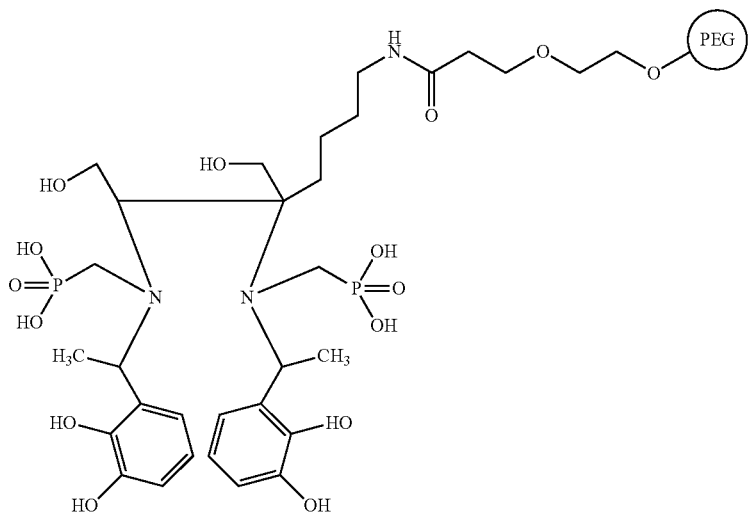

TABLE 5-continued
Examples of Metal Chelating Ligands Having stereoisomeric structures of XXXXI
| Entry | Structure | W | X' |
|---|---|---|---|
| 5b | 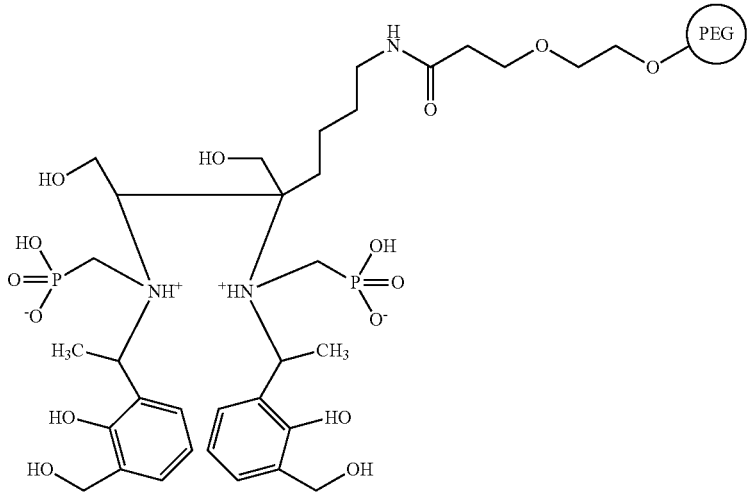 | — | — |
| 5c | 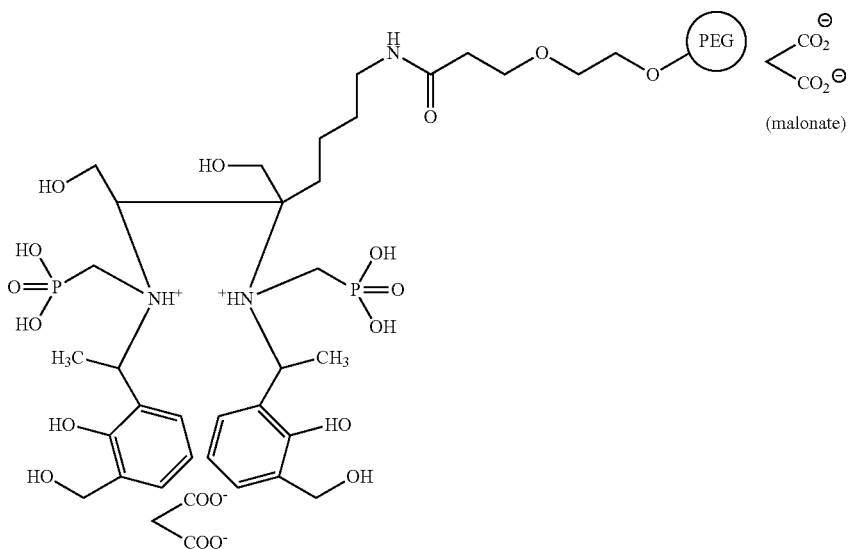 (malonate) | | |
| 5d | 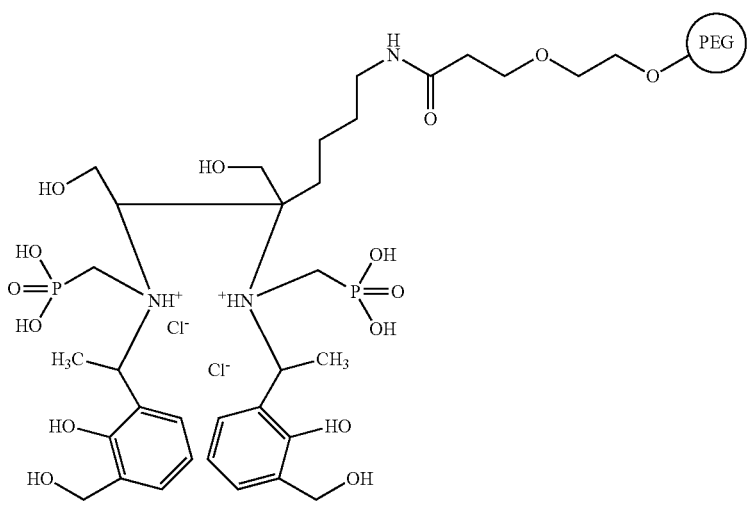 [SMILES: COCCOCCC(=O)NCCCCC(CO)(C(CO)[NH+](CP(=O)(O)O)C(C)c1cccc(CO)c1O)[NH+](CP(=O)(O)O)C(C)c1cccc(CO)c1O ; [Cl-] ; [Cl-]] | — | Cl$^-$ |

The metal chelating ligands form coordinate complexes with a variety of metals. In one embodiment, the metal chelating ligands form complexes with transition metals. In a particular embodiment, the transition metal is iron.

Those skilled in the art will appreciate that the iron chelate compositions provided by the present invention may comprise a principal component enantiomer, a minor component enantiomer, and additional diastereomeric iron chelate components. In one embodiment, the present invention provides an iron chelate composition comprising a principal component enantiomer and related diastereomers. In an alternate embodiment, the present invention provides an iron chelate composition having no principal component enantiomer and which is a diastereomeric mixture.

In one or more embodiments, a contrast agent composition suitable for injection into a mammalian subject comprising a pharmaceutically acceptable carrier or excipient and a metal-complex having a structure (XXXXII)

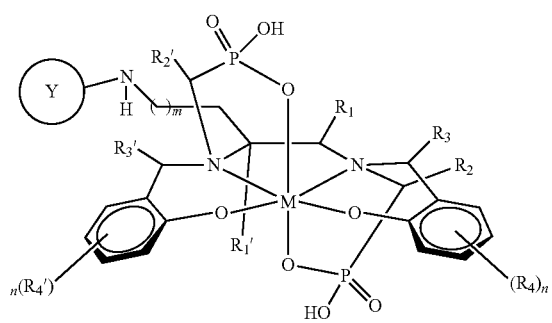

(XXXXII)

wherein $R_1, R_2, R_3, R'_1, R'_2$, and $R'_3$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxy group, a protected $C_1$-$C_3$ hydroxyalkyl group, or a $C_1$-$C_3$ alkyl group; and n is an integer between 0 and 4; $R_5$ and $R'_5$ are independently at each occurrence a hydrogen or a protecting group selected from the group consisting of $C_1$-$C_{30}$ aliphatic radicals, $C_3$-$C_{30}$ cycloaliphatic radicals, and $C_2$-$C_{30}$ aromatic radicals; with the proviso that at least one of $R_7$ and $R'_7$ is protected acidic groups; m is an integer between 0 and 10; and M is a metal, and Y comprises an antibody, a natural or synthetic peptide or amino acid, a protein, a nanoparticle, a micelle, a liposome, a poly(peptide), a peptidomimetic, an organic molecule, a sugar, an oligosaccharide a nucleic acid oligomer or polymer, or a hydrophilic moiety.

In one or more embodiments, a contrast agent composition comprises a metal complex of structure (XXXXIII)

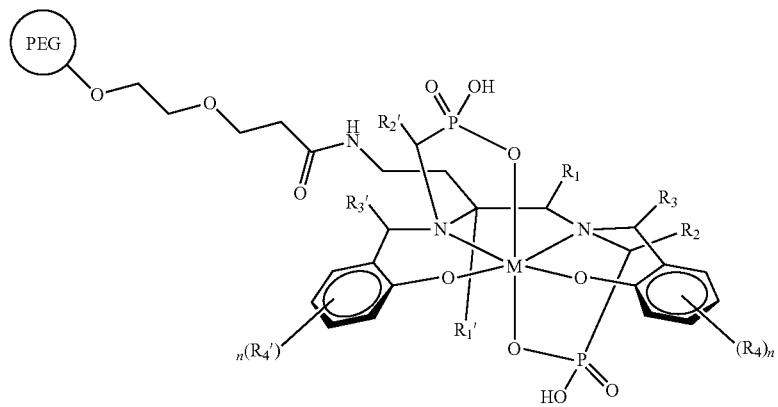

(XXXXIII)

wherein $R_1, R_2, R_3, R_8, R'_1, R'_2, R'_3$ and $R_8'$ are independently at each occurrence hydrogen, a protected $C_1$-$C_3$ hydroxyalkyl group, or a $C_1$-$C_3$ alkyl group; $R_4$ and $R'_4$ are independently at each occurrence a hydrogen, a hydroxyl, a protected hydroxy group, a protected $C_1$-$C_3$ hydroxyalkyl group, or a $C_1$-$C_3$ alkyl group; and n is an integer between 0 and 4; $R_5$ and $R'_5$ are independently at each occurrence a protecting group selected from the group consisting of $C_1$-$C_{30}$ aliphatic radicals, $C_3$-$C_{30}$ cycloaliphatic radicals, and $C_2$-$C_{30}$ aromatic radicals; with the proviso that at least one of $R_7$ and $R'_7$ is protected acidic groups; and M is a metal, and PEG is a polyethylene ether moiety.

In some embodiments, the metal M of the metal-chelate composition is selected from iron (Fe), manganese (Mn), gallium (Ga), indium (In), gadolinium (Gd), tungsten (W), tantalum (Ta), or boron (B). In one embodiment, the metal complex of structure (XV) comprises iron (Fe) as the metal ion.

In some embodiments, a contrast agent composition comprising a metal chelate complex comprising iron as the metal, and the complex has a structure (XXXXIV):

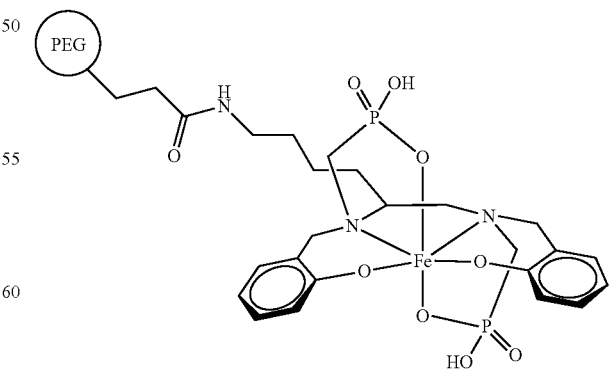

(XXXXIV)

In some embodiments, a contrast agent composition comprising a metal chelate complex comprising iron as the metal, and the complex has a structure (XXXXIV-A)

(XXXXIV-A)

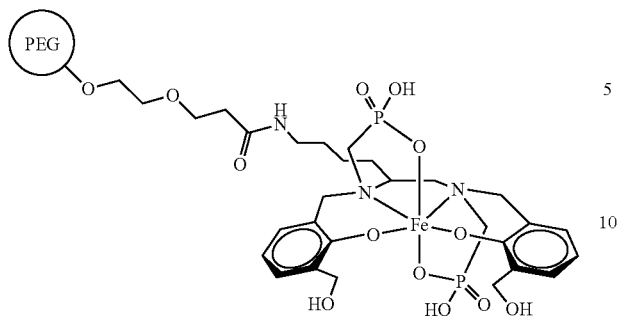

In another embodiment, the present invention provides a contrast enhancement agent comprising an iron chelate having structure XXXXV (XXXXV)

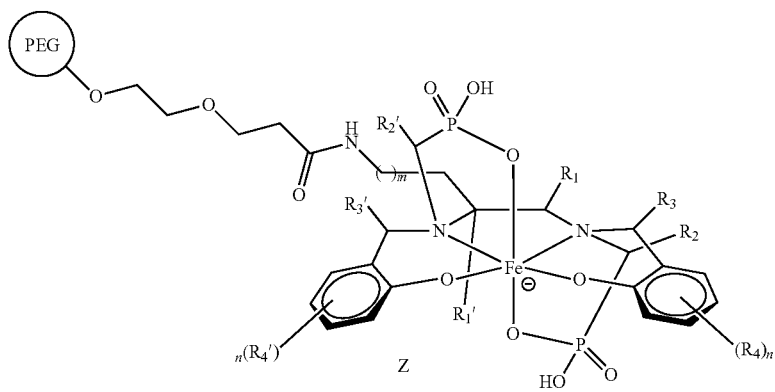

wherein $R_1$, $R_2$, $R_3$, $R_8$, $R'_1$, $R'_2$, $R'_3$ and $R'_8$ are independently at each occurrence hydrogen, a protected $C_1$-$C_3$ hydroxyalkyl group, or a $C_1$-$C_3$ alkyl group; $R_4$ and $R'_4$ are independently at each occurrence a protected hydroxy group, a protected $C_1$-$C_3$ hydroxyalkyl group, or a $C_1$-$C_3$ alkyl group; and n is an integer between 0 and 4; $R_5$ and $R'_5$ are independently at each occurrence a protecting group selected from the group consisting of $C_1$-$C_{30}$ aliphatic radicals, $C_3$-$C_{30}$ cycloaliphatic radicals, and $C_2$-$C_{30}$ aromatic radicals; with the proviso that at least one of $R_7$ and $R'_7$ is protected acidic groups; PEG is a polyethylene ether moiety, and wherein Z is a charge balancing counterion.

A composition of a metal chelate comprising a compound comprising an iron chelate and falling within generic structure XXXXV are illustrated in Table 6 below.

TABLE 6

Examples of Iron Chelate Contrast Enhancement Agents Having Structure XXXXV

| Entry | Structure | Variable Q Defined As |
|---|---|---|
| 6a | ![structure] | $Na^+$ |

TABLE 6-continued
Examples of Iron Chelate Contrast Enhancement Agents Having Structure XXXXV
| Entry | Structure | Variable Q Defined As |
|---|---|---|
| 6b | 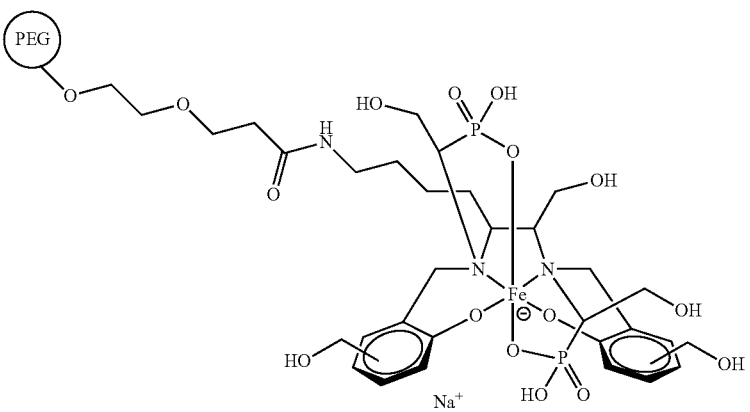 | Na⁺ |
| 6c | 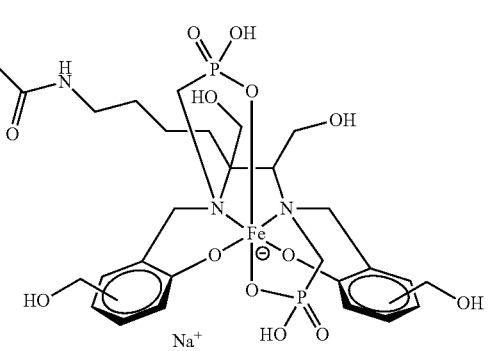 | Na⁺ |
| 6d | 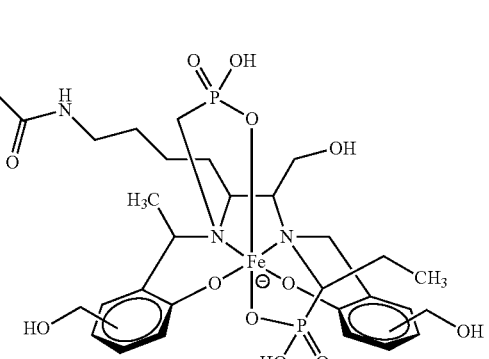 | ½ Ca⁺⁺ |

TABLE 6-continued

Examples of Iron Chelate Contrast Enhancement Agents Having Structure XXXXV

| Entry | Structure | Variable Q Defined As |
|---|---|---|
| 6e | 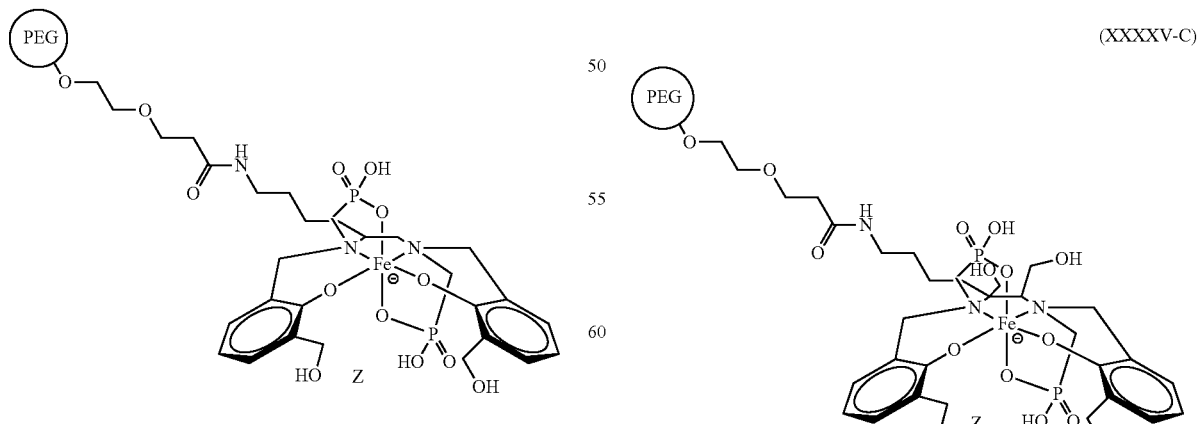 | $^+HN(C_2H_5)_3$ |

The charge balancing counter ion Z may be an organic cation or an inorganic cation. Thus, in one embodiment, the charge balancing counterion Z is an inorganic cation. Non-limiting examples of inorganic cations include alkali metal cations, alkaline earth metal cations, transition metal cations, and inorganic ammonium cations ($NH_4^+$). In another embodiment, the charge balancing counterion Z is an organic cation, for example an organic ammonium cation, an organic phosphonium cation, an organic sulfonium cation, or a mixture thereof. In one embodiment, the charge balancing counterion is the ammonium salt of an aminosugar such as the 2-(N,N,N-trimethylammonium)-2-deoxyglucose. In one embodiment, the charge balancing counterion is the protonated form of N-methyl glucamine.

In one embodiment, the composition includes an iron chelate having structure XXXXV (XXXXV-A)

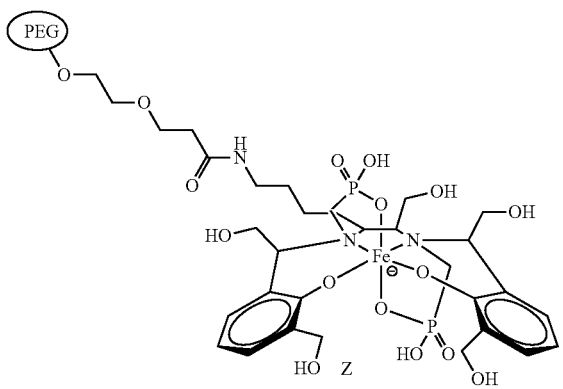

wherein Z is a charge balancing counterion.

In another embodiment, the composition includes an iron chelate having structure XXXXV-B (XXXXV-B)

wherein Z is a charge balancing counterion.

In another embodiment, the contrast enhancing agent includes an iron chelate having structure XXXXV-C (XXXXV-C)

wherein Z is a charge balancing counterion.

In yet another embodiment, the contrast enhancing agent includes an iron chelate having structure XXXXV-D

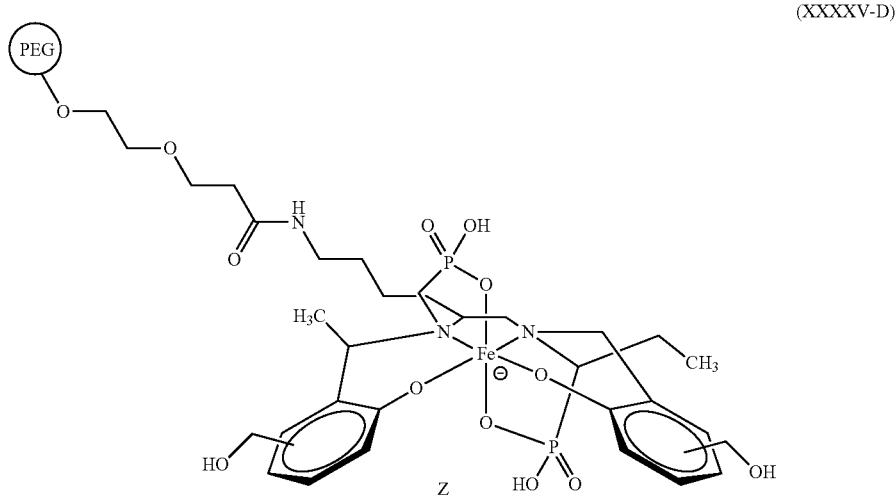

(XXXXV-D)

wherein Z is a charge balancing counterion.

In another embodiment, the contrast enhancing agent includes an iron chelate having structure XXXXV-E

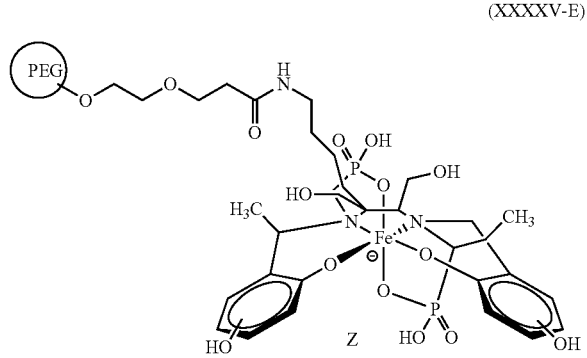

(XXXXV-E)

wherein Z is a charge balancing counterion.

In another embodiment, the contrast enhancing agent includes an iron chelate having structure XXXXV-F (XXXXV-F)

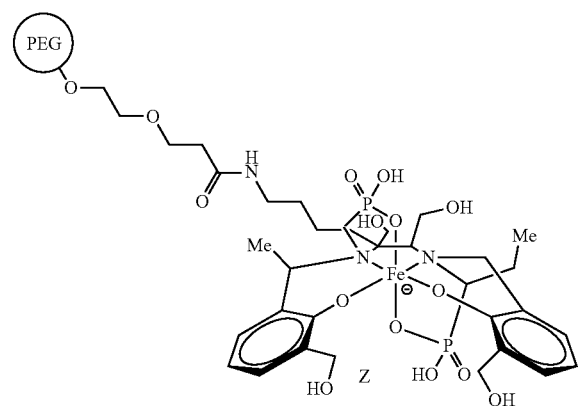

wherein Z is a charge balancing counterion.

In one embodiment, the present invention provides a medical formulation comprising a composition of a contrast enhancement agent comprising a ligand having structure XXX. In another embodiment, the medical formulations provided by the present invention comprise at least one structure selected from structures XXXI-XXXXI.

In some other embodiments, the present invention provides a medical formulation comprising a composition of a contrast enhancement agent comprising a metal-chelate complex having structure XXXXII. In yet another embodiment, the present invention provides a medical formulation comprising the contrast enhancement agent comprising an iron-chelate complex having structure XXXXIII. In another embodiment, the medical formulations provided by the present invention comprise at least one metal-chelate having structure selected from structures XXXXIV or XXXXV.

The contrast enhancement agents provided by the present invention are suitable for use as imaging agents for magnetic resonance (MR) screening of human patients for various pathological conditions. As will be appreciated by those of ordinary skill in the art, MR imaging has become a medical imaging technique of critical importance to human health. In one embodiment, the present invention provides a method for increasing the emitted signal, and thus obtaining in vivo differentiation of tissues in an organism by administering a contrast enhancement agent of the present invention to a living subject and conducting magnetic resonance imaging of the subject.

In one or more embodiments of the contrast agents, the metal-chelate is characterized by an average hydrodynamic diameter ($D_H$) as determined by dynamic light scattering in 150 mM NaCl water or PBS in a range from about 2 nm to about 500 nm. The metal-chelate complex is characterized by its ability to form a stable aqueous colloidal suspension that exhibits no substantial change in hydrodynamic diameter ($D_H$) as determined by dynamic light scattering in 150 mM aqueous NaCl or PBS after tangential flow filtration and storage for one week at room temperature.

In one embodiment, the contrast enhancement agent according to the present invention may be used for imaging the circulatory system, the genitourinary system, hepatobiliary system, central nervous system, for imaging tumors, abscesses and the like. In another embodiment, the contrast enhancement agent of the present invention may also be useful to improve lesion detectability by MR enhancement of either the lesion or adjacent normal structures.

The contrast enhancement agent may be administered by any suitable method for introducing a contrast enhancement agent to the tissue area of interest. The medical formulation containing the contrast enhancement agent is desirably sterile and is typically administered intravenously and may contain various pharmaceutically acceptable agents, which promote the dispersal of the MR imaging agent. In one embodiment, the medical formulation provided by the present invention is an aqueous solution. In one embodiment, the MR imagining agent may be administered to a patient in an aqueous formulation comprising ethanol and the contrast enhancement agent. In an alternate embodiment, the MR imaging agent may be administered to a patient as an aqueous formulation comprising dextrose and the contrast enhancement agent. In yet another embodiment, the MR imagining agent may be administered to a patient as an aqueous formulation comprising saline and the contrast enhancement agent.

In addition to being useful as MR imaging agents and as probes for determining the suitability of a given iron chelate compound for use as a MR imaging agent, the contrast enhancement agents provided by the present invention may also, in certain embodiments, possess therapeutic utility in the treatment of one or more pathological conditions in humans and/or animals. Thus, in one embodiment, the present invention provides a contrast enhancement agent comprising a metal-chelate having structure XXXX, which is useful in treating a pathological condition in a patient. In an alternate embodiment, the present invention provides a contrast enhancement agent comprising a metal-chelate having structure XXXXI, which is useful in treating a pathological condition in a patient.

Those skilled in the art will appreciate that iron chelate complexes falling within the scope of generic structure XXXX may under a variety of conditions form salts, which are useful as MR imaging agents, probes for the discovery and development of imaging agents, and/or as therapeutic agents. Thus, the present invention provides a host of novel and useful iron chelate compounds and their salts.

In one embodiment, the contrast enhancement agent provided by the present invention includes an iron chelate wherein the iron is paramagnetic. Contrast enhancement agents provided by the present invention comprising a paramagnetic iron center are believed to be more readily excreted by human patients and by animals and as such are more rapidly and completely cleared from the patient following the magnetic resonance imaging procedure. In addition, the contrast enhancement agents provided by the present invention may enable the administration of lower levels of the contrast enhancement agent to the patient relative to known contrast enhancement agents without sacrificing image quality. Thus, in one embodiment, useful MR contrast enhancement using the contrast enhancement agent of the present invention is achieved at lower dosage level in comparison with known MR contrast agents. In an alternate embodiment, the contrast enhancement agents provided by the present invention may administered to a patient at a higher dosage level in comparison with known MR contrast agents in order to achieve a particular result. Higher dosages of the contrast enhancement agents of the present invention may be acceptable in part because of the enhanced safety of such iron based contrast enhancement agents, and improved clearance of the contrast enhancement agent from the patient following the imaging procedure. In one embodiment, contrast enhancement agent is administered in a dosage amount corresponding to from about 0.001 to about 5 millimoles per kilogram weight of the patient. As will be appreciated by those of ordinary skill in the art, contrast enhancement agents provided by the present invention may be selected and/or further modified to optimize the residence time of the contrast enhancement agent in the patient, depending on the length of the imaging time required.

When used in diagnostic imaging, particularly of mammalian subjects and more particularly of human subjects, the modified hydrophilic metal-chelate complexes are typically taken up in a pharmaceutically acceptable carrier which may or may not comprise one or more excipients. If the administration is to be by injection, particularly parenteral injection, the carrier is typically an aqueous medium that has been rendered isotonic by the addition of about 150 mM of NaCl, 5% dextrose or combinations thereof. It typically also has the physiological pH of between about 7.3 and 7.4. The administration may be intramuscular (IM), subcutaneous (SQ) or most commonly intravenous (IV). However, the administration may also be via implantation of a depot that then slowly releases the metal chelate to the subject's blood or tissue.

The contrast enhancement agent of the present invention may be prepared by a variety of methods including those provided in the experimental section of this disclosure. For example, stoichiometric amounts of the metal ion and the metal chelating ligand may be admixed in a solution with an appropriate adjustment of pH, if necessary. The contrast enhancement agent may be isolated by conventional methods such as crystallization, chromatography, and the like, and admixed with conventional pharmaceutical carriers suitable for pharmaceutical administration.

Alternatively, the administration may be by ingestion for imaging of the GI tract or for oral delivery of a therapeutic iron dose or, by inhalation for imaging of the lungs and airways. The administration to human subjects, particularly intravenous administration, requires that the modified hydrophilic metal-chelate complex, non-toxic in the amounts used and free of any infective agents such as bacteria and viruses and also free of any pyrogens. Thus, these complexes should be stable to the necessary purification procedures and not suffer degradation in their hydrophilicity.

These metal-chelates may be delivered to the site of administration as a stable aqueous solution with the proper osmolality and pH, as a concentrated aqueous solution suitable for dilution and adjustment or as a powder, such as obtained by lyophilization, suitable for reconstitution.

The present disclosure, therefore, further relates to methods for diagnostic imaging using a contrast agent. The method comprises subjecting an individual to the diagnostic imaging, wherein the subject is administered with a contrast agent comprising a metal-complex and a pharmaceutically acceptable carrier or excipient, and wherein the metal-complex has a structure XXXX, as disclosed herein. As the method comprises subjecting an individual to whom the contrast agent composition has been administered to imaging, for example by magnetic resonance (MR), wherein the composition administered to the subject comprises metal-chelate comprising PEG conjugate. The PEG, in some embodiments, has a molecular weight greater than about 2,000 daltons and less than or equal to about 30,000 daltons.

Initial efforts were made to generate a bifunctional iron-chelate from diamino propionic acid. Different conditions were used to alkylate the bis-(hydroxyl benzyl)ethylene diamino propionate intermediate, however, the monoalkylated moiety, rather than the desired dialkylated-chelate was obtained. In the case of unprotected phenols, forcing conditions lead to formation of the tri and tetra substituted product.

The synthesis scheme and various efforts made under different conditions are described below (Scheme and Table 7).

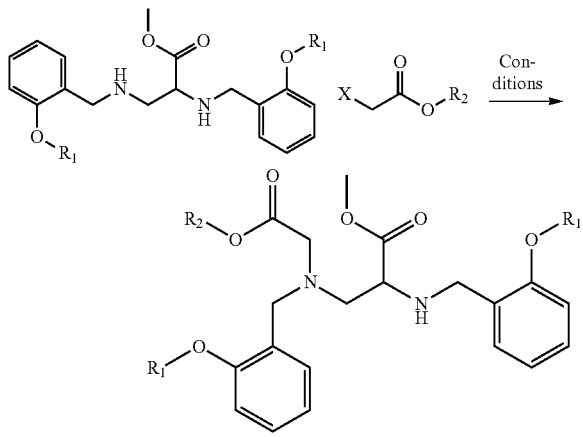

TABLE 7

Previous unsuccessful approaches for making bifunctional iron-chelate under various conditions

| R1 | R2  | X   | Conditions                              | Result                       |
|----|-----|-----|-----------------------------------------|------------------------------|
| H  | H   | Br  | Ambient 12 h, Hunig's base              | Monosubstitution             |
| H  | H   | Br  | Reflux 12 h, Hunig's base               | R1 alkylation to trisubstituted |
| H  | H   | I   | Ambient 12 h, Hunig's base              | Monosubstitution             |
| H  | H   | I   | Reflux 12 h, Hunig's base               | R1 alkylation to trisubstituted |
| Me | H   | Br  | Reflux 12 h, Hunig's base, KI           | Monosubstitution             |
| Me | H   | I   | Reflux 12 h, Hunig's base               | Monosubstitution             |
| Me | tBu | Br  | Reflux 12 h, Hunig's base, KI           | Monosubstitution             |
| Me | tBu | I   | Reflux 12 h, Hunig's base               | Monosubstitution             |
| Me | tBu | OTf | −20° C. to ambient, 12 h, Hunig's base  | Monosubstitution             |

An embodiment of a process for making a metal chelate, comprises contacting a metal ion or chelate with a ligand of structure (XXX) to form a mixture; heating the mixture at about 35 to 100° C. and adjusting the pH to a neutral pH condition; wherein the structure (XXX) is

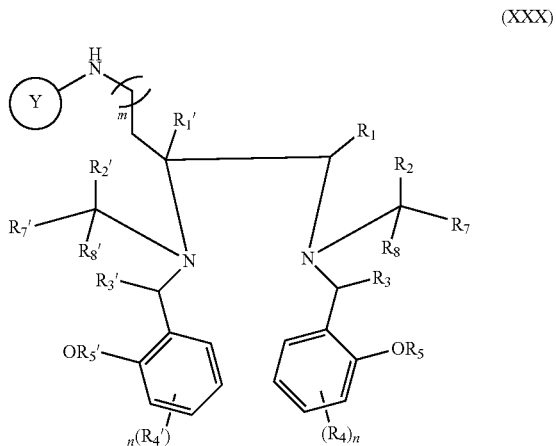

(XXX)

wherein R1, R2, R3, R7, R8, R'1, R'2, R'3, R'7 and R'8 are independently at each occurrence hydrogen, a protected C1-C3 hydroxyalkyl group, or a C1-C3 alkyl group; R4 and R'4 are independently at each occurrence a hydrogen or a protected hydroxyl group, a protected C1-C3 hydroxyalkyl group, a C1-C3 alkyl group; and n is an integer between 0 and 4; R5 and R'5 are independently at each occurrence a hydrogen or a protecting group selected from the group consisting of C1-C30 aliphatic radicals, C3-C30 cycloaliphatic radicals, C2-C30 aromatic radicals and m is an integer between 0 and 10; with the proviso that at least one of R7 and R'7 is an acidic group or protected acidic group; and Y comprises an antibody, a natural peptide, a synthetic peptide, an amino acid, a polypeptide, a protein, a nanoparticle, a micelle, a liposome, a peptidomimetic, an organic molecule, a sugar, an oligosaccharide a nucleic acid oligomer, polymer, or a hydrophilic moiety.

In another embodiment of a process for making a metal chelate, a metal ion or a metal-chelate is contacting with a ligand of structure (XXX) to form a mixture. In one embodiment, the mixture is heated at about 55° C. In some embodiments, the pH of the mixture is adjusted to a neutral pH to a higher pH condition.

Figure 1:
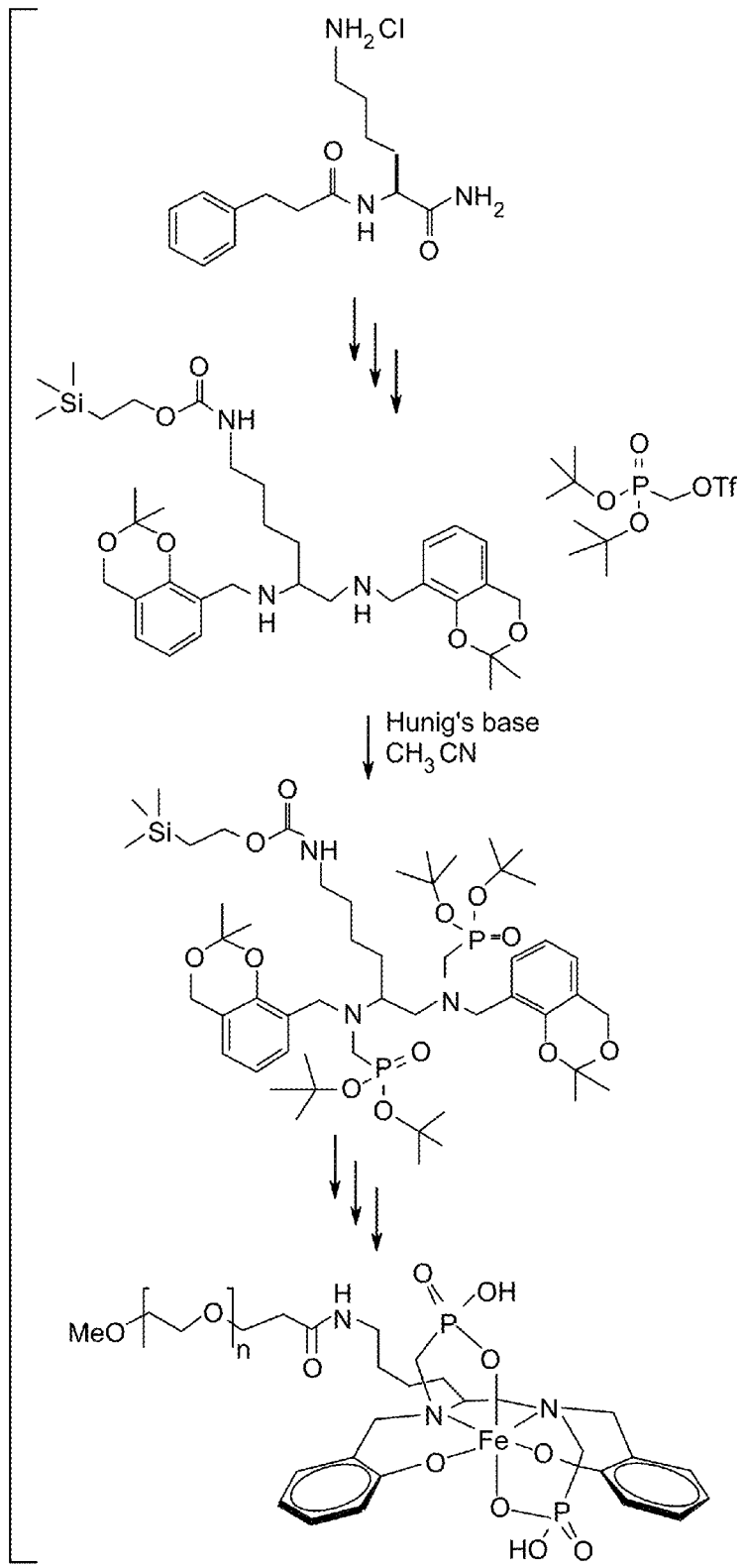
FIG. 1 is an example of synthesis scheme of a bifunctional metal-chelate complex.

The alternative synthetic approach of the present invention to generate a bifunctional metal-chelate ligand involved using a lysine derivative and thereby extending the length of the linker chain to enable dialkylation of the equivalent bis-(hydroxylbenzyl) intermediate, as shown in FIG. 1. An efficient bifunctional metal-chelate with improved hydrophilicity and stability is generated using the embodiments of the present invention. The synthetic approach of the present invention for making bifunctional iron-chelate is shown in FIG. 1.

Figure 2:
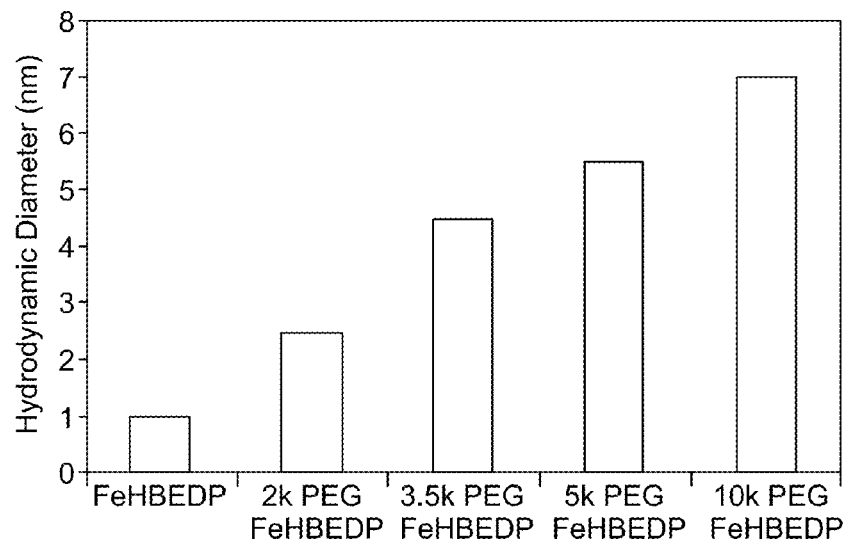
FIG. 2 is a graph showing pegylation of the iron chelate results in systematic increase of the size of the chelating agent.

To increase the size of the metal-chelate, the bifunctional ligand was modified by attaching PEG moiety to the linker of the ligand. The attachment of PEG moiety to the linker is referred to herein as "pegylation". The bifunctionality of the ligand enables pegylation on the linker of the ligand. As shown in FIG. 2, the pegylation of the iron chelate results in systematic increase of the size of the chelating agent, in compared to a non-hydroxylated small molecule control chelate FeHBEDP (Fe-hydroxy his ethylene diamine diphosphonate). The increase in size potentially optimizes in-vivo tissue distribution properties.

Figure 3:
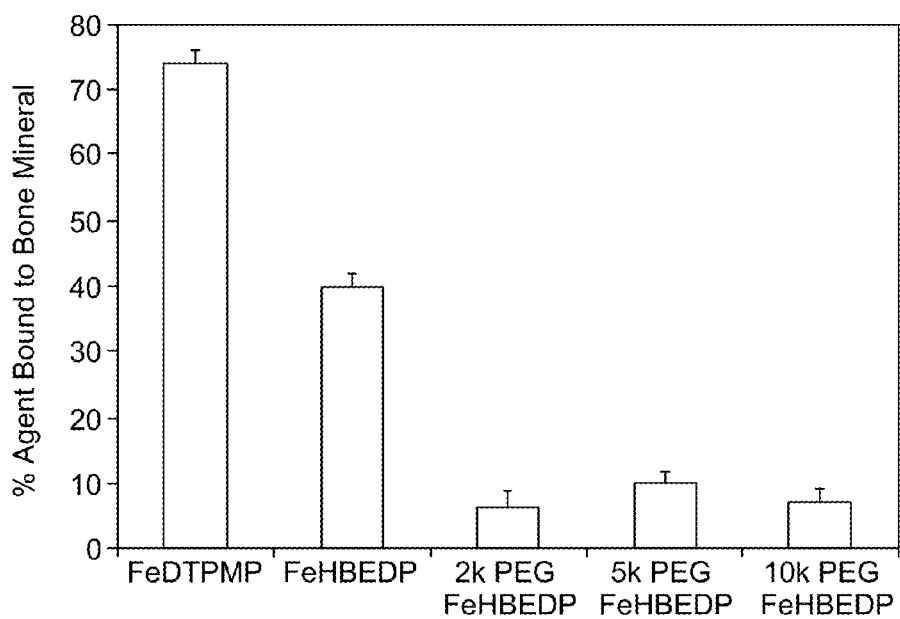
FIG. 3 is a graph showing bone-binding affinity of pegylated bifunctional iron chelates.

The pegylated bifunctional iron chelates provided by the present invention generally demonstrated significantly reduced binding affinity for hydroxyl appetite (HA), which is taken as a measure of bone binding affinity, relative to the control samples, as shown in FIG. 3. The data for pegylated bifunctional iron chelates suggests that a greater PEG size concomitantly reduces the overall bone binding affinity relative to a non-hydroxylated small molecule control chelate FeHBEDP or FeDTPMP [Fe-diethylenetriamine penta(m-ethylene phosphonic acid)].

Figure 4:
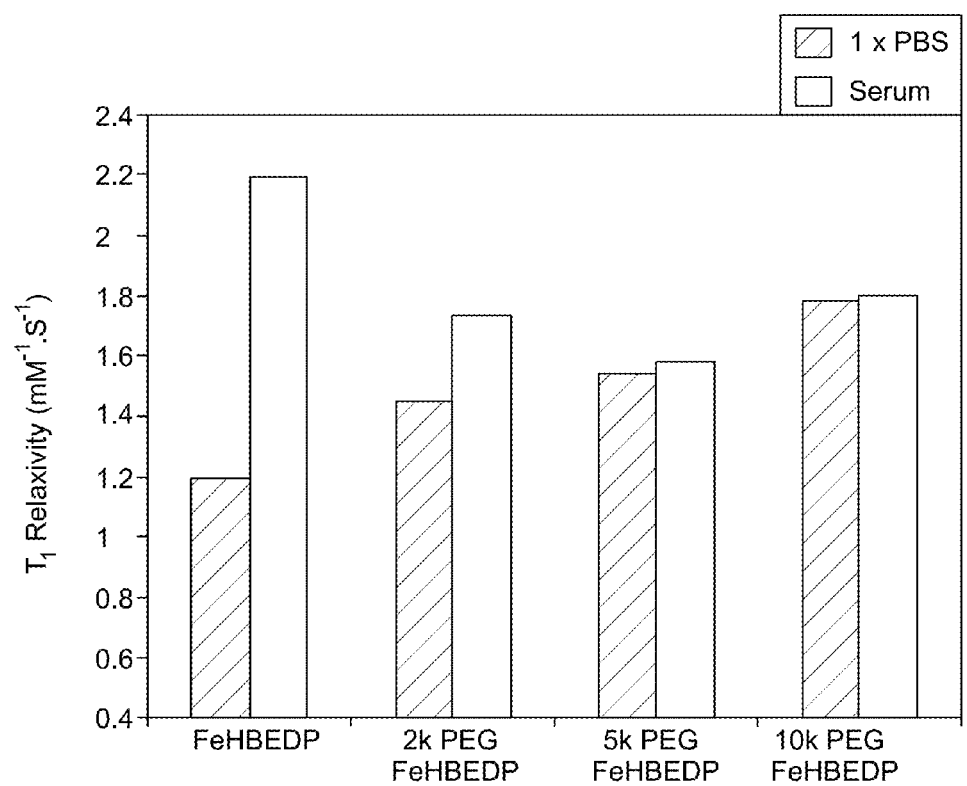
FIG. 4 is a graph showing effect of pegylation of the bifunctional chelating agent on the relaxivities.

The bifunctional contrast enhancement agents comprising PEGs of molecular weights 2 K, 3.5 K, 5 K and 10 K, were compared to the non-hydroxylated small molecule control chelate (FeHBEDP). The beneficial effect of pegylation of the bifunctional chelating agent on the relaxivities is exhibited for the contrast enhancement agents comprising the bifunctional chelating agent with the control samples, as shown in FIG. 4. Increasing the size of the iron chelate concomitantly increases the relaxivity to the highest recorded PBS relaxivities of physiologically acceptable iron chelates. The example further demonstrated that increasing PEG molecular weight concomitantly reduced the protein binding. Therefore, pegylation of the bifunctional iron chelate provides contrast agents with the benefit of maximum relaxivity arising from increased size and minimal toxicity risk from strong protein binding.

Moreover, on the course of the imaging experiment, the distribution of the contrast agent comprising a pegylated bifunctional chelating ligand, such as chelating ligand with PEG of 2 K, enhanced the tumor tissue and enabled MR detection of the malignancy. Finally, the MR signal in the heart and tumor tissue diminished as the agent is eliminated from the body, as shown in FIG. 5.

Small molecule clinical contrast agents are known to clear rapidly and non-selectively from the vascularity to both malignant and benign tissue, limiting diagnostic imaging time and sensitivity. To increase the vascular residence time and tissue selectivity of contrast agents, the agents with high molecular size were applied to determine the effect. A comparison of 2 K, 3.5 K, 5 K, 10 K pegylated iron chelates with the clinical gadolinium chelate, Magnevist, and the experimental protein binding iron chelate, FeHBEDP, unexpectedly showed that agents of 2.5-4.5 nm in size (2 K and 3.5 K PEG) were more rapidly distributed from the blood than the small molecule controls, as shown in FIG. 6.

The rates of small molecule Gd tumor tissue extravasation (as shown in FIG. 7A) and enhancement are too fast on the MR imaging timescale, and the tumor tissue selectivity (as shown in FIG. 7B) is suboptimal, to allow accurate pharmacokinetic differentiation of malignant and benign tissues. Larger contrast agents that provide slower enhancement rates and better tumor tissue selectivity would improve the diagnostic sensitivity and specificity of DCE MR contrast agents for cancer. In comparison to the clinical gadolinium agent, the lesion enhancement rates of pegylated iron agents were reduced to afford a longer dynamic MR imaging window for more precise lesion pharmacokinetic characterization. The whole tumor (FIG. 7 A) and muscle (FIG. 7B) dynamic contrast enhanced (DCE) MR profiles of pegylated iron chelates to that of the gadolinium agent Magnevist (dose: 0.2 mmol/kg Gd, Fe) in a mammary MBIII rodent tumor model are compared. Tumor-to-muscle signal enhancement ratios were used as a proxy for tissue selectivity and indicated improved lesion selectivity for 3-6 nm Fe agents when compared to 1 nm Gd.

A DCE MR pharmacokinetic characterization of whole tumor and muscle tissue with 2 K and 3.5 K pegylated iron chelates are compared to clinical gadolinium chelate and FeHBEDP controls (as shown in FIGS. 8B to 8C). The pharmacokinetic parameters ($K^{trans}$ and $Y_e$) are generated from the concentration-time curve of the left ventricle and tumor signal (FIG. 8A). By vascular permeability ($K^{trans}$) quantitation, it was observed that both pegylated iron agents differentiated tumor and benign muscle tissue more effectively than the small molecule chelate controls (FIG. 8B). The rapid distribution of the small gadolinium agent lead to a large and variable $K^{trans}$, whereas the parent protein binding iron chelate distributed slowly to both tumor and muscle tissue. The larger extravascular extracellular volume ($V_e$) of tumor tissue was detected with all agents and could be used to differentiate benign muscle and malignant regions (FIG. 8 C).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Example 1

Preparation of Amide Compound 1

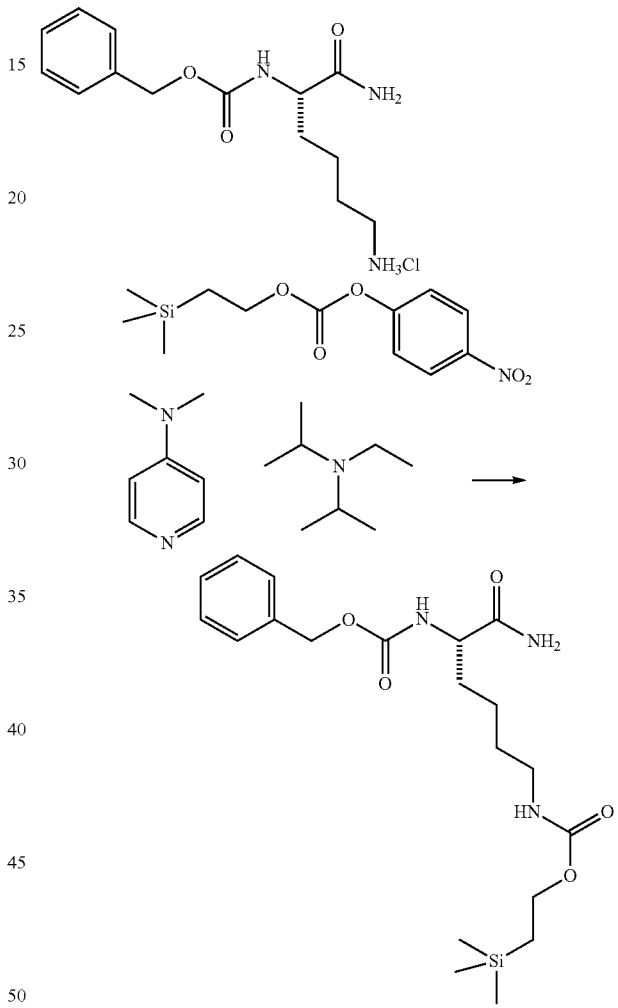

To a suspension of the starting material (1 g, 3.19 mmol) in dichloromethane (31.9 mL) was added Hunig's base (0.021 g, 0.15 mmol), followed by DMAP (7.97 mL). The colorless mixture was stirred for 10 min. and then p-nitrophenyl-(2-trimethylsilyl ethyl)-carbonate (0.993 g, 3.50 mmol) was added to afford a yellow solution which was stirred overnight. The reaction mixture was poured into citric acid solution (100 mL) and diluted with dichloromethane (200 mL). The aqueous and organic layers were separated and the aqueous layer was extracted with dichloromethane (3×100 mL) and the combined organic layers were washed with saturated aqueous potassium carbonate solution, (3×100 mL), brine, dried (magnesium sulfate), filtered and concentrated under reduced pressure to provide the crude product as an off white solid. The crude product was purified by flash chromatography on normal phase silica gel (40 gram column) using the following gradient program at 40 mL/min: 100% dichloromethane for three column volumes, then ramp to 4% methanol-dichloromethane over 15 column volumes, finally holding at 4% methanol-dichloromethane for five column volumes. The column eluant was monitored at 254 nm and the product visualized using PMA stain. The fractions containing the purified material were pooled and concentrated under reduced pressure to provide compound 1 as a colorless crystalline solid that was dried in vacuo. LCMS (ESI) m/z 446, $(M+Na)^+$.

Example 2

Preparation of Nitrile Compound 2

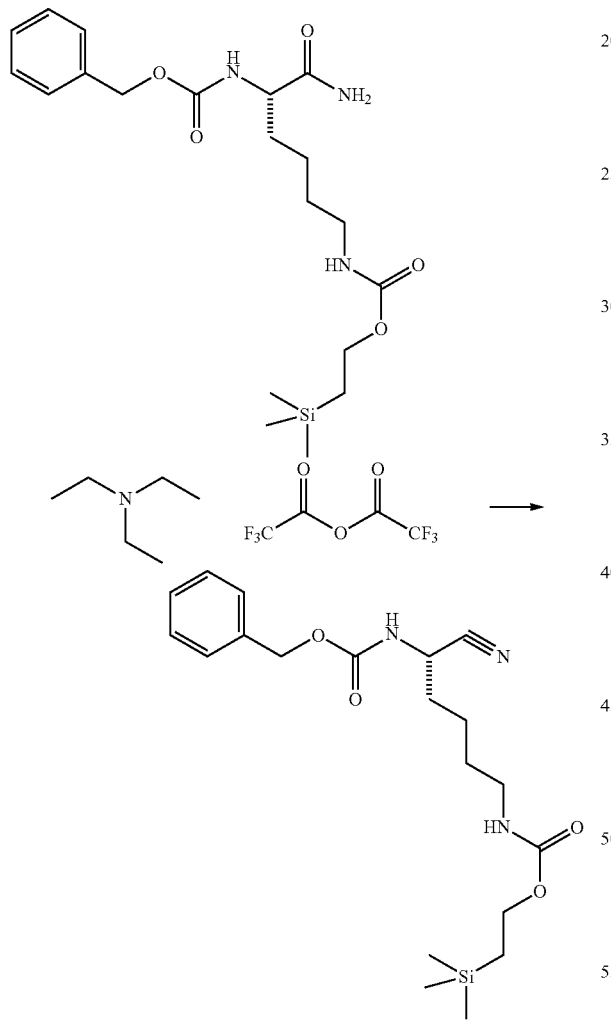

An aliquot of triethylamine (2.44 g, 24.15 mmol) was added to an anhydrous THF (65 mL) solution of compound 1 (4.68 g, 10.98 mmol) at room temperature. The mixture was cooled to 0° C. in an icebath, trifluoroacetic anhydride (2.54 g, 12.08 mmol) was added to the reaction mixture and the reaction mixture was allowed to stirring overnight, slowly warming to room temperature. The reaction mixture was then quenched by the addition of saturated aqueous sodium bicarbonate solution (100 mL). The aqueous and organic layers were separated and the aqueous layer was extracted with dichloromethane (3×50 mL) and the combined organic layers were washed with saturated aqueous potassium carbonate solution, (2×50 mL), brine, dried (magnesium sulfate), filtered and concentrated under reduced pressure to provide the crude product as a yellow oil. The crude product was purified by flash chromatography on normal phase silica gel (120 gram column) using the following gradient program at 85 mL/min: 100% dichloromethane for 5 column volumes, then ramp to 5% methanol-dichloromethane over 15 column volumes, finally holding at 5% methanol-dichloromethane for 5 column volumes. The column eluant was monitored at 254 nm and by staining with PMA stain. The fractions containing purified material were pooled and concentrated under reduced pressure and to yield compound 2 as a pale yellow oil that was dried in vacuo. LCMS (ESI) m/z 428, $(M+Na)^+$.

Example 3

Preparation of Diamine Compound 3

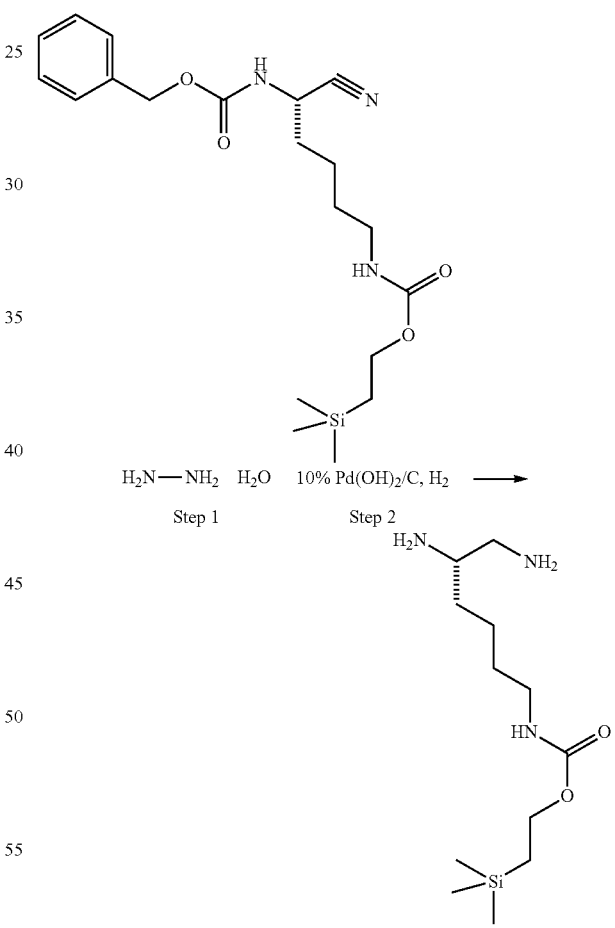

Aliquots of Raney nickel (4.2 g, 9.42 mmol) and hydrazine hydrate (9.43 g, 188 mmol) were added to a solution of the compound 2 (3.82 g, 9.42 mmol) in methanol (314 mL). The reaction mixture was refluxed and its progress monitored by LCMS for three hours until the nitrile was cleanly converted to the desired amine. The reaction mixture was then filtered through a C18 silica gel plug and the filtrate concentrated under reduced pressure to provide the crude monoamine. The residue was dissolved in methanol (200 mL) and Pearlmann's catalyst (500 mg, 10% wt on carbon) was added. The reaction mixture was then vacuum-purged 3 times with hydrogen and stirred overnight. This process was repeated until completion of the debenzylation was confirmed by LCMS and the reaction mixture filtered C18 silica gel plug. The volatiles were removed under reduced pressure and the residue dried in vacuo to provide compound 3 as an oil. LCMS (ESI) m/z 276, (M+H)$^+$.

Example 4

Preparation of Aldehyde Compound 4

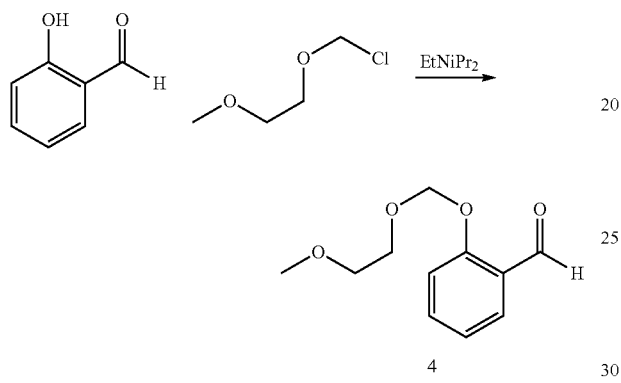

A dichloromethane (200 mL) solution of 2-hydroxybenzaldehyde (10 g, 81.8 mmol) was cooled to 0° C. and Hunig's base (19.5 mL, 114.5 mmol) was added. Following the addition of MEM-Cl (11.2 mL, 94.8 mmol), the reaction mixture was allowed to stir overnight, slowly warming to room temperature. The reaction mixture was quenched by the addition of saturated aqueous NH$_4$Cl solution (60 mL) and the aqueous and organic layers were separated. The aqueous layer was extracted with dichloromethane (2×50 mL) and the combined organic layers were washed with saturated aqueous potassium carbonate solution, (2×20 mL), brine (50 mL), dried over Na$_2$SO$_4$ and filtered. The filtrate was concentrated under reduced pressure to provide the crude product 4 as an oil which was purified by flash chromatography on normal phase silica gel (40 gram column, 0-10% EtOAc-hexanes) to provide the purified compound 4 which was analyzed by LCMS (ESI) 233 (M+Na)$^+$.

Example 5

Preparation of Diamine Compound 5

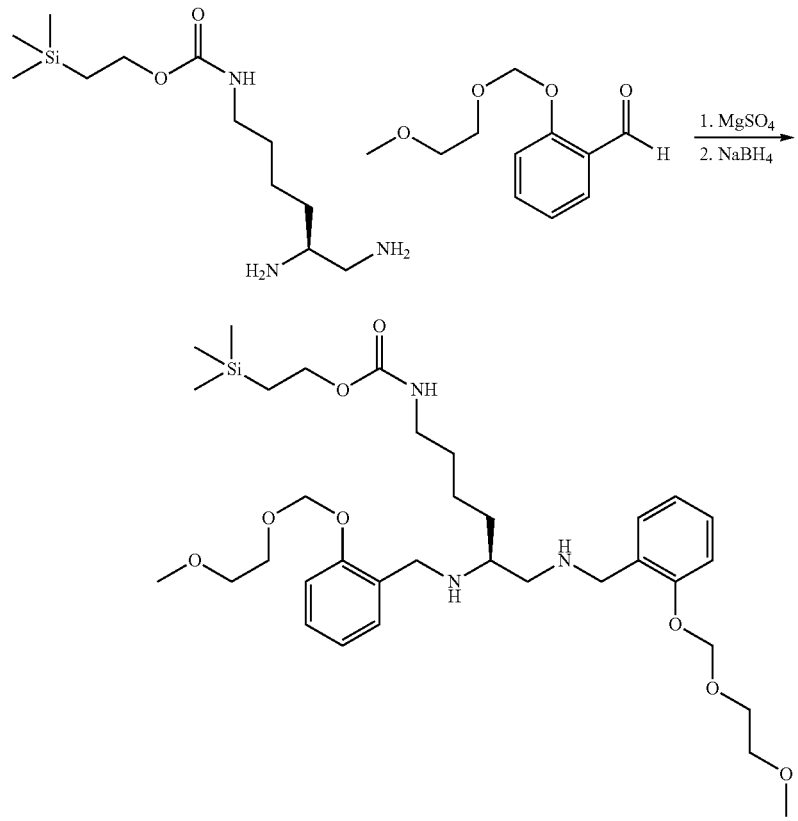

To a stirred suspension of the diamine compound 3 (4.71 g, 17.10 mmol) in dichloromethane (75 mL), were added triethylamine (5.9 mL, 4.48 mmol) and MgSO$_4$ (8.18 g, 68 mmol). After stirring for 1.5 h at room temperature a solution of the aldehyde compound 4 (7.19 g, 34.2 mmol) in dichloromethane (5 mL) was added and the reaction mixture was stirred overnight. The reaction mixture was then filtered to remove solid materials and concentrated under reduced pressure to provide the crude bisimine intermediate as an orange oil that was dried in vacuo. The conversion of aldehyde 3 (δ 10.48 ppm) to the bisimine intermediate (δ 8.60 ppm) was confirmed by $^1$H NMR (CD$_2$Cl$_2$, 400 MHz) spectroscopy and the crude product was then immediately taken on to the next step.

To a dichloromethane (68 mL) solution of bisimine intermediate (10.97 g, 16.62 mmol) at 0° C. was added a methanol (17 mL) solution of sodium borohydride (2.5 g, 66.49 mmol) via an additional funnel. The reaction mixture was allowed to warm to room temperature, stirred overnight and then quenched by the addition of saturated aqueous potassium carbonate solution. The aqueous and organic layers were separated and the aqueous layer was extracted with dichloromethane (2×25 mL). The combined organic layers were washed with saturated aqueous sodium bicarbonate solution, (2×25 mL), brine (2×25 mL), dried over MgSO$_4$ and filtered. The filtrate was concentrated under reduced pressure to provide the crude product as a pale yellow oil which was purified by flash chromatography (SiO$_2$, 120 gram column, 0 to 10% MeOH-dichloromethane 0.5% triethylamine). The column eluant was monitored at 271 nm with the fractions containing the purified material pooled and concentrated under reduced pressure. The purified material was then dried under high vacuum to yield diamine compound 5 as a colorless oil, LCMS (ESI) m/z 664 [M+H]$^+$.

Example 6

Preparation of Hydroxymethyl Phosphonate Compound 6

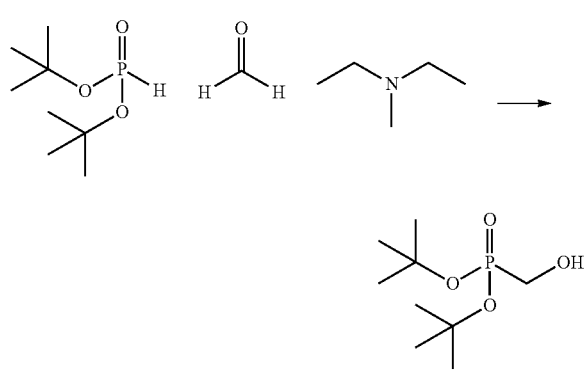

To a solution of the di-tert-butyl phosphite (3.11 g, 16 mmol) was added water (1 mL), triethylamine (2.6 mL, 19.2 mmol), and 37% formaldehyde (1.2 mL, 16 mmol). The reaction mixture was sealed and stirred overnight followed by coevaporation with three portions of methanol and one portion of dichloromethane. The crude reaction mixture and was then dried in vacuo to afford compound 6 as a colorless crystalline solid that was then analyzed by NMR. The isolated material was not stored under vacuum or kept for any length of time due to a noted propensity for this compound to decompose. The solid material was redissolved in dichloromethane once a weight had been recorded for conversion to triflate compound 7.

Example 7

Preparation of Triflate Compound 7

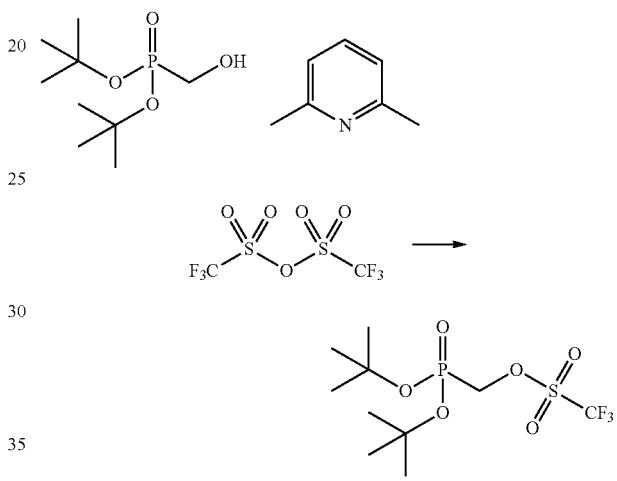

Freshly prepared hydroxymethyl phosphonate compound 6 (3.63 g, 16.1 mmol) was dissolved in dichloromethane (52 mL) and an aliquot of lutidine (3.7 mL, 32.2 mmol) was added. The reaction mixture was cooled to –70° C., followed by dropwise addition of triflic anhydride (3 mL, 17.8 mmol) over 30 minutes through the agency of a syringe pump. The reaction mixture was stirred for 2 h at –70° C. and was stored overnight in a –80° C. freezer. The mixture was removed from the freezer, chilled in a dry ice/isopropanol bath and diethylether (100 mL) was added to the mixture all at once. The resulting precipitates were filtered from the cool reaction mixture using Celite and the filtrate was diluted with deionized water (75 mL). The aqueous and organic layers were separated; the aqueous layer extracted with diethyl ether (25 mL) and the combined organic layers were washed with water (3×25 mL), brine (2×25 mL) and dried (magnesium sulfate). The solution was filtered and gently concentrated under reduced pressure to provide the triflate compound 7 as a yellow-orange oil. $^1$H NMR (CD$_2$Cl$_2$, 400 MHz) δ 4.5 ppm, (d, J=8 Hz, 1H), 1.55 (s, 18H). A portion of the isolated material was used immediately to prepare compound 8 and the remaining material was stored neat in the –80° C. freezer. After standing for five days at –80° C., the neat product was thawed and another NMR was obtained. There was no apparent decomposition of this material at this time, indicating that the desired reagent is stable for routine preparation and use when stored at –80° C.

Example 8

Preparation of Phosphonate Compound 8

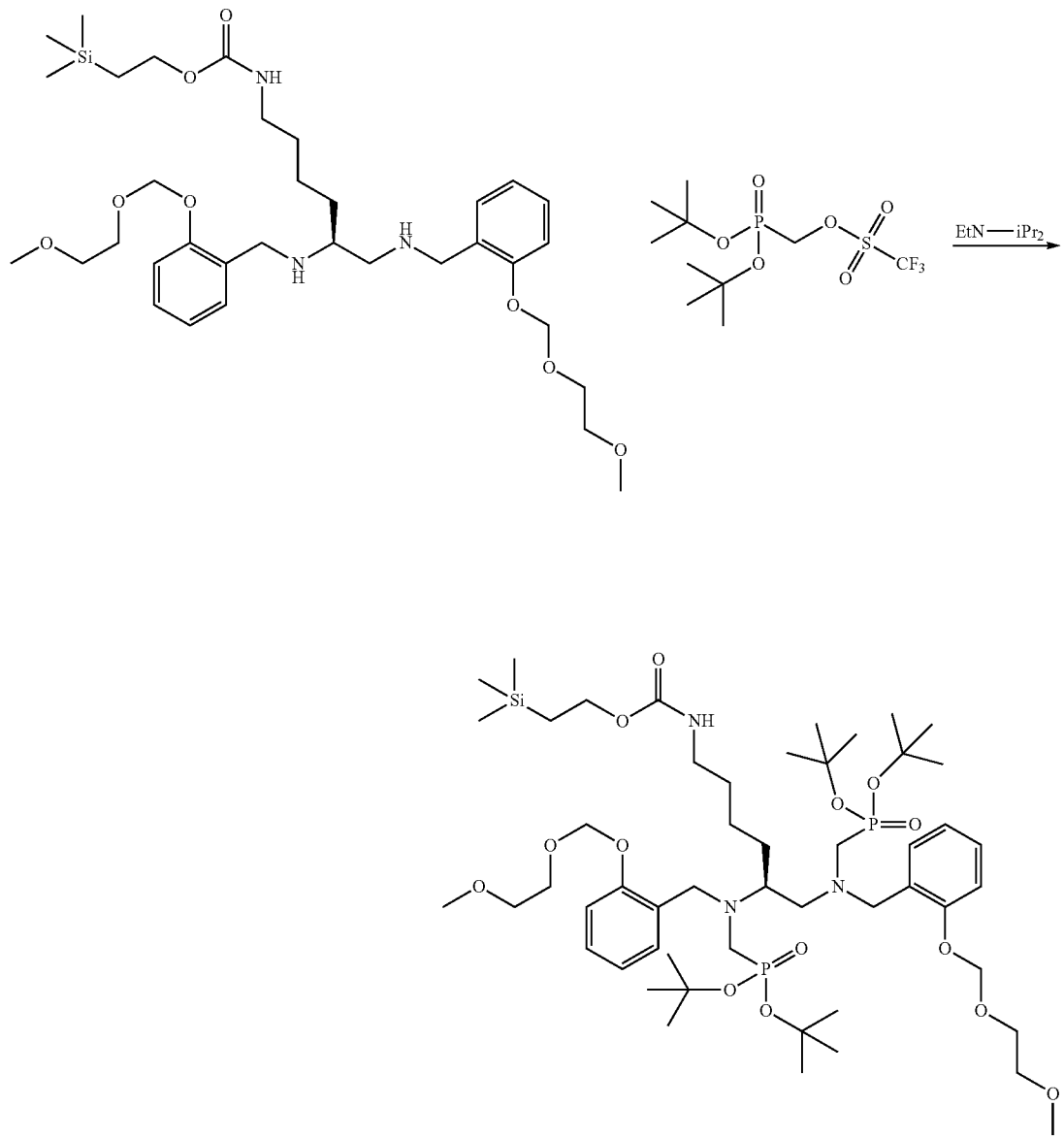

An acetonitrile (22 mL) solution of diamine compound 5 (5.39 g, 8.11 mmol) and Hunig's base (5.7 mL, 40.6 mmol) was prepared at ambient temperature. In a separate vial, triflate compound 7 (6.93 g, 19.5 mmol) was dissolved in acetonitrile (5 mL) and added then to the reaction mixture. The reaction mixture was stirred with monitoring of the reaction progress by LCMS. After 4 hours the volatiles were removed under reduced pressure to provide a residue that was dissolved in ethyl acetate (100 mL) and extracted with aqueous saturated potassium bicarbonate (25 mL). The organic layer was washed with water (3×25 mL), brine (2×25 mL) and dried (sodium sulfate). The solution was filtered and the volatiles removed under reduced pressure to afford a yellow oil that was purified by flash chromatography (SiO$_2$, 120 gram column, 0 to 75% ethyl acetate-hexanes 0.3% triethylamine). The column eluant was monitored at 271 nm with the fractions containing the purified material pooled and concentrated under reduced pressure. The purified material was then dried under high vacuum to yield phosphonate compound 8 as a pale yellow oil, LCMS (ESI) m/z 1076 [M+H]$^+$, 1020 [M−tBu+H]$^+$.

Example 9

Preparation of Amine Compound 9

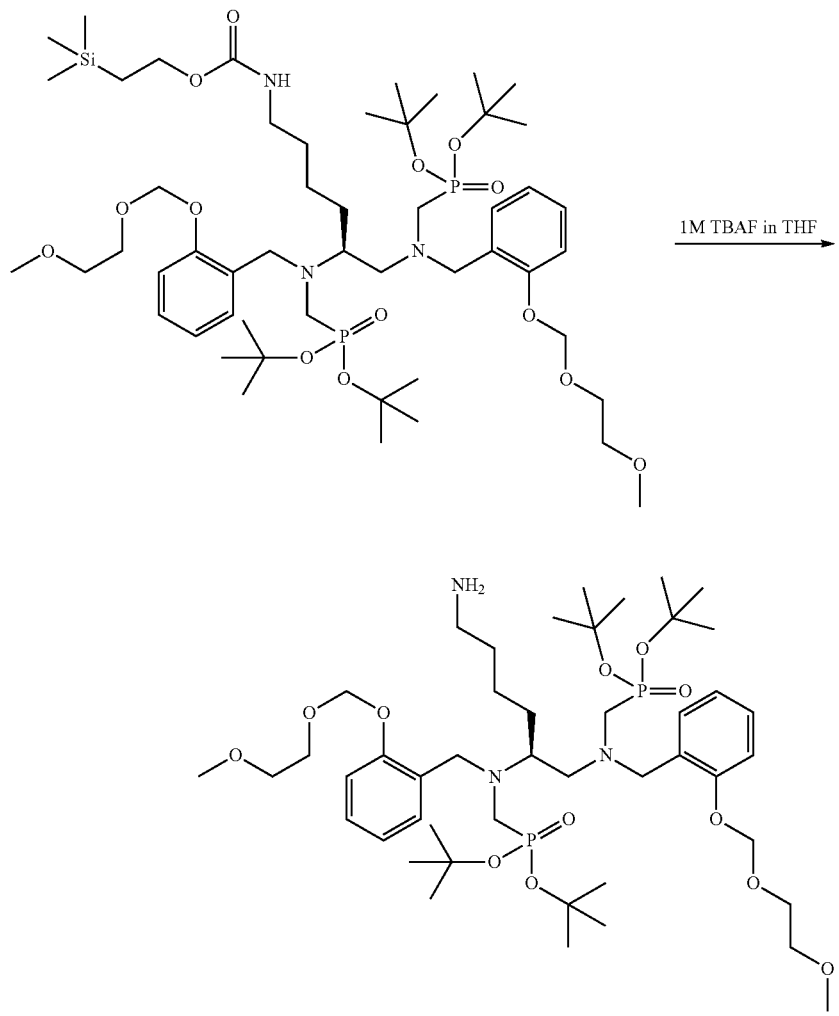

The phosphonate compound 8 (1.0 g, 1.0 mmol) was dissolved in a 1M solution of TBAF in tetrahydrofuran (3.04 mL) and the reaction was allowed to continue stirring overnight. The reaction mixture was then poured into of saturated aqueous potassium carbonate (25 mL) solution and diluted with water (150 mL) and dichloromethane (75 mL). The aqueous and organic layers were separated; the aqueous layer extracted with dichloromethane (3×25 mL) and the combined organic layers were dried (magnesium sulfate), filtered and concentrated under reduced pressure to provide the crude product as a yellow oil. The residue was purified by flash chromatography (SiO$_2$, 120 gram column) using the following gradient program at 85 mL/min: 100% dichloromethane w/0.5% triethylamine for 3 column volumes, then ramp to 10% methanol-dichloromethane each w/0.5% triethylamine over 20 column volumes, finally holding at 10% methanol-dichloromethane each w/0.5% triethylamine for 3 column volumes. The column eluant was monitored at 270 nm and the fractions of purified material were pooled and concentrated under reduced pressure. The purified amine compound 9 was isolated as a colorless oil that was further dried in vacuo and then analyzed by LCMS (ESI) m/z 932 [M+H]$^+$, 954 [M+Na]$^+$ Proton spectra calibrated against CD$_2$Cl$_2$ at 5.32 ppm, Carbon spectra was calibrated against CD$_2$Cl$_2$ at 53.84. Additional peaks in the $^{13}$C NMR were a result of C—P couplings. $^1$H NMR (CD$_2$Cl$_2$) δ 1.32-1.39 (m, 4H), 1.42 (s, 9H), 1.43 (s, 9H), 1.45 (s, 9H), 1.46 (s, 9H), 1.62-1.77 (m, 2H), 2.29 (br. s, 2H), 2.57-2.67 (m, 3H), 2.71-2.88 (m, 5H), 3.01 (br. s, 1H), 3.30 (s, 3H), 3.32 (s, 3H), 3.44-3.49 (m, 2H), 3.49-3.54 (m, 2H), 3.63 (d, J=14.3 Hz, 1H), 3.70-3.78 (m, 4H), 3.80-3.94 (m, 3H), 5.14-5.27 (m, 4H), 6.96 (dd, J$_1$=12.8, J$_2$=14.6 Hz, 2H), 7.07 (dd, J$_1$=3.9, J$_2$=9.5 Hz, 2H), 7.11-7.22 (m, 2H), 7.51 (dd, J$_1$=7.4, J$_2$=1.1 Hz, 1H), 7.74 (dd, J$_1$=7.3, J$_2$=1.3 Hz, 1H); $^{13}$C NMR (CD$_2$Cl$_2$) δ 11.96, 24.56, 30.61, 30.64, 30.69, 30.74, 30.77, 31.25, 34.10, 42.35, 46.59, 48.54, 48.64, 46.08, 50.81, 53.41, 53.67, 53.78, 55.03, 55.75, 55.80, 57.78, 57.86, 57.97, 57.98, 68.10, 68.13, 72.00, 72.01, 81.74, 81.79, 81.82, 81.88, 81.98, 82.07, 82.16, 93.95, 94.02, 114.09, 114.34, 121.75, 121.79, 127.61, 127.99, 128.63, 129.68, 131.00, 131.04, 155.76, 155.97

Example 10

Preparation of 10 KDa-Pegylated Chelate Compound 10

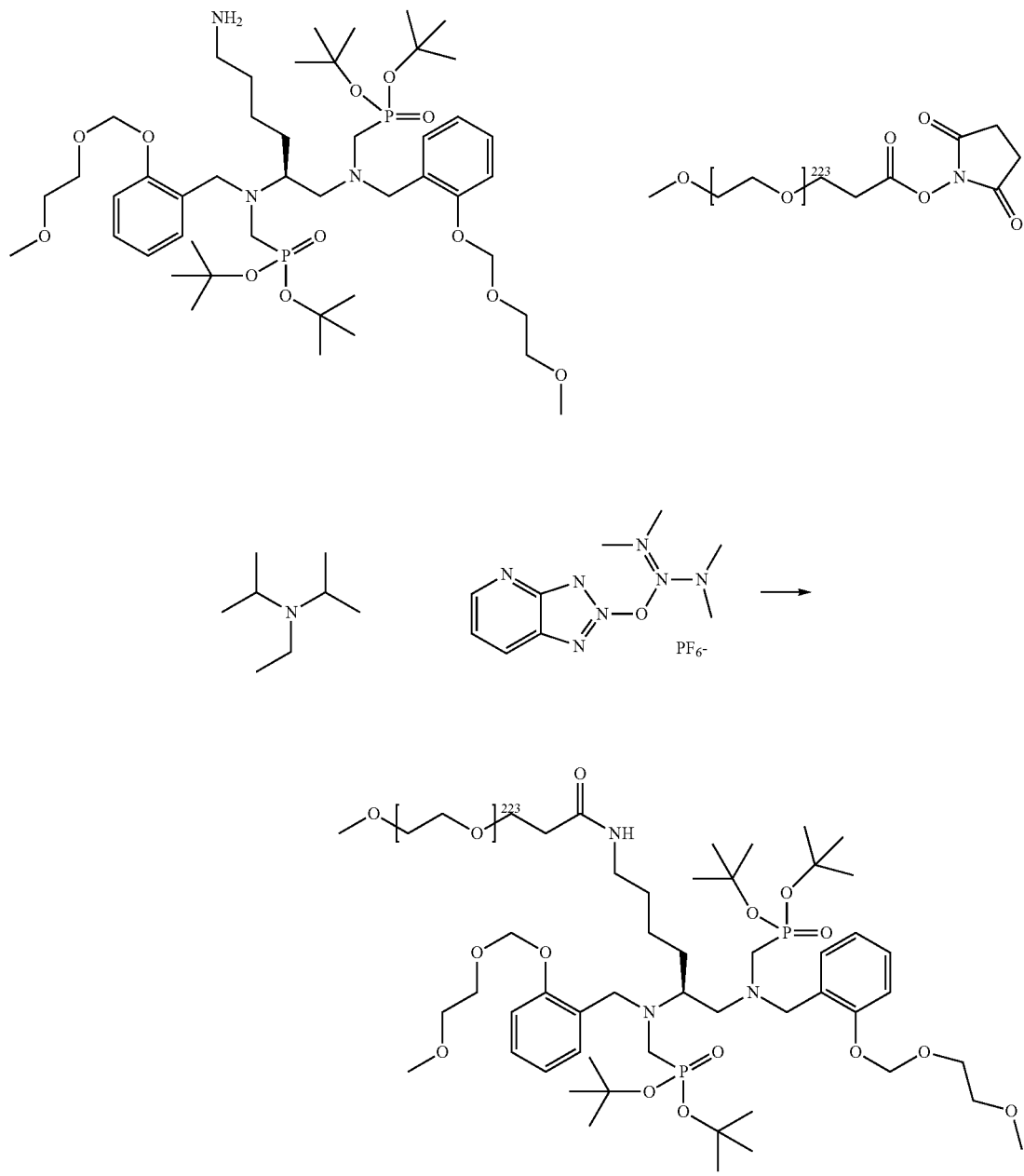

The starting 10 KDa PEG-NHS ester (3.09 g, 0.308 mmol, Supplier: NANOCS) was placed in a round bottomed flask and dissolved in dichloromethane (31 mL) solution of Hunig's base (0.159 g, 1.233 mmol). The amine compound 9 (0.293 g, 0.31 mmol) was dissolved in a minimal amount of dichloromethane and added to the reaction mixture followed by stirring for 72 h at ambient temperature. An aliquot of HATU (0.146 g, 0.385 mmol) was added to the reaction mixture and the reaction was allowed to stir for an additional 24 hours at room temperature. The reaction mixture was concentrated under reduced pressure and the residue was then precipitated upon addition to diethyl ether (500 mL). The precipitate was collected by centrifugation, washed with diethylether (100 mL) and then collected by dissolving with dichloromethane. The solution was concentrated under reduced pressure and the resulting off-white solid then dried in vacuo. The isolated compound 10 was characterized by GPC analysis and then taken on to the next iron complexation step.

Example 11

Preparation of 10K-Pegylated Iron Compound 11

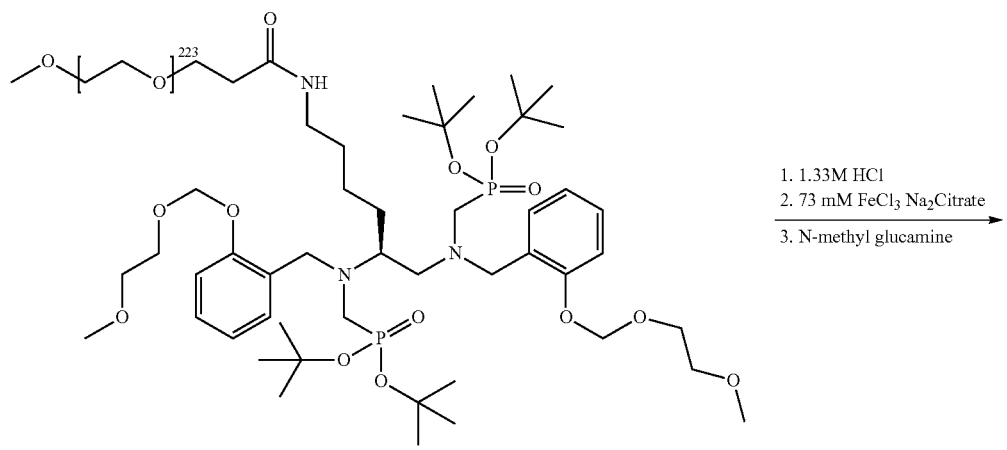

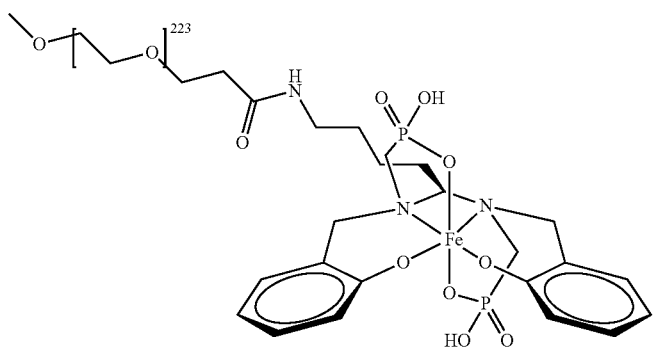

The pegylated 10 KDa compound 10 (0.230 mmol) was dissolved in water (12 mL) and 3.9 M aqueous HCl (6 mL) was added. The reaction mixture was allowed to continue stirring at room temperature overnight before heating for an additional 3 h at 60° C. The reaction mixture was allowed to cool to ambient temperature and then stirred for an additional 16 hours. Portions of N-methyl glucamine were added to the reaction mixture until the pH was approximately 8. In a separate flask, sodium citrate tribasic (0.169 g, 0.547 mmol, 2 eq with respect to Fe) was combined with a 73 mM FeCl$_3$ stock solution (3.94 mL, 0.287 mmol) and the mixture was shaken until the solids had dissolved completely. The resulting green solution was added dropwise to the reaction mixture over about 5 minutes and a red color ensued. The pH of the mixture was checked and N-methylglucamine was added if necessary to bring the reaction pH to 8 or above. The mixture was heated in a 60° C. oil bath for approximately 30 minutes to drive transchelation of the iron to completion, as signified by the formation of a deep red colored solution. The mixture was loaded into a 500 Da MWCO dialysis membrane and placed in a water bath that was of approximately 100× larger in volume than the membrane. The water bath was stirred and changed at 2 h, 26 h, 50 h, and at 68 h. Following the final change the bath was allowed to continue stirring for an additional 2 h. The bath was colored at the 26 and 50 h changes, indicating that there was some material loss during the dialysis process. The dialysis retentate material was concentrated under reduced pressure and lyophilized to afford pegylated iron compound 11 as a red solid that was dissolved in water (5 mL) and an aliquot analyzed by GPC (Abs. $\lambda_{max}$=460 nm, RT=4.96 mins), dynamic light scattering, ICP and $r_1$ and $r_2$ PBS relaxivity studies.

Example 12

Preparation of 3K-Pegylated Chelate Dimer Compound 12

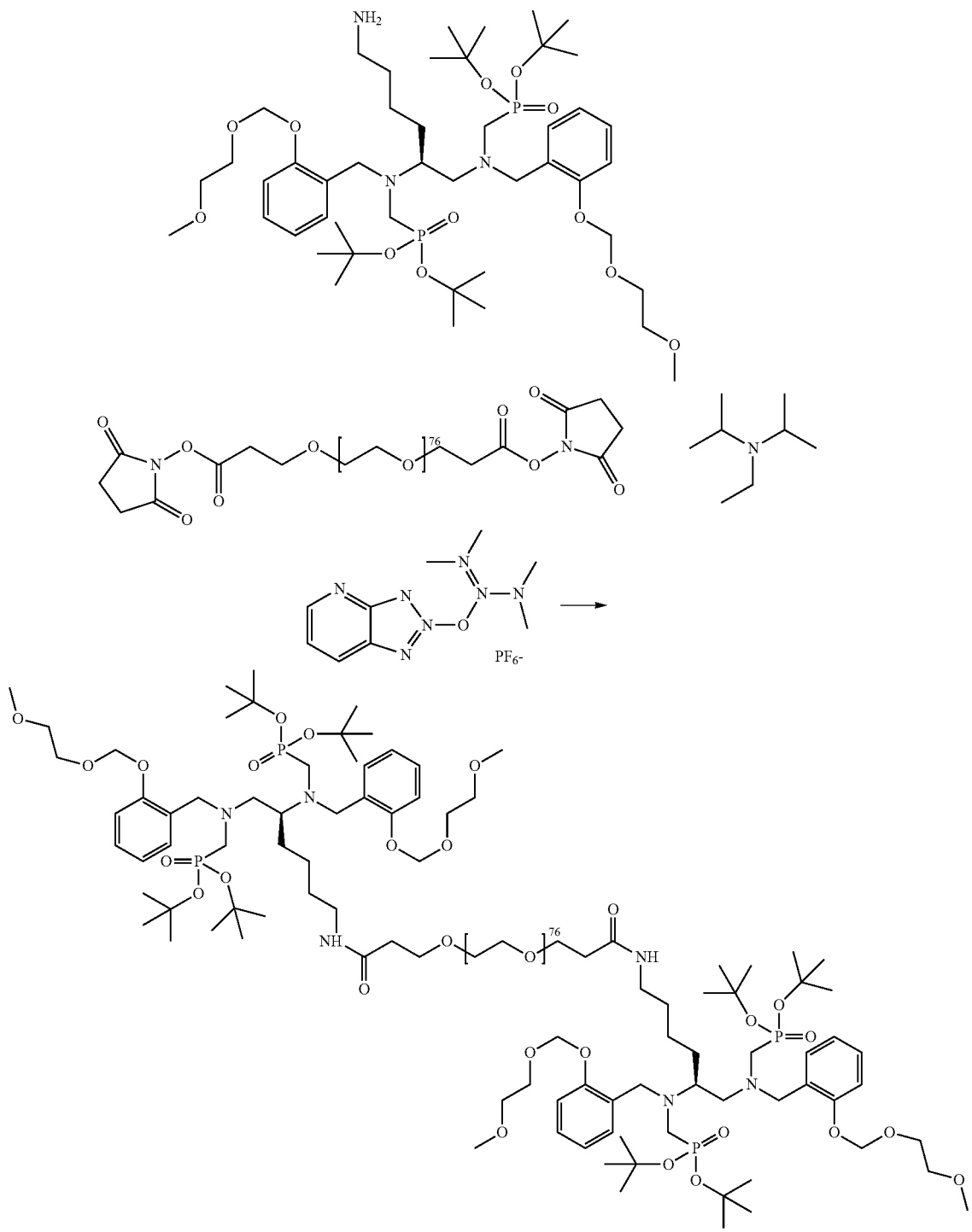

The starting 3.4 KDa PEG-NHS ester (0.81 g, 0.24 mmol, Supplier: NANOCS) was placed in a round bottomed flask and dissolved in dichloromethane (24 mL) solution of Hunig's base (0.247 g, 1.91 mmol). The amine compound 9 (0.668 g, 0.72 mmol) was dissolved in a minimal amount of dichloromethane and added to the reaction mixture followed by stirring for 72 h at ambient temperature. An aliquot of HATU (0.27 g, 0.72 mmol) was added to the reaction mixture and the reaction was allowed to stir for an additional 24 hours at room temperature. The orange reaction mixture was concentrated under reduced pressure and the residue was then precipitated upon addition to diethyl ether (100 mL). The precipitate was collected by centrifugation, washed with diethylether (100 mL) and then collected by dissolving with dichloromethane. The solution was concentrated under reduced pressure and the resulting oil converted to an off-white solid when dried in vacuo. The isolated compound 12 was characterized by GPC analysis and then taken on to the next iron complexation step.

Example 13

Preparation of 3K-Pegylated Iron Dimer Compound 13

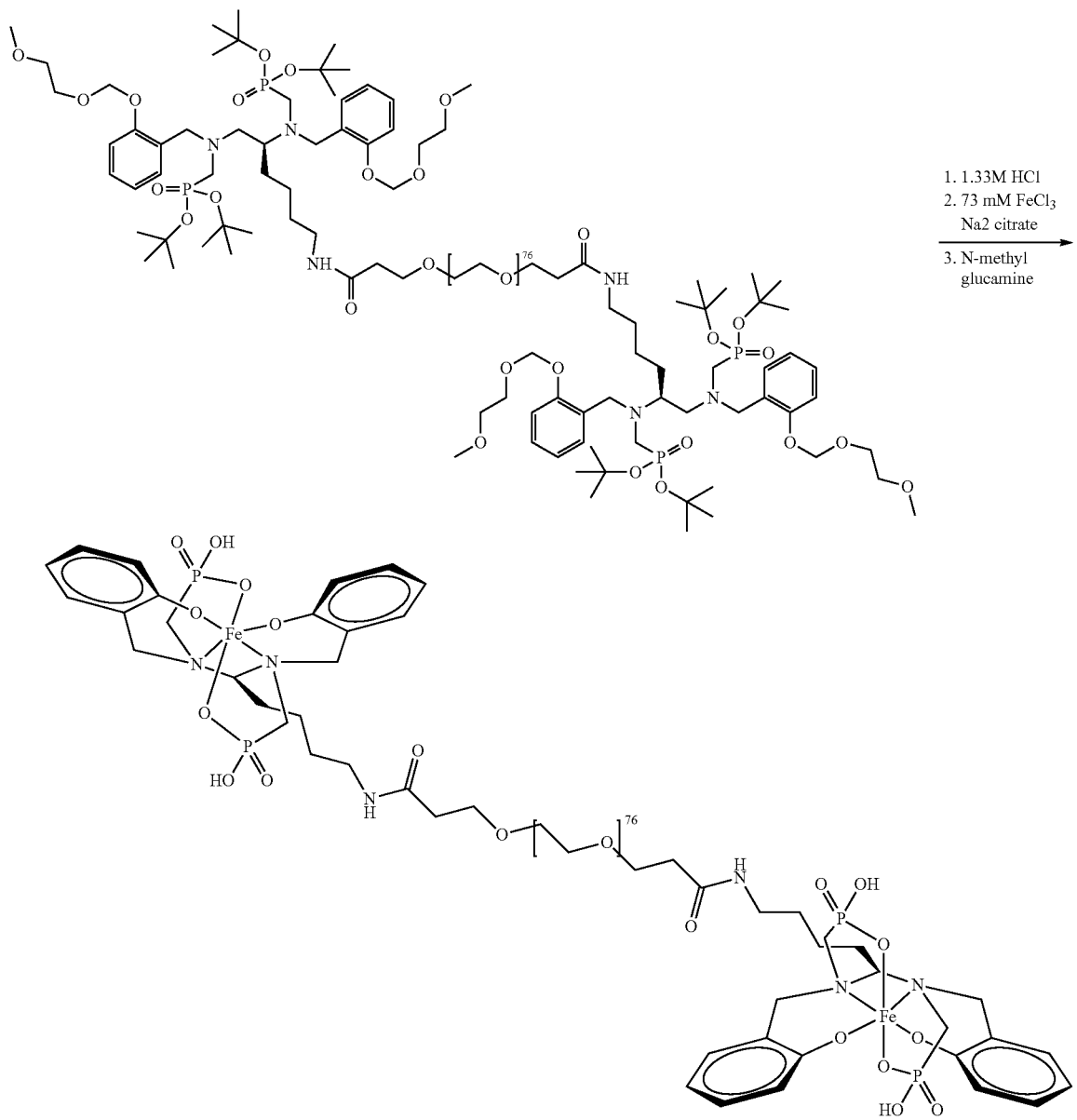

16 hours. In a separate flask, sodium citrate tribasic (0.418 g, 1.42 mmol, 3 equivalents with respect to Fe) was combined with a $FeCl_3$ (0.116 g, 0.717 mmol) and the mixture was shaken until the solids had dissolved completely. The resulting green solution was added dropwise to the reaction mixture over about 5 minutes and a red color ensued. The pH was adjusted to 8 using N-methylglucamine and the mixture was stirred overnight to afford a deep red solution at which point the pH was readjusted to 8 using N-methylglucamine. The mixture was loaded into a 3500 Da MWCO dialysis membrane and placed in a water bath that was of approximately 100× larger in volume than the membrane. The water bath was stirred and changed at 2 h, 26 h, 50 h, and at 68 h. Following the final change the bath was allowed to continue stirring for an additional 2 h. The bath was colored at the 26 and 50 h changes, indicating that there was some material loss during the dialysis process. The dialysis retentate material was filtered through a sintered glass frit, concentrated under The pegylated 3.4 KDa compound 12 (0.22 mmol) was dissolved in water (24 mL) and 3.9 M aqueous HCl (12 mL) was added. The reaction mixture was allowed to continue stirring at room temperature overnight before heating for an additional 3 h at 60° C. The reaction mixture was allowed to cool to ambient temperature and then stirred for an additional reduced pressure and lyophilized. The resulting red solid, pegylated iron compound 13, was dissolved in water (5 mL) and an aliquot analyzed by GPC (Abs. $\lambda_{max}$=456 nm, RT=5.5 mins), dynamic light scattering, ICP and $r_1$ and $r_2$ PBS relaxivity studies.

Example 14

Preparation of Contaminated 10K-Pegylated Iron Compound 11

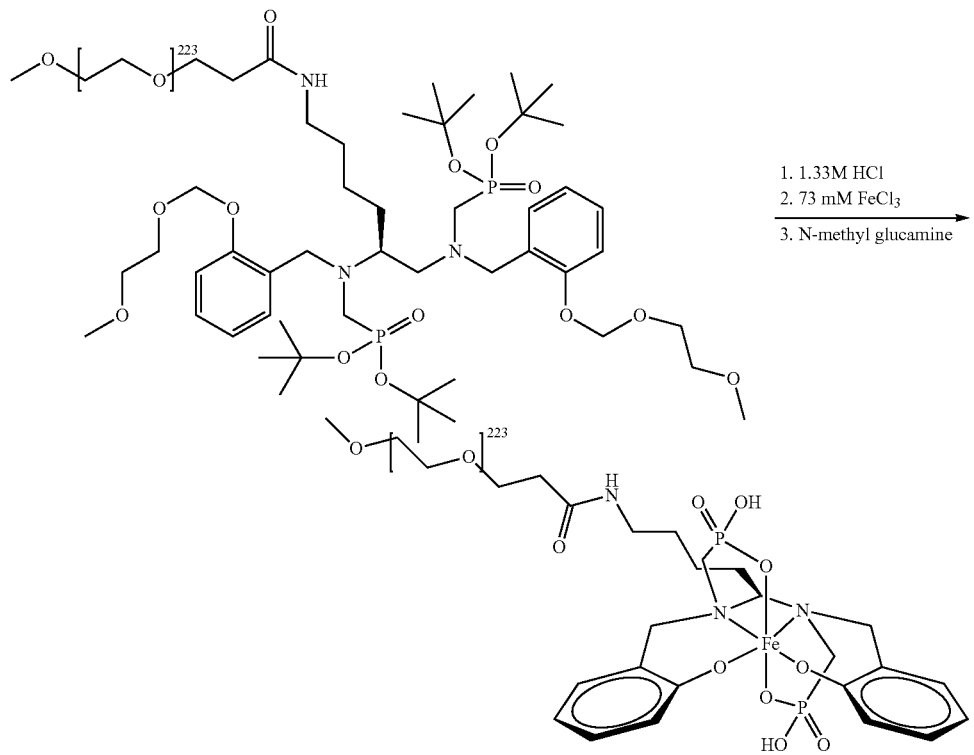

The pegylated 10 KDa compound 10 (0.56 mmol) was dissolved in water (20 mL) and 3.9 M aqueous HCl (10 mL) was added. The reaction mixture was allowed to continue stirring at room temperature overnight before heating for an additional 3 h at 60° C. The reaction mixture was allowed to cool to ambient temperature and then stirred for an additional 16 hours. To the stirred solution was added a stock 73 mM solution of FeCl$_3$ in water (7.7 mL, 0.56 mmol), and the mixture stirred for 30 minutes before quenching with N-methyl glucamine to pH 9. The resulting orange-red solution was loaded into a 3500 Da MWCO dialysis membrane and placed in a water bath that was of approximately 100× larger in volume than the membrane. The water bath was stirred and changed at 4 h, 21 h, 29 h, and at 45 h. The dialysis retentate was concentrated under reduced pressure and lyophilized to provide an orange solid. The lyophilized material was dissolved in water (5 mL) and an aliquot analyzed by GPC (Abs. $\lambda_{max}$=456 nm, RT=4.10 mins), dynamic light scattering, ICP and $r_1$ and $r_2$ PBS relaxivity studies. The relaxivity measurements indicated that metal content was close to magnetically inactive ($r_1$=0.2·mmol$^{-1}$·s$^{-1}$, $r_2$=0.5 mmol$^{-1}$·s$^{-1}$) and the GPC indicated a significantly higher molecular weight portion than observed with the corresponding 10K pegylated compound 10. (method 10, RT=4.96 minutes).

Example 15

Recovery of 10K-Pegylated Iron Compound 11

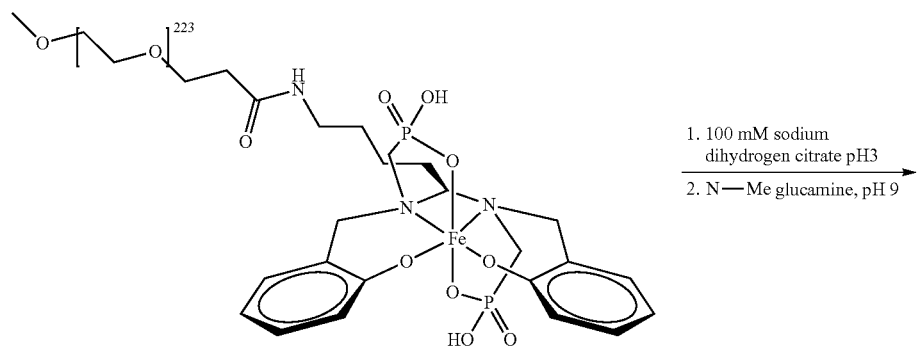

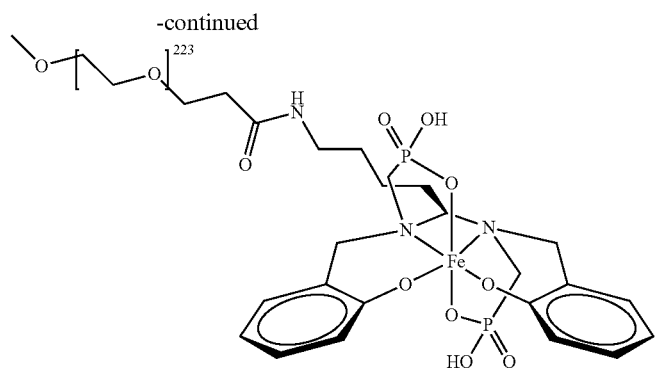

A red-orange aliquot of the contaminated 10K-Pegylated Iron compound from method 14 (75 uL) was acidified to pH3 using 25 mM sodium dihydrogen citrate (100 mL, 2.5 mmol) and stirred at ambient temperature overnight. The clear pale yellow solution was then quenched to pH 8 using N-methyl glucamine to afford a red solution. The mixture was loaded into a 3500 Da MWCO dialysis membrane and dialyzed against water. The bath was changed at 2, 16, 40, and 90 h and following the final change, the mixture was allowed to continue stirring for 4 h. GPC analysis of this material indicated that the high molecular weight contaminants and citrate had been completely removed. The material was lyophilized and the resulting red solid was dissolved in water (5 mL) for analysis by GPC (Abs. $\lambda_{max}$=456 nm, RT=5.0 mins), dynamic light scattering, ICP and $r_1$ and $r_2$ PBS relaxivity studies. The relaxivity measurements indicated that metal content was close to magnetically active ($r_1$=1.8·mmol$^{-1}$·s$^{-1}$, $r_2$=1.8 mmol$^{-1}$·s$^{-1}$) and the GPC indicated an equivalent molecular weight to the corresponding 10K pegylated compound 11. (method 10, RT=4.96 minutes).

Example 16

Preparation of Ester Compound 14

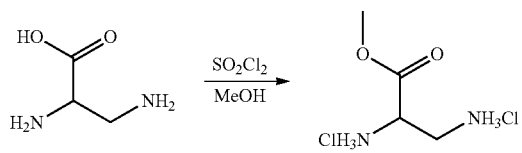

Thionyl chloride (31.7 g, 266.8 mmol) was added drop wise to a stirred suspension of 2,3-diaminopropionic acid monohydrochloride (5.0 g, 35.6 mmol) in methanol (75 mL) over a period of 5 min. The reaction mixture was heated to 80° C. for 6 h. At the end of the stipulated time, the reaction mixture was cooled and the volatiles were removed under reduced pressure to obtain compound 14 (6.8 g, 100%) as an off-white solid. $^1$H NMR (MeOD): 4.51 (m, 1H), 3.96 (s, 3H), 3.53 (m, 2H).

Example 17

Preparation of Diamine Compound 15

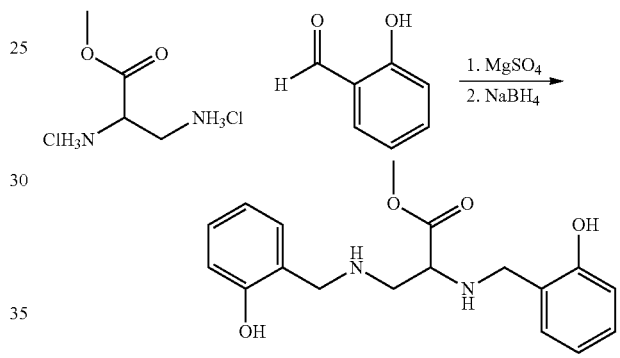

To a stirred suspension of the diamine compound 14 (1.3 g, 3.7 mmol) in dichloromethane (10 mL), were added triethylamine (1.3 mL, 9.3 mmol) and MgSO$_4$ (1.8 g, 14.9 mmol). After stirring for 1.5 hours at room temperature, a solution of the aldehyde compound (1.57 g, 7.46 mmol) in dichloromethane (5 mL) was added. The reaction mixture was allowed to stir overnight. The reaction mixture was then filtered to remove solid materials and then concentrated under reduced pressure to provide a crude product. The crude product was triturated with diethyl ether, the ether was filtered and concentrated under reduced pressure to provide a yellow oil. The conversion of aldehyde ($\delta$ 10.55 ppm) to bisimine intermediate ($\delta$ 8.76 ppm) was confirmed by $^1$H NMR (CD$_2$Cl$_2$, 400 MHz) spectroscopy.

To a dichloromethane solution (4 mL) of the bisimine 2.7 g (3.7 mmol) at 0° C. was added a methanol solution (1 mL) of sodium borohydride 0.56 g (14.9 mmol) via an additional funnel. The reaction mixture was allowed to warm to room temperature and stirred overnight. The reaction mixture was then quenched by the addition of saturated aqueous potassium carbonate solution (10 mL). The aqueous and organic layers were separated and the aqueous layer was extracted with dichloromethane (3×25 mL) and the combined organic layers were washed with saturated aqueous sodium bicarbonate solution, (2×25 mL), brine (2×25 mL), dried over MgSO$_4$ and filtered. The filtrate was concentrated under reduced pressure to provide the crude product as a pale yellow oil which was purified by flash chromatography (SiO₂, 40 gram column) using the following gradient program at 60 mL/min: 100% dichloromethane containing 0.5% triethylamine for 3 column volumes, then ramp to 10% methanol-dichloromethane each containing 0.5% triethylamine over 20 column volumes, finally holding at 10% methanol-dichloromethane each containing 0.5% triethylamine for 2 column volumes. The column eluant was monitored at 278 nm and the fractions containing the purified material were pooled, concentrated under reduced pressure. The orange colored product obtained was further dried under high vacuum and was then analyzed by LCMS. LCMS analysis indicated that only partial purification of the reaction product had been achieved. Thus, the crude product was again subjected to flash chromatography on normal phase silica gel (40 gram column) using the following gradient program at 40 mL/min: 50% EtOAc-hexanes for 3 column volumes, then ramp to 75% EtOAc-hexanes over 20 column volumes, finally holding at 75% EtOAc-hexanes for 6 column volumes. The column eluant was monitored at 277 nm, and the fractions containing the purified material were pooled and concentrated under reduced pressure to provide a colorless oil. The residue was dried under high vacuum to yield purified diamine compound 15 as a colorless oil, LCMS (ESI) 737 [M+H]⁺.

Example 18

Attempted Alkylation of Diamine Compound 15

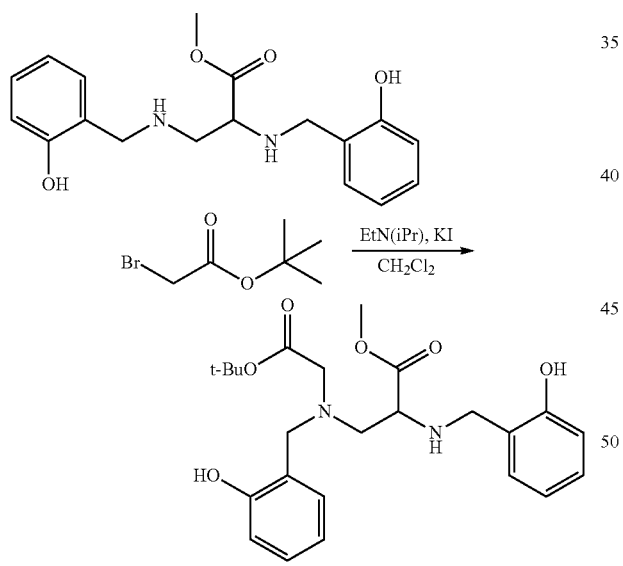

Hunig's base (0.20 g, 1.55 mmol) was added to a DMF (2.9 mL) solution of diamine 15 (0.13 g, 0.39 mmol) and the mixture was stirred for 30 min. In a separate vial, potassium iodide (0.19 g, 1.16 mmol) was dissolved in DMF (1 mL) and combined with tert-butyl bromoacetate (0.16 g, 0.82 mmol). The mixture was stirred for 30 min and then added to the solution of diamine 15 and Hunig's base in DMF before stirring overnight. LC-MS analysis of a sampled aliquot indicated that the reaction had proceeded to mono-substitution and also indicated the presence of minor impurities. The reaction mixture was then heated to at 80° C. and stirred overnight. LC-MS analysis indicated a mixture of products with no evidence for the formation of the desired disubstituted compound.

Example 19

Preparation of Acetal Aldehyde Compound 16

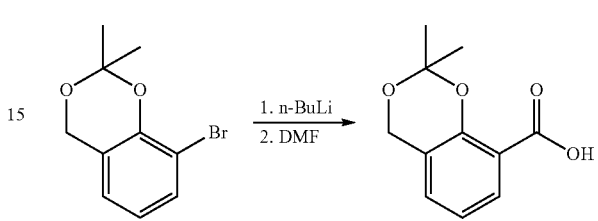

3-bromosalicyl alcohol isopropylidene acetal (5.05 g, 22.1 mmol) was prepared as using the method described in Meier C. et al. Eur J. Org. Chem. 2006, 197. An aliquot of n-BuLi in hexanes (about 8.31 mL, 20.77 mmol) was diluted with anhydrous tetrahydrofuran (about 30 mL). The diluted n-BuLi was cooled to a temperature of about –75.degree. C. A solution of 3-bromosalicyl alcohol isopropylidene acetal in about 15 mL anhydrous THF was then added over a period of 1.5 h, while maintaining the internal reaction temperature at or below –70.degree. C. in an acetone/dry ice bath. Following the addition of the 3-bromosalicyl alcohol isopropylidene acetal, the reaction mixture was stirred for an additional 30 min while maintaining the temperature at or below –70.degree C. At the end of 30 min anhydrous DMF (1.62 mL, 20.77 mmol) was added to the reaction mixture over a period of 30 sec. The reaction mixture was allowed to re-equilibrate to a temperature of about –70.degree C., and the reaction mixture warmed to about 0.degree C. The reaction mixture was then quenched by the addition of methanol (30 mL), and was poured into saturated aqueous NaHCO₃, and then extracted with dichloromethane (3.times.75 mL). The combined organic extracts were dried over MgSO₄, filtered, and concentrated under reduced pressure to provide a yellow oil that solidified on standing under high vacuum. The crude material was purified by flash chromatography (SiO₂, 40 g column, isocratic, 10% EtOac-hexanes, 254 and 327 nm) to afford the aldehyde compound 16 as a pale yellow solid, m/z=195 [M+3H]+.

Example 20

Preparation of Acetal Diamine Compound 17

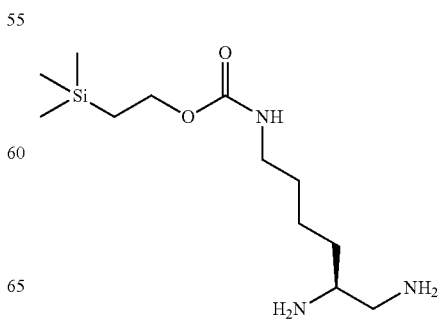

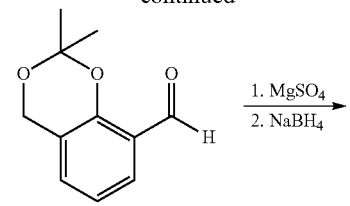

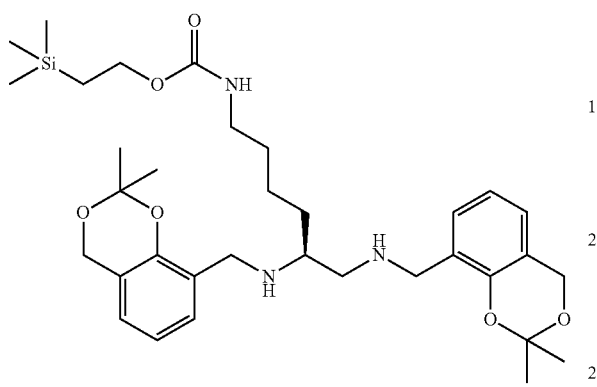

To a suspension of the starting material 3 (2.23 g, 8.1 mmol) in dichloromethane (3 mL) was added triethylamine (20.5 g, 20.5 mmol) and MgSO₄ (3.9 g, 35.4 mmol). The mixture was allowed to stir for 1 h at room temperature and then a solution of the acetal aldehyde compound 16 (3.11 g, 16.19 mmol) in dichloromethane (1 mL) was added. The reaction mixture was allowed to continue stirring for 36 h then filtered and concentrated under reduced pressure to provide a crude product. The residue was triturated with diethylether and the resulting solids removed by filtration. The filtrate was concentrated under reduced pressure to provide the acetal bisimine intermediate as a yellow-orange oil. The conversion of aldehyde (δ 10.44 ppm) to the bisimine intermediate (δ 8.57 ppm) was confirmed by $^1$H NMR (CD$_2$Cl$_2$, 400 MHz) spectroscopy and the crude product was then immediately taken on to the next step.

To a dichloromethane (4 mL) solution of the acetal bisimine intermediate (0.614 mmol) at 0° C. was added a solution of sodium borohydride (0.149 g, 3.94 mmol) in methanol (1 mL) via an additional funnel. The reaction mixture was allowed to continue stirring, slowly warming to room temperature overnight, and the reaction mixture was then quenched by the addition of saturated aqueous potassium carbonate solution. The aqueous and organic layers were separated and the aqueous layer was extracted with dichloromethane (3×25 mL). The combined organic layers were washed with saturated aqueous sodium bicarbonate solution (2×25 mL), brine, dried (magnesium sulfate), filtered and concentrated under reduced pressure to provide the crude product as a pale yellow oil. The crude product was purified by flash chromatography on normal phase silica gel (40 gram column, 0 to 10% methanol-dichloromethane, 0.5% triethylamine). The column eluant was monitored at 277 nm and the purified material was pooled and concentrated under reduced pressure. The purified acetal diamine compound 17 was obtained as a pale yellow oil that was further dried under high vacuum. LC-MS m/z 628 [M+H]⁺.

Example 21

Preparation of Acetal Phosphonate Compound 18

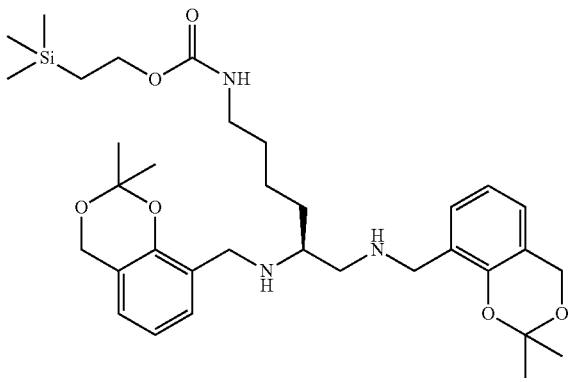

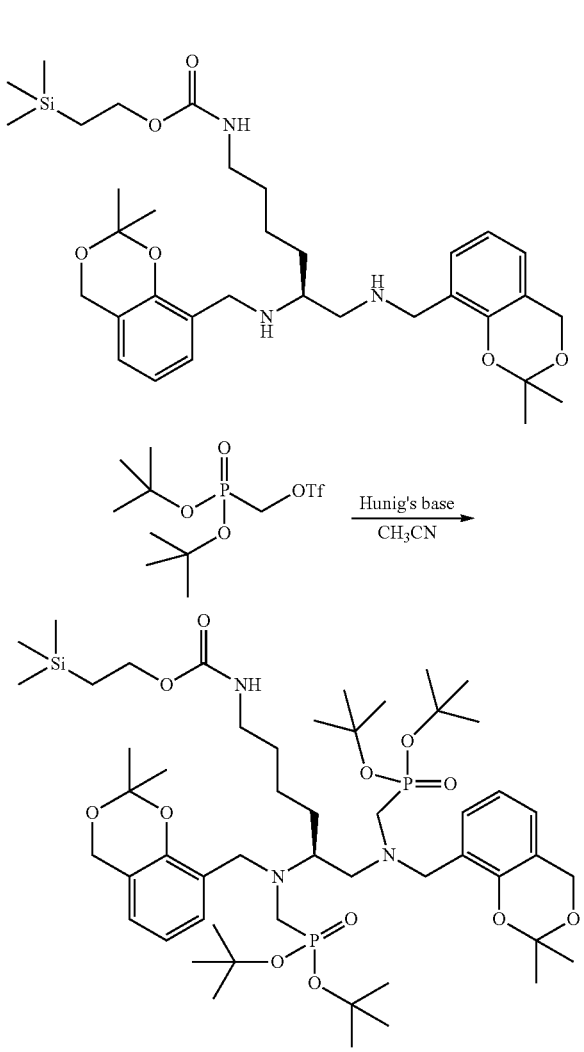

To an acetonitrile solution (5 mL) of the acetal diamine 17 (0.86 g, 1.37 mmol) was added Hunig's base (1.22 mL, 6.85 mmol) followed by triflate compound 7 (1.17 g, 3.29 mmol). The reaction mixture was allowed to continue stirring overnight and then quenched by the addition of saturated aqueous potassium carbonate solution and ethyl acetate. The aqueous and organic layers were separated, the aqueous layer extracted with ethyl acetate (3×25 mL) and the combined organic layers were washed with saturated potassium carbonate (2×25 mL), dried (magnesium sulfate), filtered and concentrated under reduced pressure to provide the crude product as a yellow oil. The crude product was purified by flash chromatography on normal phase silica gel (40 gram column, 75-95% ethyl acetate-hexanes, 0.5% triethylamine). The column eluant was monitored at 281 nm and the purified material was pooled and concentrated under reduced pressure. The residue was further dried under high vacuum to provide acetal phosphonate compound 18 as a colorless oil LC-MS m/z 1040 [M+H]+.

Example 22

Preparation of Acetal Amine Compound 19

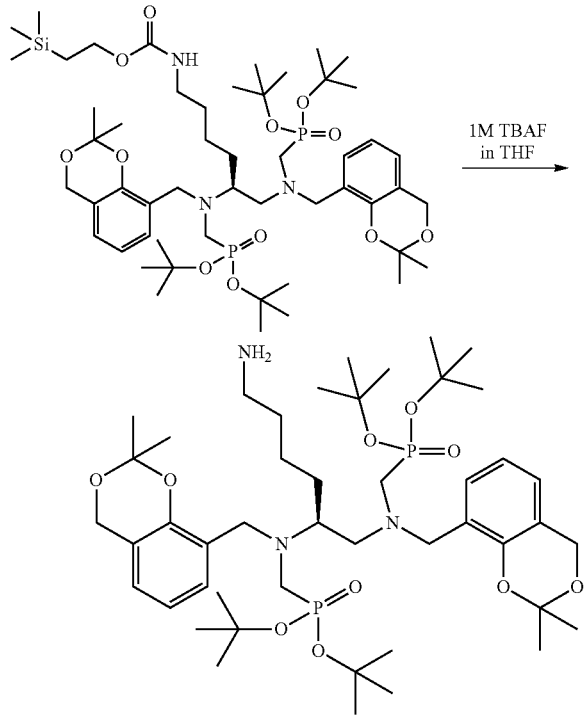

The acetal phosphonate compound 18 (0.08 g, 0.075 mmol) was dissolved in a 1M solution of TBAF in tetrahydrofuran (0.225 mL, 0.225 mmol) and the reaction was allowed to stir overnight. The reaction mixture was then poured into a saturated aqueous potassium carbonate solution and extracted with dichloromethane (5×5 mL). The aqueous and organic layers were separated; the aqueous layer extracted with dichloromethane (3×25 mL) and the combined organic layers were dried (magnesium sulfate), filtered and concentrated under reduced pressure to provide the crude amine intermediate 19 as a yellow oil. LC-MS m/z 896 [M+H]+.

Example 23

Preparation of Acetal Dimethyl Amine Compound 20

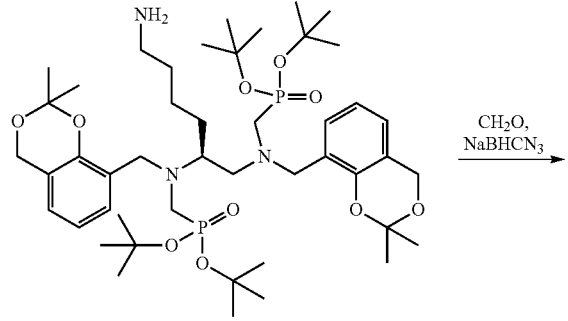

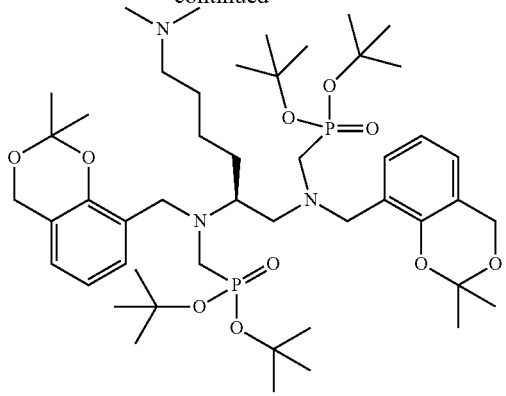

The acetal amine compound 19 (0.17 g, 0.19 mmol) was dissolved in 1,2-dichloroethane (1.9 mL) and Hunig's base (0.22 g, 1.69 mmol) and treated with a 37 wgt % formaldehyde solution (0.30 g, 3.8 mmol) at ambient temperature. A solid portion of sodium cyanoborohydride (0.12 g, 0.56 mmol) was introduced and the reaction mixture stirred overnight. The reaction mixture was then concentrated under reduced pressure to provide a residue that was redissolved in dichloromethane (10 mL) and partitioned against of saturated aqueous potassium carbonate solution (10 mL). The aqueous and organic layers were separated and the aqueous layer was extracted with dichloromethane (3×10 mL). The combined organic layers were washed with saturated aqueous potassium carbonate solution, (2×25 mL), dried (magnesium sulfate), filtered and concentrated under reduced pressure to provide the crude product as a pale yellow oil. The crude product was purified by flash chromatography (SiO$_2$, 40 gram column, 0 to 10% methanol-dichloroethane, 0.5% triethylamine). The column eluant was monitored at 270 nm and the fractions of purified material were pooled and concentrated under reduced pressure. The purified dimethyl amine compound 20 was isolated as a pale yellow oil that was further dried in vacuo and taken immediately to the next step.

Example 24

Preparation of Hydroxymethyl Iron Compound 21

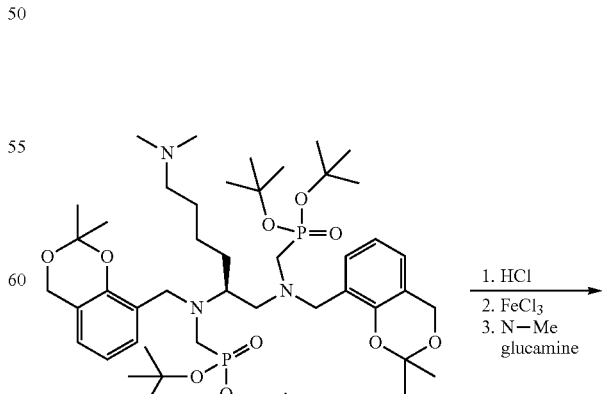

-continued

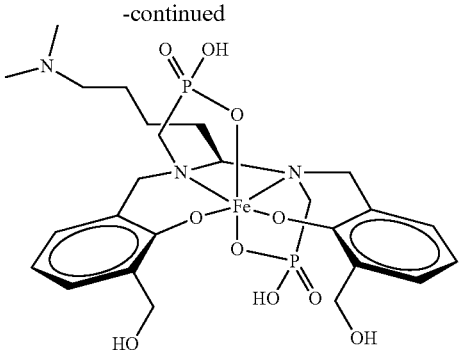

The acetal dimethylamine compound 20 (0.19 mmol) was deprotected by stirring overnight in a 1 M HCl solution (3:1 dioxane-water, 1.5 mL). A solution of iron chloride hexahydrate (41 mg, 0.15 mmol) in deionized water (0.5 mL) was introduced to the deprotected ligand and the resulting pink mixture stirred for 15 min at room temperature. The reaction mixture was quenched to pH 5 with N-methyl glucamine to afford a solid that was pelleted by centrifugation and washed with acetonitrile (50 mL). The solid was suspended in deionized water (2 mL) and the basicity adjusted to pH 9 with N-methyl glucamine to afford a red solution of hydroxymethyl iron compound 21. LC-MS m/z 691 [M+Na]$^+$.

Example 25

Preparation of Iron Compound 22

A portion of dimethylamine compound 21 (33.6 mg, 0.06 mmol) was deprotected by stirring overnight in a 1 M HCl solution (3:1 dioxane-water, 1.5 mL). A solution of iron chloride hexahydrate (19.4 mg, 0.076 mmol) in deionized water (1 mL) was introduced to the deprotected ligand and the mixture stirred for 15 min at room temperature. The solution was then quenched to pH 9 with N-methyl glucamine. The reaction mixture was added to the acetonitrile (40 mL) in a centrifuge tube. The centrifuge tube was vortexed and then centrifuged (3000 rcf, 10 min, 24° C.) and the supernatant decanted to provide an oily purple pellet that was resuspended in acetonitrile (40 mL), vortexed, centrifuged and decanted. The process was repeated a third time and then the resulting pellet dissolved in deionized water (500 µL) to afford a red solution that was purified by flash chromatography (Sephadex-G10, 8 gram plug, deionized water). The red column eluent was collected and lyophilized to afford compound 22 as a red solid. MALDI-MS (α-CHCA Matrix) m/z 611 [M−H]$^-$.

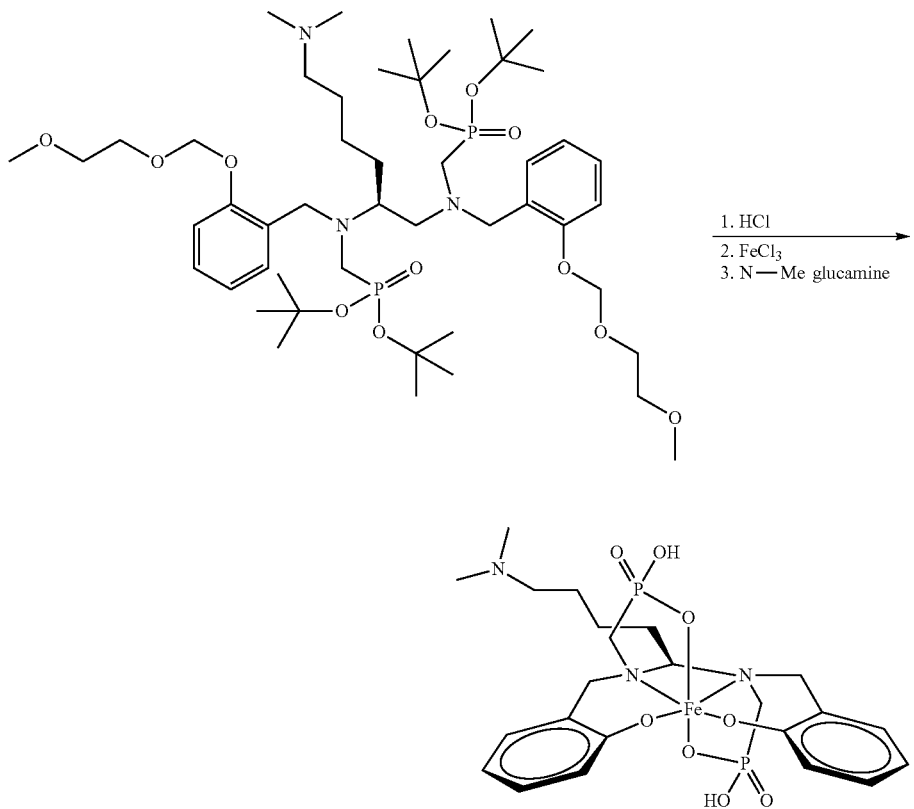

Example 26

Preparation of Gallium Compound 23

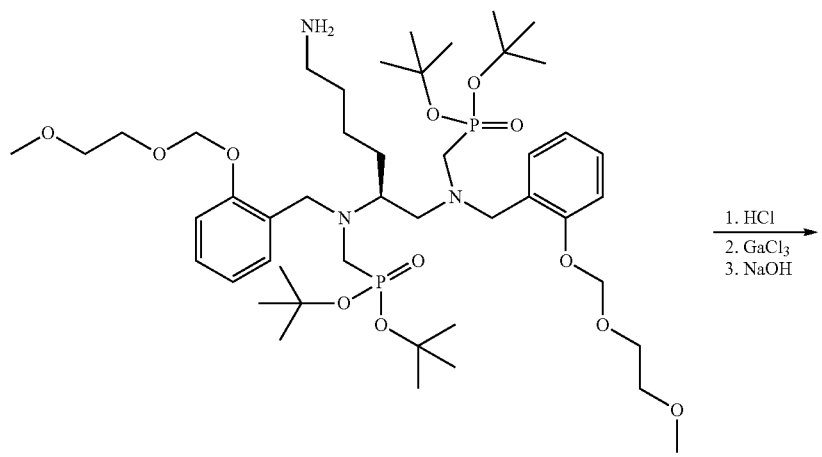

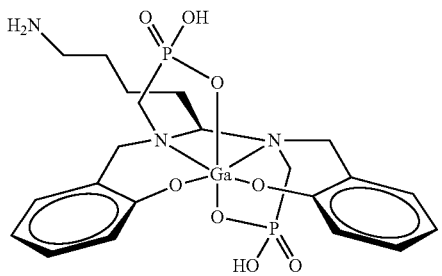

A combination of water (1.5 mL) followed by 3.9 M aqueous HCl (0.5 mL, 1.95 mmol) was added to a vessel containing the amine compound 9 (0.114 g, 0.112 mmol). The vessel was sealed and the mixture was stirred at 65° C. for 3 h. The reaction mixture allowed to cool to room temperature and then GaCl3 was added to the reaction mixture followed by a 1M NaOH solution to bring the reaction mixture to ~pH 8. After stirring for ~15 min a sample was taken for LCMS analysis (attached). No chelated gallium species was observed at this time. A small portion of N-methylglucamine was added to the reaction mixture and the mixture was stirred at 65° C. for 3 h. The reaction mixture allowed to cool to room temperature overnight and then another sample was taken for LCMS analysis which indicated formation of the gallium chelate compound, 23. LCMS (ESI) m/z 598 [M+H]+.

Example 27

Preparation of Ester Compound 24

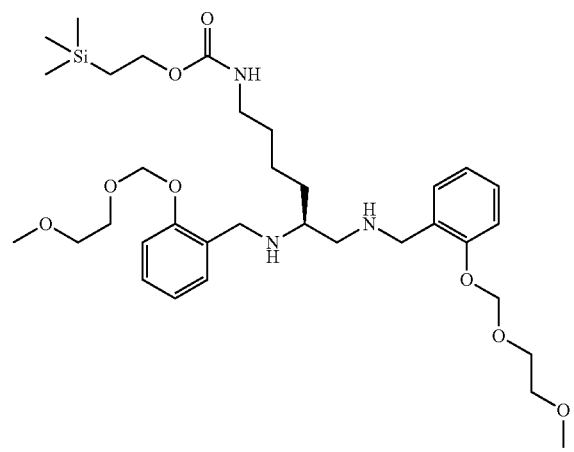

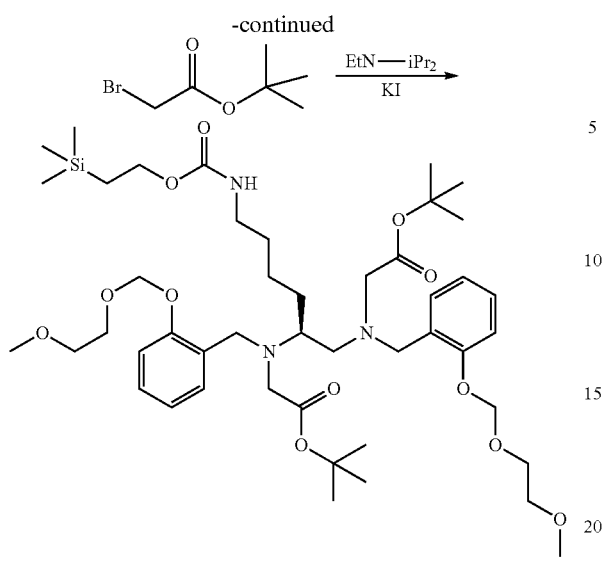

Hunig's base (0.20 g, 1.55 mmol) is added to a DMF (2.9 mL) solution of diamine 5 (0.26 g, 0.39 mmol) and the mixture is stirred for 30 min. In a separate vial, potassium iodide (0.19 g, 1.16 mmol) is dissolved in DMF (1 mL) and combined with tert-butyl bromoacetate (0.16 g, 0.82 mmol). The mixture is stirred for 30 min and added to the solution of diamine 5 and Hunig's base in DMF before stirring overnight. The resulting reddish-brown solution is cooled to ambient temperature and concentrated under reduced pressure to form a dark crude oil. The residue is purified by column chromatography (SiO$_2$, 0 to 10% ethyl acetate-hexanes) to obtain the ester compound 24.

Example 28

Preparation of Amine Compound 25

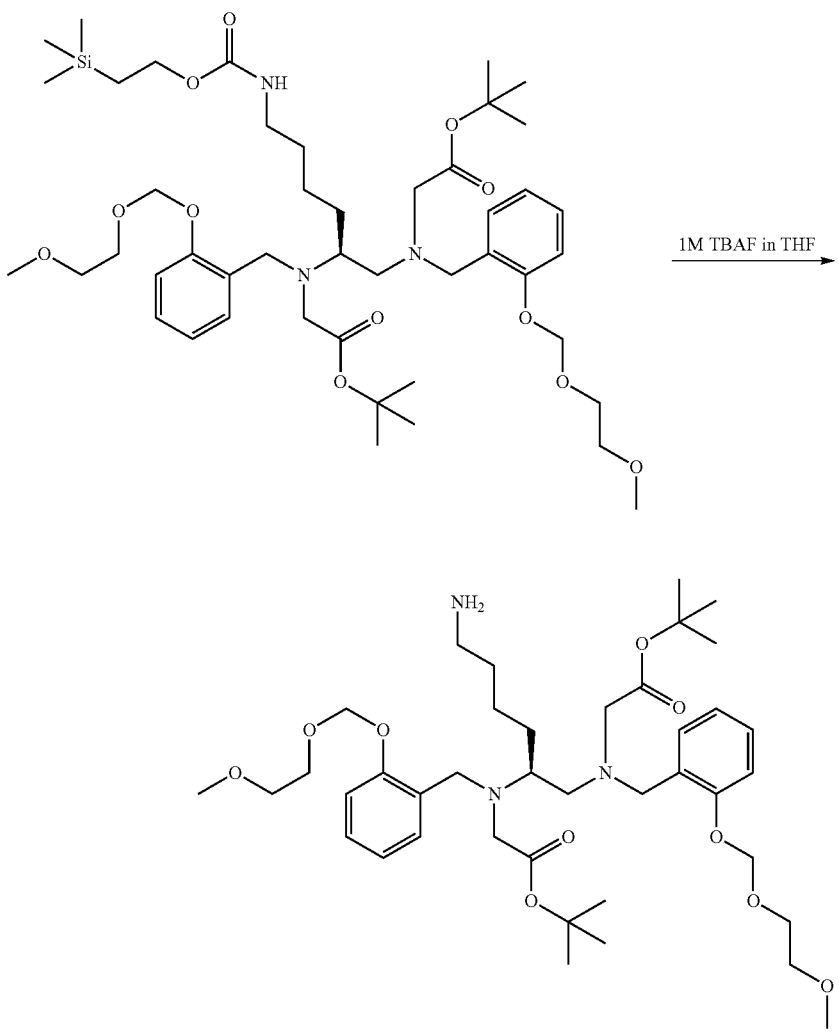

The ester compound 24 (0.89 g, 1.0 mmol) is dissolved in a 1M solution of TBAF in tetrahydrofuran (3.04 mL) and the reaction is allowed to continue stirring overnight. The reaction mixture is then poured into of saturated aqueous potassium carbonate (25 mL) solution and diluted with water (150 mL) and dichloromethane (75 mL). The aqueous and organic layers are separated; the aqueous layer extracted with dichloromethane (3×25 mL) and the combined organic layers are dried (magnesium sulfate), filtered and concentrated under reduced pressure to provide the crude product as a yellow oil. The residue is purified by flash chromatography ($SiO_2$, 120 gram column, 0 to 10% ethyl acetate-hexanes, 0.5% triethylamine) to obtain the amine compound 25.

Example 29

Preparation of Iron Compound 26

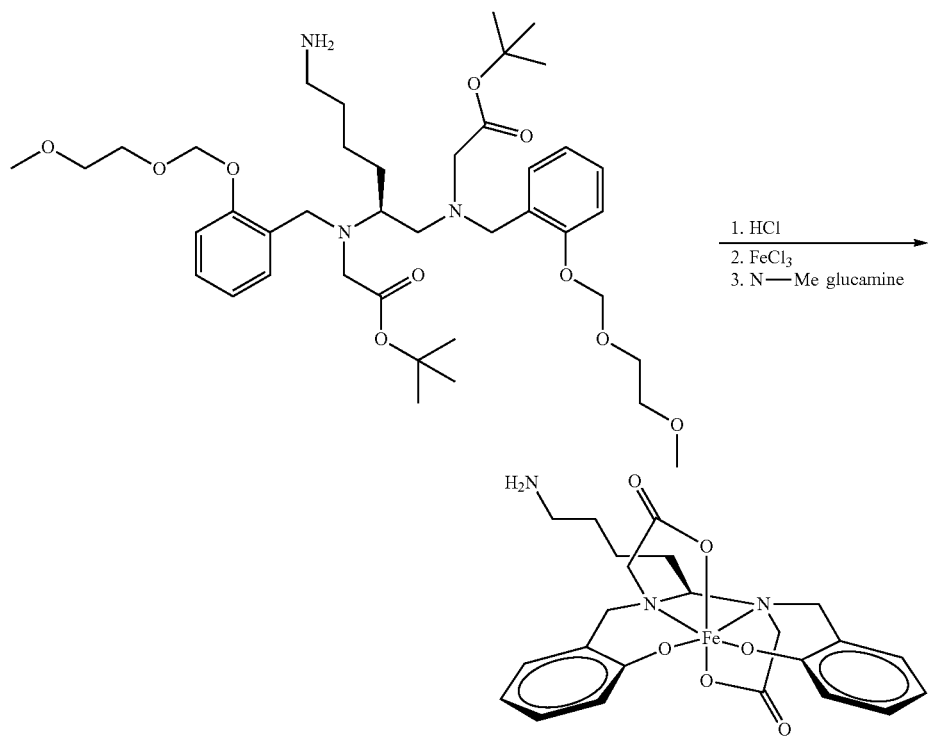

A portion of amine compound 25 (45 mg, 0.06 mmol) is deprotected by stirring overnight in a 1 M HCl solution (3:1 dioxane-water, 1.5 mL). A solution of iron chloride hexahydrate (19.4 mg, 0.076 mmol) in deionized water (1 mL) is introduced to the deprotected ligand and the mixture stirred for 1 hour at room temperature. The solution is then quenched to pH 9 with N-methyl glucamine. The mixture is loaded into a 3500 Da MWCO dialysis membrane and placed in a water bath of approximately 100× larger in volume than the membrane. The water bath is stirred and changed at 2 h, 26 h, 50 h, and at 68 h. Following the final change the bath is allowed to continue stirring for an additional 2 h. The dialysis retentate material is filtered through a sintered glass frit, concentrated under reduced pressure and lyophilized to yield the iron compound 26 as a red solid.

Example 30

Hydrodynamic Size Assay

The hydrodynamic diameter ($D_H$) of 10K pegylated iron compound 11 was measured via dynamic light (DLS) scattering in a PBS solution The compound was filtered through a 100 nm filter and optionally a 20 nm filter to remove dust prior to the DLS analysis using a Brookhaven ZetaPALS instrument. The dilution was carried out to yield approximately 20,000 counts per second during the DLS measurement and the sample was allowed to equilibrate for 10 minutes in the instrument prior to data collection. As shown in FIG. 2, it was noted that the bifunctionality enables pegylation of the iron chelate to systematically increase the agent size and potentially optimize in-vivo tissue distribution properties.

Example 31

Hydroxy Apatite (Bone) Binding Assay

A 2 mM stock solution of the 10K pegylated iron compound 11 was prepared in deionized water and the UV-Vis spectrum was recorded. The wavelength and intensity of the absorbance maximum ($\lambda_{max}$) in the visible region were noted. Hydroxyapatite type 1 (HA, obtained from Sigma Aldrich) was washed with deionized water and the solid was isolated by centrifugation at 3000 rcf, for 15 mM, followed by decanting of the aqueous solution. The remaining slurry was allowed to dry and a portion of the resulting white solid (250 mg) was combined with the 2 mM solution of 10K-Pegylated iron compound 11 (2 mL) in an Eppendorf tube. A control solution of a stock solution containing the 10K pegylated iron compound 11 (2 mL, 2 mM) was prepared in a second Eppendorf tube. Aliquots (200 uL) of the assay and control solutions were diluted with deionized water (1.8 mL) after a period of 1 h and 24 h. The UV-Vis spectra were recorded, and the wavelength and intensity of the $\lambda_{max}$ in the visible region were observed. The $\lambda_{max}$ intensity ratio of the assay to control samples having no hydroxy apatite was then calculated to estimate the relative amounts of free and bound 10K pegylated iron compound 11 at each timepoint. The following chelates were evaluated: FeDTPMP (a control bearing multiple phosphonates), FeHBEDP (a non-pegylated iron chelate control); and the 2 K, 5 K, 10 K pegylated bifunctional iron chelates of the invention. It was observed that the pegylated bifunctional iron chelates provided by the present invention generally demonstrated no binding affinity for HA (which is taken as a measure of bone binding affinity) relative to the control samples (See FIG. 3). It is noteworthy that the data for pegylated bifunctional iron chelates suggests that a greater peg size concomitantly reduces the overall bone binding affinity relative to an unhydroxylated parent chelate FeHBEDP).

Example 32

Relaxivity Determination and Protein Binding Studies

A stock solution having a concentration of 1 mM of the contrast enhancement agent was prepared in phosphate buffered saline (PBS) and the iron concentration was verified by elemental analysis. Separate 0.75 mM, 0.50 mM and 0.25 mM samples were prepared from the stock by dilution in PBS and the $T_1$ and $T_2$ relaxations times were recorded in triplicate for each sample on a Bruker Minispec mq60 instrument (60 MHz, 40° C.). The relaxivities ($r_1$ and $r_2$) were obtained as the gradient of $1/T_x$ (x=1, 2) plotted against iron chelate concentration following linear least squares regression analysis. Data for bifunctional contrast enhancement agents bearing PEGs of molecular weights 2 K, 3.5 K, 5 K and 10 K, was compared to the non-hydroxylated small molecule control chelate (FeHBEDP). Data shown in FIG. 4 (PBS) illustrate the beneficial effect of bifunctional pegylation on the relaxivities exhibited by the contrast enhancement agents provided by the present invention relative to the control samples. Increasing the size of the iron chelate concomitantly increased the relaxivity to the highest recorded PBS relaxivities of physiologically acceptable iron chelates.

The relaxivity experiments were repeated under identical conditions with the exception of the use of human serum (FIG. 4, serum) instead of PBS. Protein binding agents, such as FeHBEDP, are known to increase in relaxivity due to the restricted molecular rotation arising from the protein binding as shown in FIG. 4. However, the benefits of MRI signal increase provided by this effect are countered by the risk of increased toxicity arising from the increased liophilicity of the agents. There is therefore a need to maximize agent signal while controlling agent lipophilicity. Comparison of the serum and PBS relaxivity data in FIG. 4 for the 2 K, 3.5 K, 5 K PEG-iron chelates to FeHBEDP demonstrated increasing PEG molecular weight concomitantly reduced the protein binding. Therefore pegylation of the bifunctional iron chelate provides contrast agents with the benefit of maximum relaxivity arising from increased size and minimal toxicity risk from strong protein binding.

Example 33

Tumor Imaging

Cell Preparation: MATBIII breast cells (available from ATCC®) were trypsinized using 1× trypsin-EDTA. The cells were washed using IX phosphate buffered saline (PBS) and aliquots of 2×10⁶ cells were made in 1×PBS (100 uL). Prior to injection into the subject, 50 μL of basement membrane matrix (Matrigel®, BD Biosciences) was added to each aliquot.

Tumor Induction: All procedures involving animals were completed under protocols approved by the GE Global Research Institutional Animal Care and Use Committee. Female, 5-7 weeks old, SCID mice (Charles River Laboratories) were briefly anesthetized with 2% isoflurane and injected with 1×10⁶ MATBIII breast cancer cells in 1×PBS (100 μL) and Matrigel SC to their left flank. The animals were monitored for 7 days post tumor cell injections at which point, precontrast agent MR images of the resulting lesions, typically 1 cm in diameter, were collected using the sequences described below.

Dynamic Imaging: All imaging was performed on a GE Signa 1.5T clinical MR scanner, equipped with a 5 cm diameter custom solenoid RF receiver coil positioned at the center of the scanner bore. The animals were anesthetized using (ketamine/diazepam) anesthesia and placed in the RF receiver coil. A series of 2D fast spoiled gradient echo (FSPGR) imaging sequences were collected (TE=3.9 ms, TR=150 ms, FA=90°, NEX=5, Freq./Phase=256×192, slice thickness=1 mm, FOV=5 cm) as prescan images. A multislice variable flip angle fast spoiled gradient echo sequence (flip angle range: 2, 5, 10, 15, 20, 30, 70 degrees, TE: 3.5 ms, TR: 35.5 ms; bandwidth: 244 MHz; matrix: 256×128; slice thickness: 1 mm; field of view: 7 cm, phase field of view: 0.75, NEX: 1, to estimate the native the $T_1$ tissue relaxation times of both the left ventricle of the heart and the whole tumor. A 15 minute dynamic multiphase (phase=11 seconds, spacing=0 seconds) sequence was collected using identical slice locations to the above variable flip angle experiment, with the exception of a fixed FA=70 degrees. After three phases were completed, the animals were injected with a medical formulation comprising 2K PEG-FeHBEDP (the pegylated iron having structure B, Q=protonated meglumine) (0.2 mmolkg⁻¹ [Fe], 25 mM, ~200 μL), through the tail vein. After the dynamic image acquisition was completed, the post scan variable flip angle and 2D-FSPGR images were acquired.

Image Analysis: Post imaging analysis was performed using a Cine custom software tool (CineTool v8.0.9, GE Healthcare) built upon the IDL platform (IDL v. 6.3, ITT Corp., Boulder, Colo.). Regions of Interest (ROIs) were drawn manually and the intensities normalized to internal corn oil phantoms for comparison to the precontrast MR images. The DCE MR sequence was used to estimate agent concentration within the heart, tumor, and muscle, based on changes in initial tissue $T_1$ obtained from the multi-flip angle reference experiment before agent injection (0.2 mmol/kg). The concentration time curve was then fit to a two-compartment model (Tofts), using pharmacokinetic parameters of volume transfer ($K^{trans}$), agent efflux rate ($k_{ep}$) and fractional blood volume ($f_{PV}$) with the Cinetool. The blood half-lives of the agents are estimated through a multi exponential modeling of the change in agent concentration in the left ventricle arising from bolus effects, tissue distribution and elimination.

FIG. 5 illustrates dynamic $T_1$-weighted MR images before ("Pre") administering and after injection of the 2K PEG-FeHBEDP MR contrast agent (0.2 mmol kg⁻¹) in a mammary MATBIII tumor bearing mouse model described above. The left ventricle (LV, marked by arrow) of the heart was strongly enhanced during the initial phase ("Bolus") of the enhancement profile. Over the course of the imaging experiment, the distribution of the contrast agent to the tumor tissue (Tumor, marked by the arrow in "Distribution") was reflected by an enhancement of the tissue and enabled MR detection of the malignancy. Finally, the MR signal in the heart and tumor tissue diminished as the agent was eliminated from the body ("Elimination").

FIG. 6 summarizes the above image analysis of increasing pegylated iron chelate size on the blood distribution half-life of the MATBIII mouse model described above. Small molecule clinical contrast agents are known to clear rapidly and non-selectively from the vascularity to both malignant and benign tissue, limiting diagnostic imaging time and sensitivity. There is a need to increase the vascular residence time and tissue selectivity of contrast agents, which was anticipated to be accomplished by increasing agent size. A comparison of 2 K, 3.5 K, 5 K, 10K pegylated iron chelates to the clinical gadolinium chelate, Magnevist, and the experimental protein binding iron chelate, FeHBEDP, unexpectedly showed that agents of 2.5-4.5 nm in size (2 K and 3.5 K PEG) were more rapidly distributed from the blood than the small molecule controls. However, analogs of 5 nm and greater size (5 K and 10 K PEG) demonstrated prolonged vascular residence times that increased with agent size. The non-linear vascular residence time of the PEG agents indicated that the pharmacokinetics can be significantly and counter-intuitively tailored and optimized for a given indication over a relatively small size range (2-5 nm).

FIGS. 7A and 7B illustrates a comparison of whole tumor (FIG. 7 A) and muscle (FIG. 7 B) dynamic contrast enhanced (DCE) MR profiles of pegylated iron chelates to that of the gadolinium agent Magnevist (dose: 0.2 mmol/kg Gd, Fe) in a mammary MBIII rodent tumor model. The rates of small molecule Gd tumor tissue extravasation (FIG. 7A) and enhancement are too fast on the MR imaging timescale, and the tumor tissue selectivity (FIG. 7B) suboptimal, to allow accurate pharmacokinetic differentiation of malignant and benign tissues. Larger contrast agents that provide slower enhancement rates and better tumor tissue selectivity would improve the diagnostic sensitivity and specificity of DCE MR contrast agents for cancer. In comparison to the clinical gadolinium agent, the lesion enhancement rates of the pegylated iron agents were reduced to afford a longer dynamic MR imaging window for more precise lesion pharmacokinetic characterization. Also, the background muscle enhancements were low for pegylated iron agents, with no kinetic evidence for prolonged muscle extravasation beyond 3 nm Fe. Tumor-to-muscle signal enhancement ratios were used as a proxy for tissue selectivity and indicated improved lesion selectivity for 3-6 nm Fe agents when compared to 1 nm Gd (Table 8 below). The combination of improved lesion selectivity and slower pharmacokinetics indicated that 3-6 nm agents may better distinguish malignant and benign lesions than Gd ECF in a clinical cancer DCE MR setting.

TABLE 8

Tumor-to-muscle signal enhancement ratios for different samples

| Agent (Size) | Tumor: Muscle | |
|---|---|---|
| | Average | s.d. |
| Magnevist - Gd (1 nm) | 3.6 | 0.8 |
| 2K PEG-Fe (2.5 nm) | 5.3 | 1.3 |
| 3.5K PEG-Fe (4.5 nm) | 5.3 | 1.5 |
| 5K PEG-Fe (5.5 nm) | 6.5 | 1.3 |

FIGS. 8 A to 8 C illustrate a comparison of DCE MR pharmacokinetic characterization of whole tumor and muscle tissue with 2 K and 3.5 K pegylated iron chelates to clinical gadolinium chelate and FeHBEDP controls. The pharmacokinetic parameters ($K^{trans}$ and $V_e$) are generated from the concentration-time curve of the left ventricle and tumor signal (FIG. 8A). Both pegylated iron agents differentiated tumor and benign muscle tissue by vascular permeability ($K^{trans}$) quantitation more effectively than the small molecule chelate controls (FIG. 8B). The rapid distribution of the small gadolinium agent lead to a large and variable $K^{trans}$, whereas the parent protein binding iron chelate distributed slowly to both tumor and muscle tissue. The larger extravascular extracellular volume ($V_e$) of tumor tissue was detected with all agents and could be used to differentiate benign muscle from and malignant regions (FIG. 8 C). Notably, the 3.5K pegylated iron $K^{trans}$ coefficient of muscle could not be fitted to the Tofts model (rsq<0.8) or differentiated from the baseline, suggesting little permeation into the muscle tissue. This indicated the threshold for intravascular agent properties occurs at approximately 4.5 nm.

What is claimed is:
1. A contrast agent composition, comprising:
a pharmaceutically acceptable carrier or excipient; and
a metal-complex derived from a metal and a ligand having a structure (XXXI):

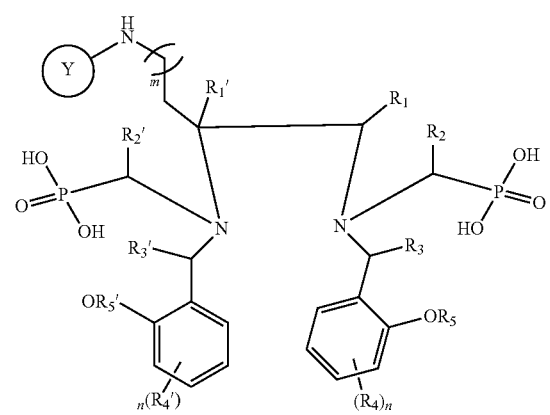

(XXXI)

wherein $R_1$, $R_2$, $R_3$, $R'_1$, $R'_2$, and $R'_3$, are independently at each occurrence hydrogen, or a $C_1$-$C_3$ alkyl group;
$R_4$ and $R'_4$ are independently at each occurrence hydrogen or a $C_1$-$C_3$ alkyl group; and n is an integer between 0 and 4;
$R_5$ and $R'_5$ are independently at each occurrence hydrogen or a group selected from the group consisting of $C_1$-$C_{30}$ aliphatic radicals, $C_3$-$C_{30}$ cycloaliphatic radicals, $C_2$-$C_{30}$ aromatic radicals; and m is an integer between 0 and 10; and
Y comprises a polyethylene glycol (PEG) moiety; and wherein the metal is Fe, Mn, Ga, In, Gd, W, Ta, or B.
2. The contrast agent composition of claim 1, wherein at least one of the $R_5$ and $R'_5$ of the ligand is independently at each occurrence a hydrogen, an ethyl, a trichloroethyl, a beta-cyanoethyl, a trimethylsilyl ethyl, butyldimethylsilyl, trimethylsilyl, methoxyethoxymethyl (MEM), a 2-(trimethylsilyl)ethoxymethyl (SEM), a tetrahydropyranyl (THP), a triisopropylsilyl (TIPS), a tert-butyl (t-Bu), a tert-butyldiphenylsilyl (TBDPS), a benzyloxymethyl (BOM), a methylthiomethyl (MTM) or a combination thereof.

3. The contrast agent composition of claim 1, wherein at least one of the $R_5$ and $R'_5$ of the ligand is independently at each occurrence a methoxyethoxymethyl (MEM) group.

4. The contrast agent composition of claim 1, wherein $R_1$, $R_2$, $R_3$, $R_4$, and $R_5$ are the same as $R_1'$, $R_2'$, $R_3'$, $R_4'$, and $R_5'$ of the ligand, respectively.

5. The contrast agent composition of claim 1, wherein the polyethylene glycol moiety has an average molecular weight greater than about 2000 daltons and less than or equal to about 30,000 daltons.

6. The contrast agent composition of claim 1, wherein the polyethylene glycol moiety has an average molecular weight in a range from about 5000 daltons to about 10,000 daltons.

7. The contrast agent composition of claim 1, wherein the ligand has a structure XXXIII-A:

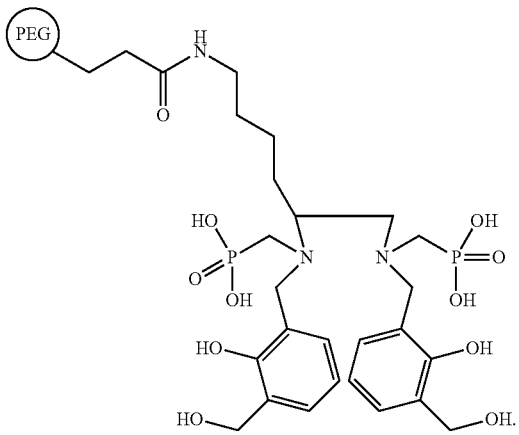

(XXXIII-A)

8. The contrast agent composition of claim 1, wherein the ligand has a structure XXXIII-B:

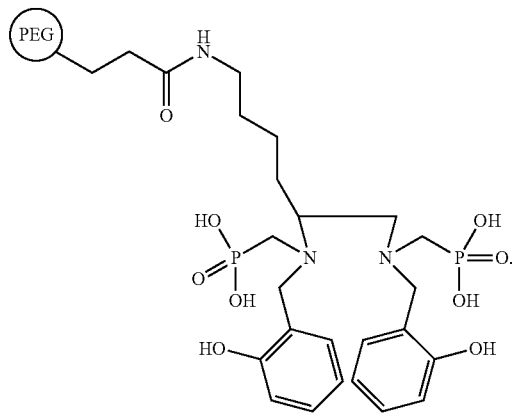

(XXXIII-B)

9. The contrast agent composition of claim 1, wherein the metal is iron.

10. The contrast agent composition of claim 1, wherein the contrast agent composition is suitable for injection into a mammalian subject.

11. The contrast agent composition of claim 1, wherein the contrast agent composition is suitable for injection into a human subject.

12. The contrast agent composition of claim 1, wherein the metal-complex is characterized by an average aqueous hydrodynamic diameter (DH), as determined by dynamic light scattering, in a range from about 2 nm to about 500 nm.

13. The contrast agent composition of claim 12, wherein the metal-complex is characterized by its ability to form a stable aqueous solution that exhibits no substantial change in the aqueous hydrodynamic diameter ($D_H$) as determined by dynamic light scattering after one or more of a tangential flow filtration, dialysis, ultrafiltration, or storage for one week at room temperature.

14. The contrast agent composition of claim 1, wherein the contrast agent composition is suitable for use in magnetic resonance (MR), nuclear or X-ray imaging.

15. The contrast agent composition of claim 1, wherein the carrier or excipient is an isotonic aqueous medium.

16. The contrast agent composition of claim 1, wherein the carrier or excipient is at physiological pH.

17. A contrast agent composition suitable for injection into a mammalian subject, comprising:
    a pharmaceutically acceptable carrier or excipient; and
    a metal-complex having a structure (XXXXII):

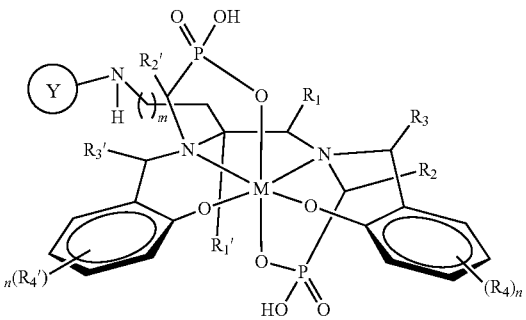

(XXXXII)

wherein $R_1$, $R_2$, $R_3$, $R'_1$, $R'_2$, and $R'_3$ are independently at each occurrence hydrogen, or a $C_1$-$C_3$ alkyl group;
$R_4$ and $R'_4$ are independently at each occurrence a hydrogen or a $C_1$-$C_3$ alkyl group; n is an integer between 0 and 4; m is an integer between 0 and 10; and
Y comprises a polyethylene glycol (PEG) moiety; and wherein the M is Fe, Mn, Ga, In, Gd, W, Ta, or B.

18. The contrast agent composition of claim 17, wherein the polyethylene glycol moiety has an average molecular weight greater than about 2000 daltons and less than or equal to about 30,000 daltons.

19. The contrast agent composition of claim 17, wherein the metal-complex is a racemate, a single enantiomer, an enantiomerically enriched composition, or a mixture of diastereomers.

20. The contrast agent composition of claim 17, wherein the metal-complex has a structure XXXXIV

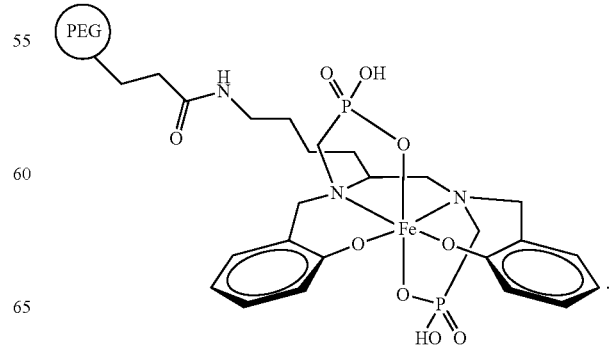

(XXXXIV)

21. A contrast agent composition, comprising:
a pharmaceutically acceptable carrier or excipient; and
a metal-complex derived from a metal and a ligand having structure (XXX):

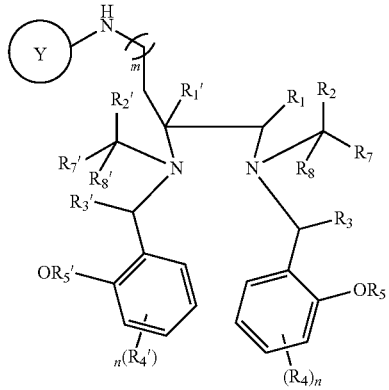
(XXX)

wherein $R_1$, $R_2$, $R_3$, $R_4$, $R_8$, $R'_1$, $R'_2$, $R'_3$, $R'_4$ and $R_8'$ are independently at each occurrence hydrogen or a $C_1$-$C_3$ alkyl group;

$R_5$ and $R'_5$ are independently at each occurrence hydrogen or a group selected from the group consisting of $C_1$-$C_{30}$ aliphatic radicals, $C_3$-$C_{30}$ cycloaliphatic radicals, $C_2$-$C_{30}$ aromatic radicals; n is an integer between 0 and 4; m is an integer between 0 and 10;

$R_7$ and $R'_7$ are independently at each occurrence a phosphonic acid group or a phosphonate group; and Y comprises a polyethylene glycol (PEG) moiety; and wherein the metal is Fe, Mn, Ga, In, Gd, W, Ta, or B.

* * * * *